(12) United States Patent
Cheng et al.

(10) Patent No.: US 9,226,974 B2
(45) Date of Patent: *Jan. 5, 2016

(54) ANTIPROLIFERATIVE COMPOUNDS, CONJUGATES THEREOF, METHODS THEREFOR, AND USES THEREOF

(71) Applicant: E. R. Squibb & Sons, L.L.C., Princeton, NJ (US)

(72) Inventors: Heng Cheng, Foster City, CA (US); Sanjeev Gangwar, Foster City, CA (US); Qiang Cong, Sunnyvale, CA (US)

(73) Assignee: E. R. SQUIBB & SONS, L.L.C., Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/324,480

(22) Filed: Jul. 7, 2014

(65) Prior Publication Data

US 2014/0323690 A1 Oct. 30, 2014

Related U.S. Application Data

(60) Continuation of application No. 13/752,619, filed on Jan. 29, 2013, now Pat. No. 8,802,632, which is a division of application No. 12/846,493, filed on Jul. 29, 2010, now Pat. No. 8,394,922.

(60) Provisional application No. 61/232,883, filed on Aug. 11, 2009, provisional application No. 61/230,932, filed on Aug. 3, 2009.

(51) Int. Cl.

| | |
|---|---|
| A61K 39/395 | (2006.01) |
| A61K 47/48 | (2006.01) |
| C07K 5/02 | (2006.01) |
| C07K 5/078 | (2006.01) |
| C07K 5/10 | (2006.01) |
| C07K 16/18 | (2006.01) |
| C07C 229/14 | (2006.01) |
| C07C 229/16 | (2006.01) |
| A61K 38/06 | (2006.01) |

(52) U.S. Cl.
CPC .......... *A61K 47/48415* (2013.01); *A61K 38/06* (2013.01); *A61K 47/48484* (2013.01); *C07C 229/14* (2013.01); *C07C 229/16* (2013.01); *C07K 5/021* (2013.01); *C07K 5/06139* (2013.01); *C07K 5/10* (2013.01); *C07K 16/18* (2013.01)

(58) Field of Classification Search
None
See application file for complete search history.

(56) References Cited

U.S. PATENT DOCUMENTS

| | | | |
|---|---|---|---|
| 6,984,720 B1 | 1/2006 | Korman | |
| 6,989,452 B2 | 1/2006 | Ng | |
| 7,087,600 B2 | 8/2006 | Ng | |
| 7,129,261 B2 | 10/2006 | Ng | |
| 7,335,748 B2 | 2/2008 | Harkins | |
| 7,387,776 B2 | 6/2008 | Keler | |
| 7,691,962 B2 | 4/2010 | Boyd | |
| 7,754,885 B2 | 7/2010 | Hoefle | |
| 8,394,922 B2 * | 3/2013 | Cheng et al. ............ 530/331 |
| 2002/0169125 A1 | 11/2002 | Leung | |
| 2005/0239713 A1 | 10/2005 | Domling | |
| 2005/0249740 A1 | 11/2005 | Domling | |
| 2006/0004081 A1 | 1/2006 | Chen | |
| 2006/0128754 A1 | 6/2006 | Hoefle | |
| 2006/0217360 A1 | 9/2006 | Hoefle | |
| 2006/0247295 A1 | 11/2006 | Gangwar | |
| 2008/0176958 A1 | 7/2008 | Davis | |
| 2008/0248052 A1 | 10/2008 | Vlahov | |
| 2008/0279868 A1 | 11/2008 | Boyd | |
| 2008/0281102 A1 | 11/2008 | Gangwar | |
| 2008/0293800 A1 | 11/2008 | Gangwar | |
| 2009/0028872 A1 | 1/2009 | Terret | |
| 2009/0074660 A1 | 3/2009 | Korman | |
| 2009/0142349 A1 | 6/2009 | Rao-Naik | |
| 2009/0217401 A1 | 8/2009 | Korman | |
| 2009/0297438 A1 | 12/2009 | Huang | |
| 2010/0034826 A1 | 2/2010 | Terrett | |
| 2010/0047841 A1 | 2/2010 | Wipf | |

(Continued)

FOREIGN PATENT DOCUMENTS

| | | |
|---|---|---|
| DE | 100 08 089 A1 | 10/2001 |
| DE | 10 2004 030 227 A1 | 1/2006 |

(Continued)

OTHER PUBLICATIONS

Balasubramanian et al., *Bioorg. Med. Chem. Lett.* 2008, 18, 2996-2999, "Tubulysin analogs incorporating desmethyl and dimethyl tubuphenylalanine derivatives".
Balasubramanian et al., *J. Med. Chem.*, 2009, 52 (2), 238-240, "Total Synthesis and Biological Evaluation of Tubulysin U, Tubulysin V, and Their Analogues".
CAS Abstract No. 128:256473 (abstract of WO 98/13375), (1999).
CAS Abstract No. 135:331296 (abstract of DE 10008089 A1), (2001).
CAS Abstract No. 144:143058 (abstract of DE 102004030227 A1), (2006).
Domling et al., *Angew. Chem. Int. Ed.* 2006, 45, 7235-7239, "Total Synthesis of Tubulysin U and V**".
Domling et al., *Mol. Diversity* 2005, 141-147, "Myxobacterial epothilones and tubulysins as promising anticancer agents".
Dubowchik et al., *Bioconjugate Chem.* 2002, 13, 855-869, "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity".

(Continued)

Primary Examiner — Sheela J Huff
(74) Attorney, Agent, or Firm — Yuan Chao

(57) ABSTRACT

Antiproliferative compounds having a structure represented by formula (II), where n, $R^1$, $R^2$, $R^3$, $R^4$, and $R^5$ are as defined herein, can be used to treat tumors, optionally when conjugated to a ligand such as an antibody:

(II)

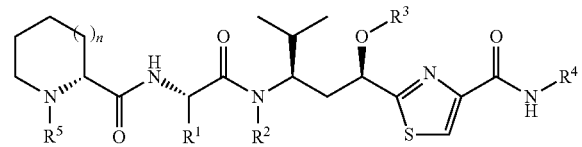

8 Claims, 27 Drawing Sheets

(56) References Cited

U.S. PATENT DOCUMENTS

| | | |
|---|---|---|
| 2010/0048490 A1 | 2/2010 | Vlahov |
| 2010/0092484 A1 | 4/2010 | Xu |
| 2010/0113476 A1 | 5/2010 | Chen |

FOREIGN PATENT DOCUMENTS

| | | |
|---|---|---|
| EP | 2174947 A1 | 4/2010 |
| WO | WO 97/21712 A1 | 6/1997 |
| WO | WO 98/13375 A1 | 4/1998 |
| WO | WO 02/096910 A1 | 12/2002 |
| WO | WO 2008/070569 A2 | 6/2008 |
| WO | WO 2008/074004 A2 | 6/2008 |
| WO | WO 2008/083312 A2 | 7/2008 |
| WO | WO 2008/138561 A1 | 11/2008 |
| WO | WO 2009/002993 A1 | 12/2008 |
| WO | WO 2009/012958 A2 | 1/2009 |
| WO | WO 2009/026177 A1 | 2/2009 |
| WO | WO 2009/05562 A1 | 4/2009 |
| WO | WO 2009/045957 A1 | 4/2009 |
| WO | WO 2010/034724 A1 | 4/2010 |
| WO | WO 2011/057805 A1 | 5/2011 |

OTHER PUBLICATIONS

Dubowchik et al., *Bioorg. Med. Chem. Lett.* 1998, 8, 3341-3346, "Cathepsin B-Sensitive Dipeptide Prodrugs. 1. A Model Study of Structural Requirements for Efficient Release of Doxorubicin."

Dubowchik et al., *Bioorg. Med. Chem. Lett.* 1998, 8, 3347-3352, "Cathepsin B-Sensitive Dipeptide Prodrugs. 2. Models of Anticancer Drugs Paclitaxel (Taxol®), Mitomycin C and Doxorubicin".

Hamel et al., *Curr. Med. Chem.—Anti-Cancer Agents* 2002, 2, 19-53, "Antimitotic Peptides and Depsipeptides".

Hofle et al., *Pure Appl. Chem.* 2003, 75 (2-3), 167-178, "Semisynthesis and degradation of the tubulin inhibitors epothilone and tubulysin".

Kaur et al., *Biochem. J.* 2006, 396, 235-242, "Biological evaluation of tubulysin A: a potential anticancer and antiangiogenic natural product".

Khalil et al., *ChemBioChem* 2006, 7, 678-683, "Mechanism of Action of Tubulysin, an Antimitotic Peptide from Myxobacteria".

Leamon et al., *Cancer Res.* 2008; 68 (23), 9839-9844, "Folate Targeting Enables Durable and Specific Anti-tumor Responses from a Therapeutically Null Tubulysin B Analogue".

Lundquist et al., *Org. Lett.* 2001, 3 (5), 781-783, "Improved Solid-Phase Peptide Synthesis Method Utilizing r-Azide-Protected Amino Acids".

Neri et al., *ChemMedChem* 2006, 1, 175-180, "Efforts toward the Total Synthesis of Tubulysins: New Hopes for a More Effective Targeted Drug Delivery to Tumors".

Patterson et al., *Chem. Eur. J.* 2007, 13, 9534-95, "Design, Synthesis, and Biological Properties of Highly Potent Tubulysin D Analogues".

Patterson et al., *J. Org. Chem.* 2008, 73, 4362-4369, "Expedient Synthesis of N-Methyl Tubulysin Analogues with High Cytotoxicity".

Peltier et al., *J. Am. Chem. Soc.* 2006, 128, 16018-16019, "The Total Synthesis of Tubulysin D".

Reddy et al., *Mol. Pharm.* 6 (5), 1518-1525, "In Vivo Structural Activity and Optimization Studies of Folate-Tubulysin Conjugates", Jul. 24, 2009.

Sani et al., *Angew. Chem. Int. Ed.* 2007, 46, 3526-3529, "Total Synthesis of Tubulysins U and V**".

Sasse et al., *J. Antibiotics* 2000, 53 (9), 879-885, "Tubu-lysins, New Cytostatic Peptides from Myxobacteria Acting on Mitrotubuli Production, Isolation, Physico-chemical and Biological Properties".

Sasse et al., *Nature Chem. Biol.* 2007, 3 {2), 87-89, "Success in tubulysin D synthesis".

Schluep et al., *Clin. Cancer Res.* 2009, 15 (1)181-189, "Polymeric Tubulysin-Peptide Nanoparticles with Potent AntitumorActivity".

Shankar et al., *Synlett* 2009 (1) 1341-1345, "Studies towards a Novel Synthesis of Tubulysisn: Highly Asym-metric Aza-Michael Reactions of 2-Enoylthiazoles with Metalatd Chiral Oxazolidinones".

Shibue et al., *Tetrahedron Letters* 2009, 50, 3845-3848, "Stereoselective synthesis of tubuvaline methyl ester and tubuphenylalanine, components of tubulysins, tubulin polymerization inhibitors".

Steinmetz et al., *Angew. Chem Int. Ed.* 2004, 43, 4888-4892, "Isolation, Crystal and Solution Structure Deter-mination, and Biosynthesis of Tubulysins—Powerful Inhibitors of Tubulin Polymerization from Myxobacteria**".

Ullrich et al., *Angew. Chem. Int. Ed.* 2009, 48, 4422-4425, "Pretubulysin, a Potent and Chemically Accessible Tubulysin Precursor from Angiococcus disciformis".

Vlahov et al., *Bioorg. Med. Chem. Lett.* 2009, 18, 4558-4561, "Design and regioselective synthesis of a new generation of targeted chemotherapeutics. Part II: Folic acid conjugates of tubulysins and their hydrazides".

Wang et al., *Chem. Biol. Drug Des.* 2007; 70, 75-86, "Structure-activity and High-content Imaging Analyses of Novel Tubulysins".

Wipf et al., *Org. Lett.* 2004, 6 (22), 4057-4060, "Synthesis of the Tubuvaline-Tubuphenylalanine (Tuv-Tup) Fragment of Tubulysin".

Wipf et al., *Org. Lett.* 2007, 9 (8), 1605-1607, "Total Synthesis of $N^{14}$-desacetoxytubulysin H".

\* cited by examiner

Scheme 1 (part 1 of 2)

Scheme 1 (part 2 of 2)

Scheme 2

Scheme 3

Scheme 4

Scheme 5

Scheme 6

Scheme 7

Scheme 8

Scheme 9

Scheme 10

Scheme 11

Scheme 12

Scheme 13

Scheme 14

Scheme 15

Scheme 16

Scheme 17

Scheme 18 (part 1 of 2)

Scheme 18 (part 2 of 2)

Scheme 19

Compound 115

Scheme 20

Scheme 21

Scheme 22

Scheme 23

ANTIPROLIFERATIVE COMPOUNDS, CONJUGATES THEREOF, METHODS THEREFOR, AND USES THEREOF

CROSS-REFERENCE TO RELATED APPLICATIONS

This application claims the benefit under 35 U.S.C. §119 (e) of US Provisional Applications Nos. 61/230,932, filed Aug. 3, 2009; and 61/232,883, filed Aug. 11, 2009; the disclosure of which are incorporated herein by reference.

BACKGROUND OF THE INVENTION

This invention relates to compounds structurally related to the tubulysins, conjugates thereof with a ligand, methods for making and using such compounds and conjugates, and compositions comprising such compounds and conjugates.

The tubulysins are cytotoxins originally isolated from cultures of the myxobacteria *Archangium gephyra* or *Angiococcus disciformis*, with each organism producing a different mixture of tubulysins (Sasse et al. 2000; Reichenbach et al. 1998). Their crystal structure and biosynthetic pathway have been elucidated (Steinmetz et al. 2004) and their biosynthesis genes have been sequenced (Hoefle et al. 2006b). Pretubulysin, a biosynthetic precursor of the tubulysins, also has been shown to possess significant activity in its own right (Ullrich et al. 2009). (Full citations for the documents cited herein by first author or inventor and year are listed at the end of this specification.)

The tubulysins belong to a group of naturally occurring antimitotic polypeptides and depsipeptides that includes the phomopsins, the dolastatins, and the cryptophycins (Hamel 2002). Antimitotic agents other than polypeptides or depsipeptides also exist, for example paclitaxel, the maytansines, and the epothilones. During mitosis, a cell's microtubules reorganize to form the mitotic spindle, a process requiring the rapid assembly and disassembly of the microtubule constituent proteins α- and β-tubulin. Antimitotic agents block this process and prevent a cell from undergoing mitosis, although at the molecular level the exact blockage mechanism may differ from one agent to another. The tubulysins prevent the assembly of the tubulins into microtubules, causing the affected cells to accumulate in the $G_2/M$ phase and undergo apoptosis (Khalil et al. 2006). Conversely, paclitaxel effects the same end result by binding to microtubules and preventing their disassembly.

The tubulysins have a tetrapeptidyl scaffold constructed from one proteinogenic and three non-proteinogenic amino acid subunits: N-methylpipecolinic acid (Mep), isoleucine (Ile), tubuvaline (Tuv), and either tubuphenylalanine (Tup, $R^A$ equals H in formula (I) below) or tubutyrosine (Tut, $R^A$ equals OH). About a dozen naturally occurring tubulysins (named A, B, etc.) are known, the sites of structural variation among them being at residues $R^A$, $R^B$ and $R^C$ as shown in Formula (I) and Table 1:

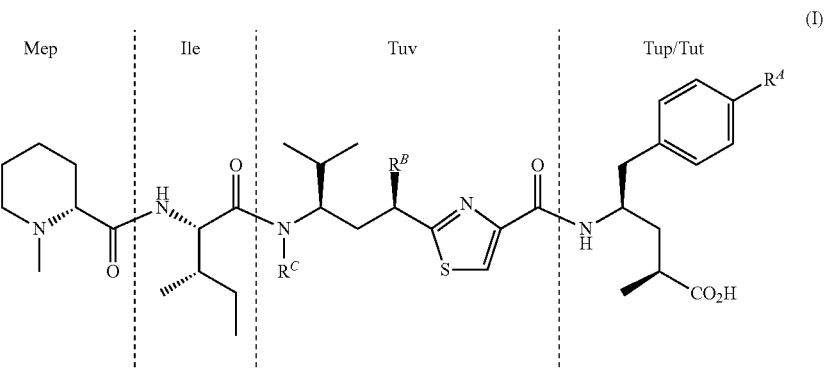

TABLE 1

Naturally Occurring Tubulysins

| Tubulysin | $R^A$ | $R^B$ | $R^C$ |
|---|---|---|---|
| A | OH | OC(=O)Me | $CH_2OC$(=O)i-Bu |
| B | OH | OC(=O)Me | $CH_2OC$(=O)n-Pr |
| C | OH | OC(=O)Me | $CH_2OC$(=O)Et |
| D | H | OC(=O)Me | $CH_2OC$(=O)i-Bu |
| E | H | OC(=O)Me | $CH_2OC$(=O)n-Pr |
| F | H | OC(=O)Me | $CH_2OC$(=O)Et |
| G | OH | OC(=O)Me | $CH_2OC$(=O)CH=$CH_2$ |
| H | H | OC(=O)Me | $CH_2OC$(=O)Me |
| I | OH | OC(=O)Me | $CH_2OC$(=O)Me |
| U | H | OC(=O)Me | H |
| V | H | OH | H |
| Z | OH | OH | H |
| Pretubulysin | H | H | Me |

Kaur et al. 2006 studied the antiproliferative properties of tubulysin A and found that it was more potent than other antimitotic agents such as paclitaxel and vinblastine and was active in xenograft assays against a variety of cancer cell lines. Further, tubulysin A induced apoptosis in cancer cells but not normal cells and showed significant potential antiangiogenic properties in in vitro assays. The antimitotic properties of other tubulysins have also been evaluated and generally have been found to compare favorably against those of non-tubulysin antimitotic agents (see, e.g., Balasubramanian et al. 2009; Steinmetz et al. 2004; Wipf et al. 2004). For these reasons, there is considerable interest in the tubulysins as anti-cancer agents (see, e.g., Domling et al. 2005c; Hamel 2002).

Numerous publications describe efforts directed at the synthesis of tubulysins, including: Balasubramanian et al. 2009; Domling et al. 2006; Hoefle et al. 2003; Neri et al. 2006; Peltier et al. 2006; Sani et al. 2007; Sasse et al. 2007; Shankar et al. 2009; Shibue et al. 2009; and Wipf et al. 2004. Other publications describe structure-activity relationship (SAR) studies, via the preparation and evaluation of tubulysin analogs or derivatives: Balasubramanian et al. 2008 and 2009;

Domling 2006; Domling et al. 2005a; Ellman et al. 2009; Hoefle et al. 2001 & 2006a; Patterson et al. 2007 & 2008; Richter 2008; Vlahov et al. 2009; Wang et al. 2007; and Wipf et al. 2007 and 2010. The SAR studies mainly explored structural variations in the Mep ring, residues $R^B$ and $R^C$ of the Tuv subunit, and the aromatic ring or aliphatic carbon chain of the Tup/Tut subunit.

Domling et al. 2005 disclose conjugates of tubulysins with a partner molecule generically described as a polymer or a biomolecule, but with actual examples limited to polyethylene glycol (PEG) as the partner molecule. Other documents disclosing conjugates of tubulysins are Boyd et al. 2008 and 2010; Vlahov et al. 2008a, 2008b and 2010; Leamon et al. 2008 and 2009; Reddy et al. 2009; and Low et al. 2009. Leung et al. 2002 disclose polyanionic polypeptides that can be conjugated to drugs (including tubulysins) to improve their bioactivity and water solubility.

Davis et al. 2008 and Schluep et al. 2009 disclose cyclodextrin based formulations in which tubulysins are covalently attached to a cyclodextrin via a hydrazide-disulfide linker moiety bonded to the Tup/Tut carboxyl group.

BRIEF SUMMARY OF THE INVENTION

The present invention discloses novel antiproliferative compounds that are structurally related to the tubulysins, are cytotoxic or cytostatic against many cancer cells, and are believed to act by an antimitotic mechanism. These compounds can be conjugated to ligands such as antibodies for targeted delivery against cancer cells.

In one embodiment, this invention provides a compound having a structure represented by formula (II)

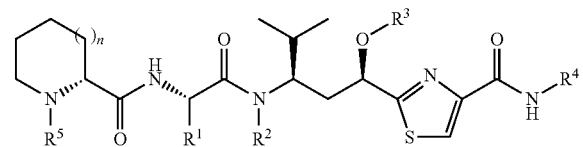

(II)

wherein n is 0, 1, or 2;

$R^1$, $R^2$ and $R^3$ are independently H, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted aryl, unsubstituted or substituted heteroaryl, unsubstituted or substituted $(CH_2)_{1-2}O(C_1$-$C_{10}$ alkyl), unsubstituted or substituted $(CH_2)_{1-2}O(C_2$-$C_{10}$ alkenyl), unsubstituted or substituted $(CH_2)_{1-2}O(C_2$-$C_{10}$ alkynyl), $(CH_2)_{1-2}OC(=O)(C_1$-$C_{10}$ alkyl), unsubstituted or substituted $(CH_2)_{1-2}OC(=O)(C_2$-$C_{10}$ alkenyl), unsubstituted or substituted $(CH_2)_{1-2}OC(=O)(C_2$-$C_{10}$ alkynyl), unsubstituted or substituted $C(=O)(C_1$-$C_{10}$ alkyl), unsubstituted or substituted $C(=O)(C_2$-$C_{10}$ alkenyl), unsubstituted or substituted $C(=O)(C_2$-$C_{10}$ alkynyl), unsubstituted or substituted cycloaliphatic, unsubstituted or substituted heterocycloaliphatic, unsubstituted or substituted arylalkyl, or unsubstituted or substituted alkylaryl;

$R^4$ is

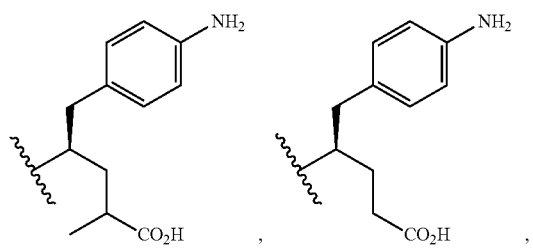

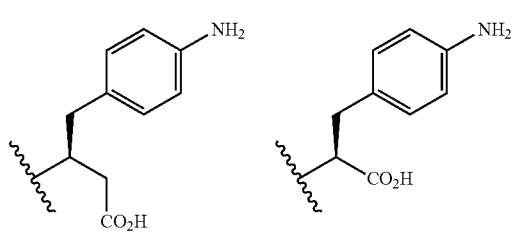

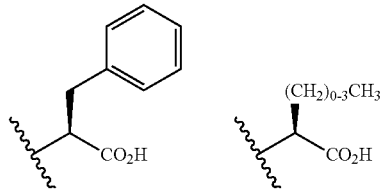

, or ;

and $R^5$ is H, $C_1$-$C_5$ alkyl, $C_2$-$C_5$ alkenyl, $C_2$-$C_5$ alkynyl, $CO(C_1$-$C_5$ alkyl), $CO(C_2$-$C_5$ alkenyl), or $CO(C_2$-$C_5$ alkynyl);

or a pharmaceutically acceptable ester thereof, a pharmaceutically acceptable amide thereof at the carboxyl group of $R^4$ with the α-amino group of an α-amino acid, or a pharmaceutically acceptable salt thereof.

A preferred $R^4$ is

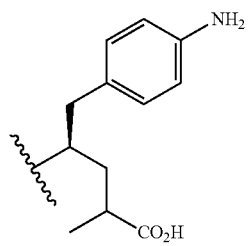 [SMILES: *[C@@H](Cc1ccc(N)cc1)CC(C)C(=O)O]

with the stereochemistry at the methyl group alpha to the carboxyl being more preferably that corresponding to the natural tubulysins, that is:

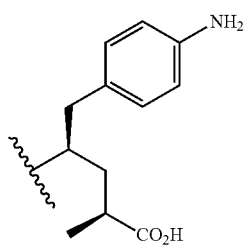

This invention also provides novel intermediates useful for synthesizing compounds according to formula (II).

In another embodiment, this invention provides a compound of this invention conjugated via a linker moiety to a ligand (preferably an antibody, more preferably a monoclonal antibody, and most preferably a human monoclonal antibody) for its selective delivery to a target cell such as a cancer cell.

In another embodiment, there is provided a composition of matter comprising a compound of this invention and a linker moiety, suitable for conjugation to a ligand.

In another embodiment, this invention provides a method for inhibiting the proliferation of cancer cells in a subject suffering from cancer, comprising administering to the subject a therapeutically effective amount of a compound of this invention or a conjugate thereof with a ligand (particularly an antibody). In another embodiment, there is provided a method for inhibiting the proliferation of cancer cells, comprising contacting such cells with a compound of this invention or a conjugate thereof with a ligand (particularly an antibody), under conditions sufficient to inhibit the growth of such cancer cells. The cancer cells can be colorectal cancer, liver cancer, prostate cancer, breast cancer, melanoma, glioblastoma, lung cancer, pancreatic cancer, ovarian cancer, multiple myeloma, renal cancer, leukemia, or lymphoma cells. Where the ligand is an antibody, it is preferred that the antibody binds to an antigen expressed by the cancer cells.

In another embodiment, there is provided a method of treating a cancer in a subject suffering from such cancer, comprising administering to the subject a therapeutically effective amount of a compound of this invention or a conjugate thereof with a ligand (particularly an antibody). In another embodiment, there is provided the use of a compound of this invention (or a conjugate thereof with a ligand (particularly an antibody) for the preparation of a medicament for the treatment of cancer. In these embodiments, the cancer can be colorectal cancer, liver cancer, prostate cancer, breast cancer, melanoma, glioblastoma, lung cancer, pancreatic cancer, ovarian cancer, multiple myeloma, renal cancer, leukemia, or lymphoma. Where the ligand is an antibody, it is preferred that the antibody binds to an antigen expressed by the cells of the cancer.

In another embodiment, there is provided the use of a compound of this invention or a conjugate thereof with a ligand (preferably an antibody) for the preparation of a medicament for treating a cancer in a subject suffering from such cancer.

BRIEF DESCRIPTION OF THE DRAWING(S)

Figure 5:
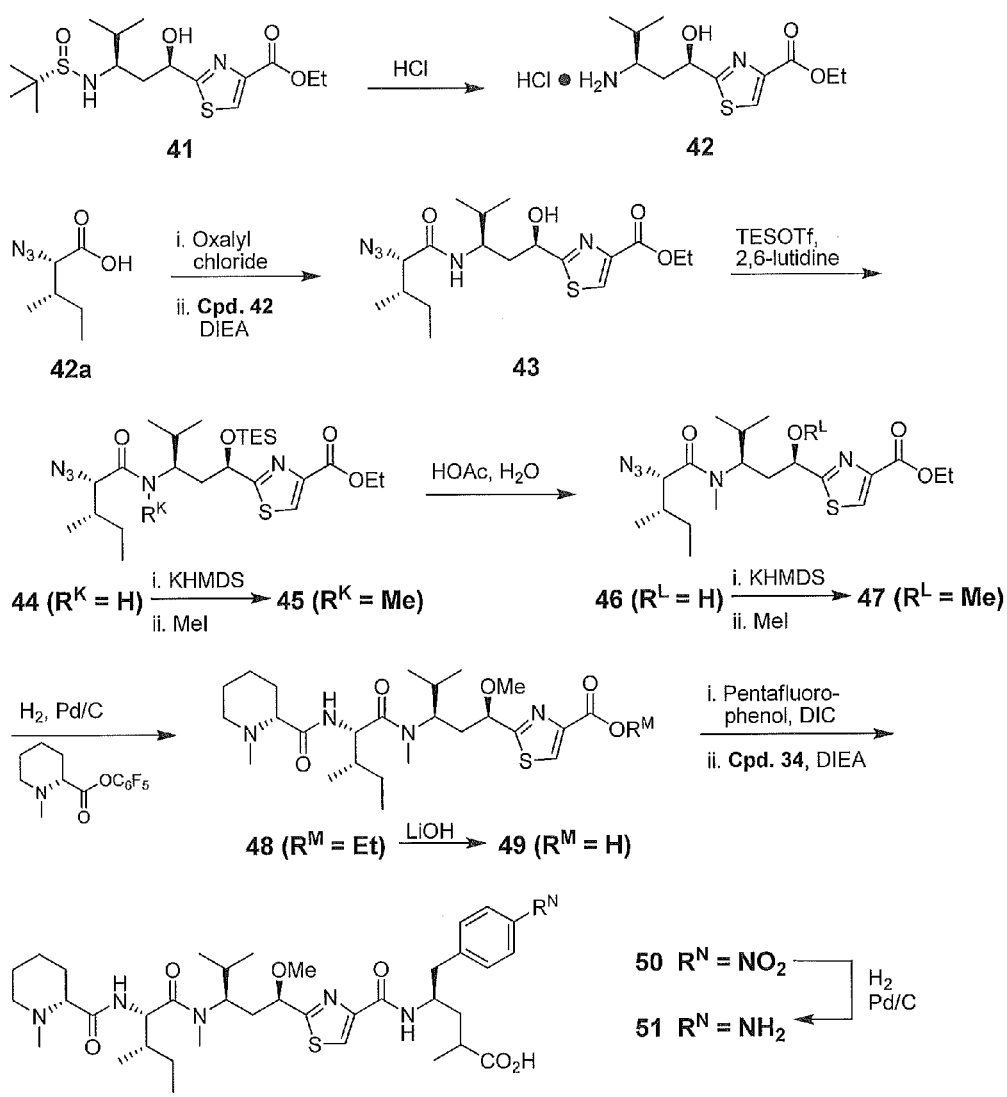
Figure 6:
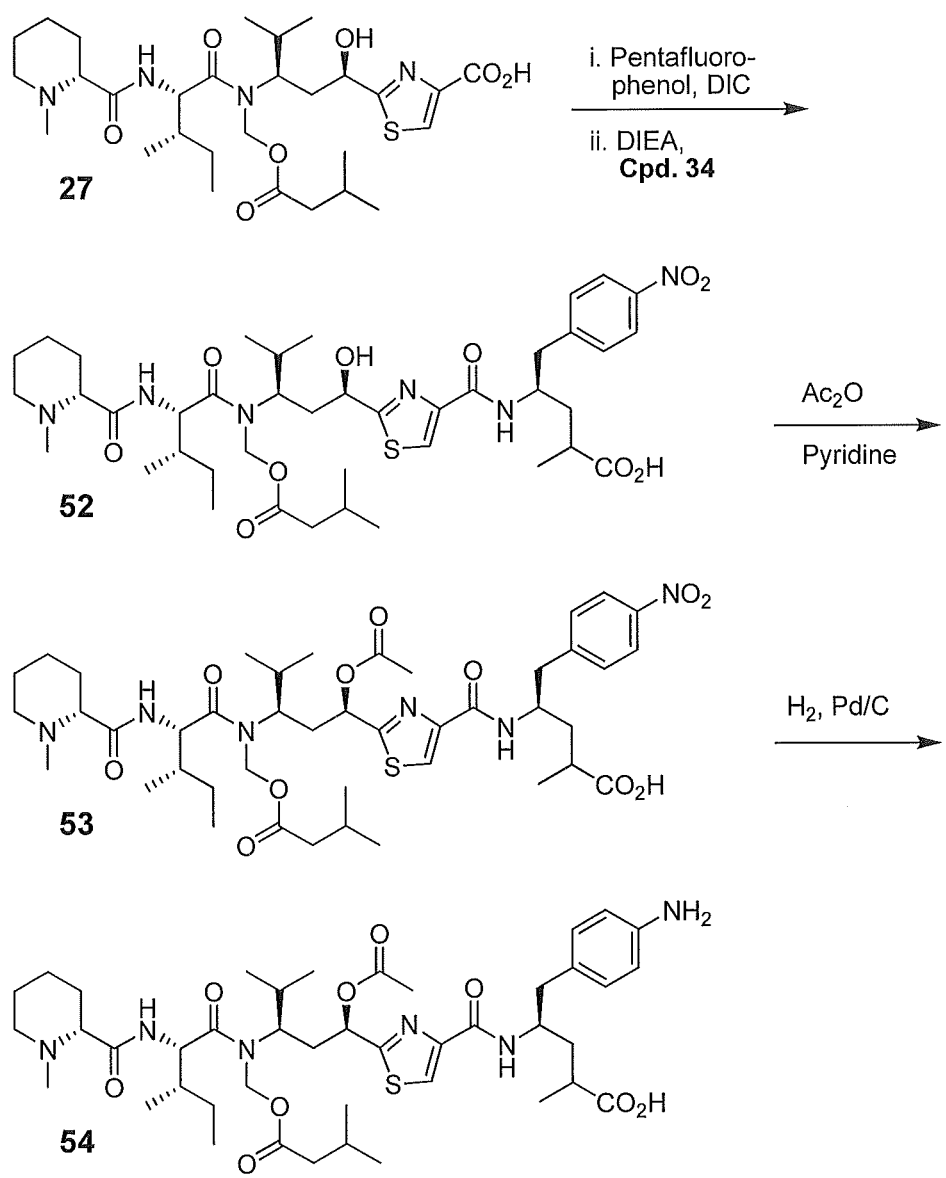
Figure 7:
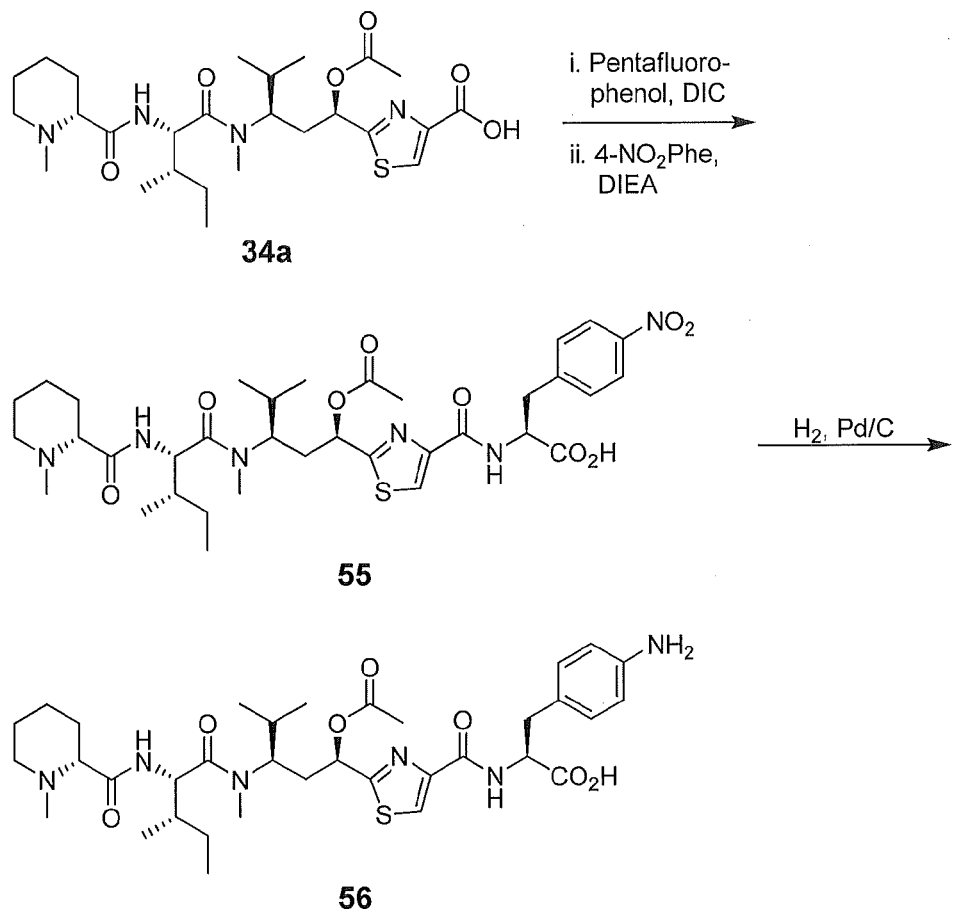

FIGS. 5, 6, and 7 depict Schemes 5, 6, and 7, respectively, for making compounds of this invention.

Figure 8A:
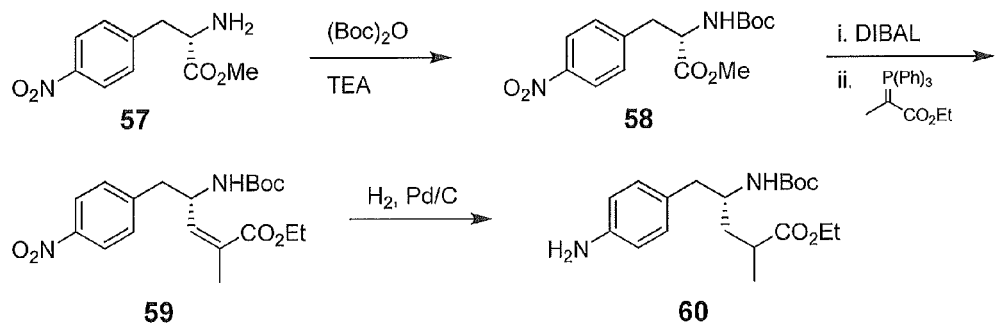
Figure 8B:
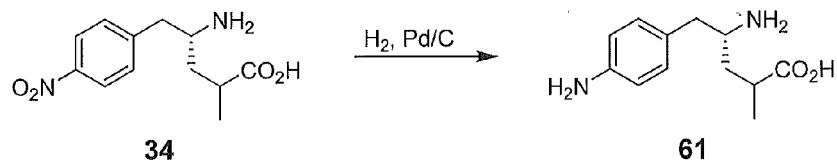
Figure 8C:
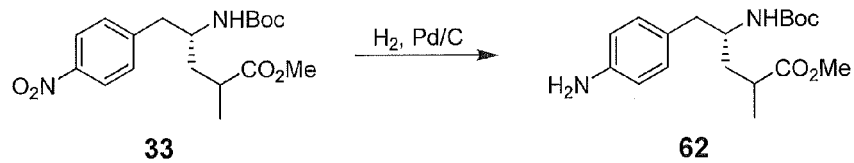

FIGS. 8a, 8b, and 8c show Schemes 8, 9, and 10, respectively, for making intermediates useful for preparing compounds of this invention.

Figure 9:
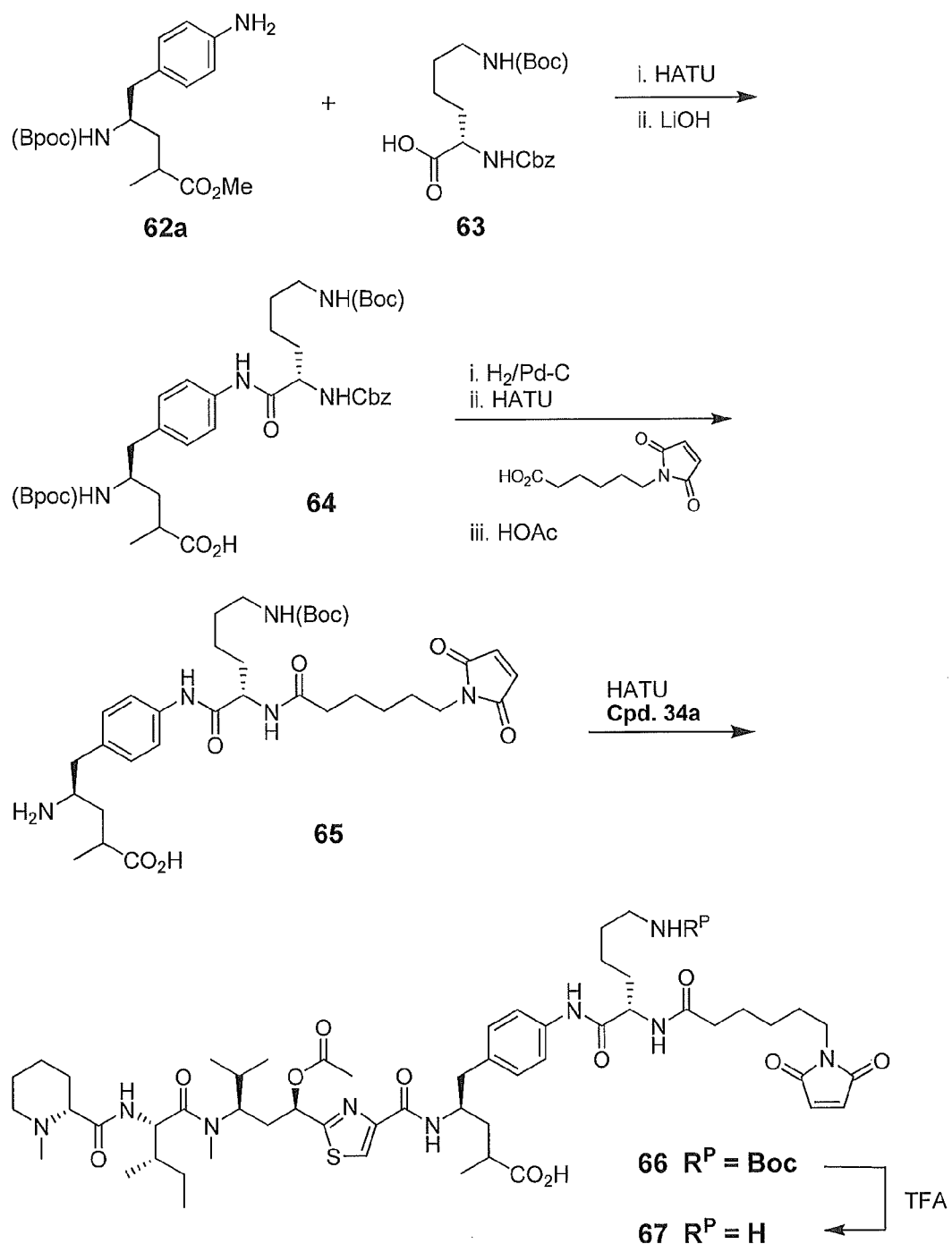
Figure 10:
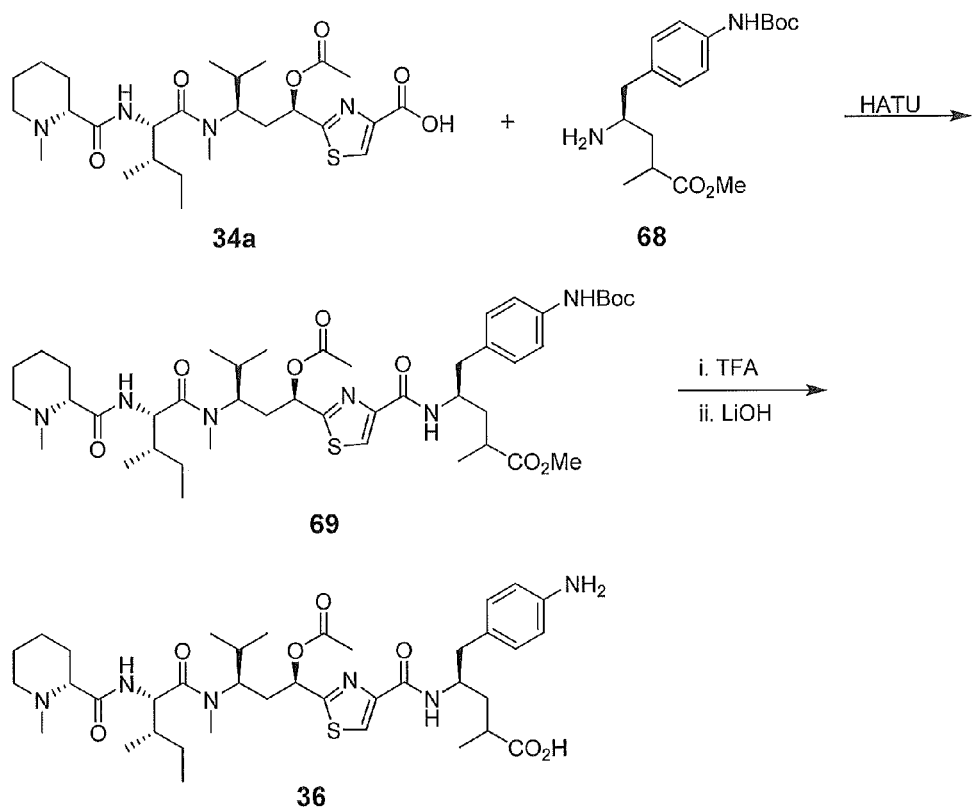

FIGS. 9 and 10 show Schemes 11 and 12, respectively, illustrating how intermediates such as those shown in FIGS. 8a-8c can be elaborated into compounds of this invention.

Figure 11A:
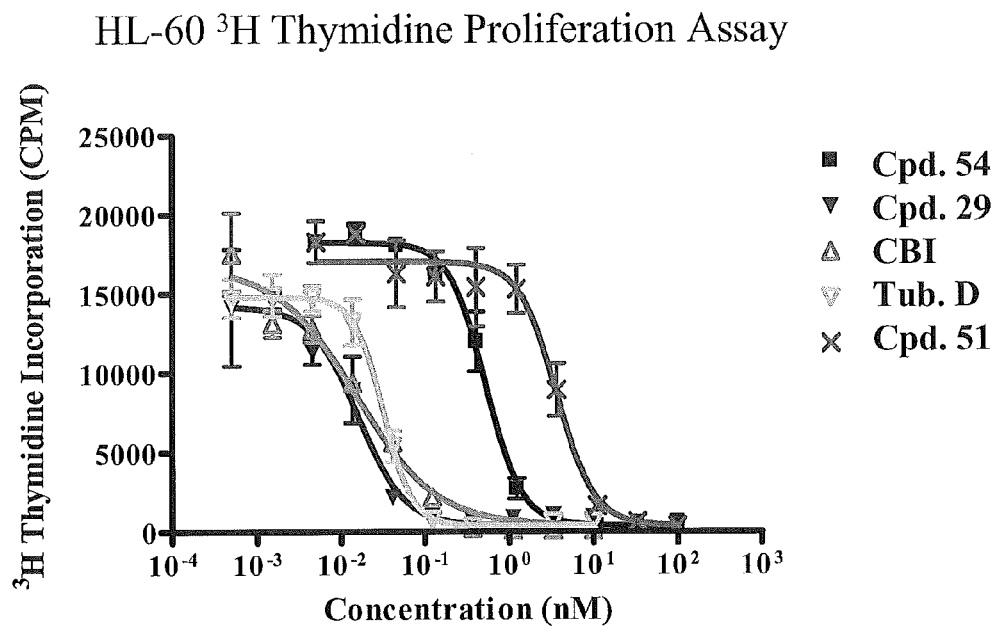
Figure 11B:
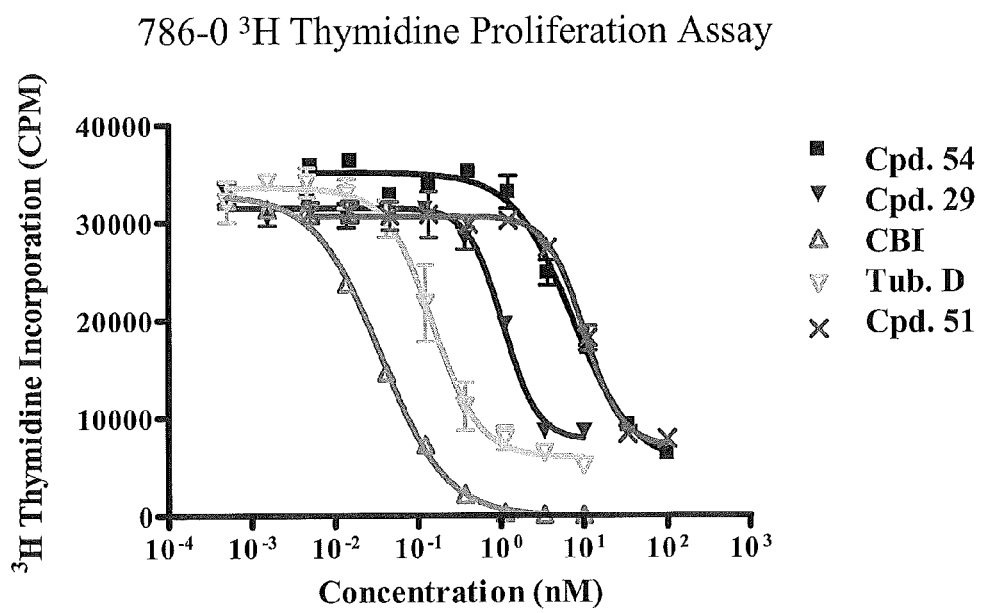

FIGS. 11a and 11b show the plots for $^3$H thymidine proliferation assays for a first set of compounds of this invention, against two different types of cancer cells.

Figure 12A:
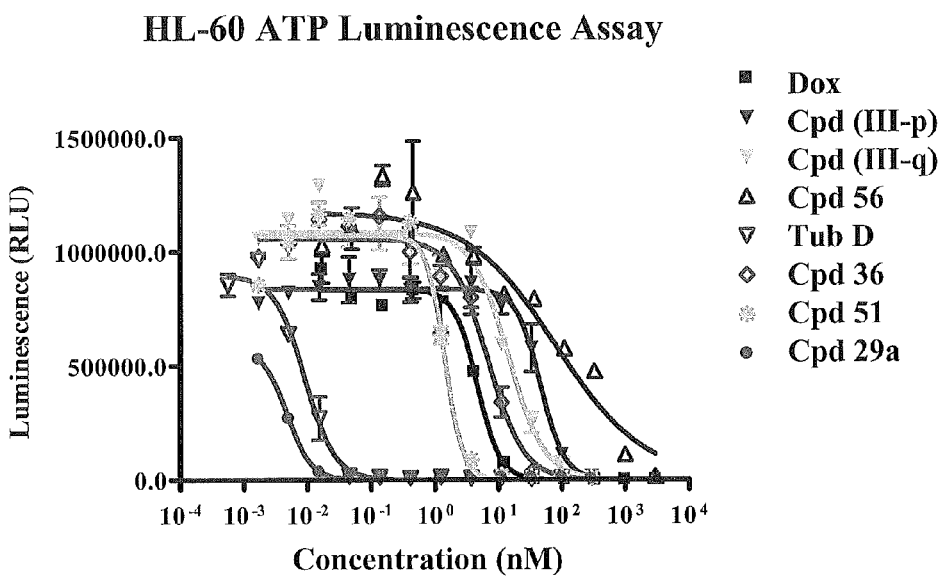
Figure 12B:
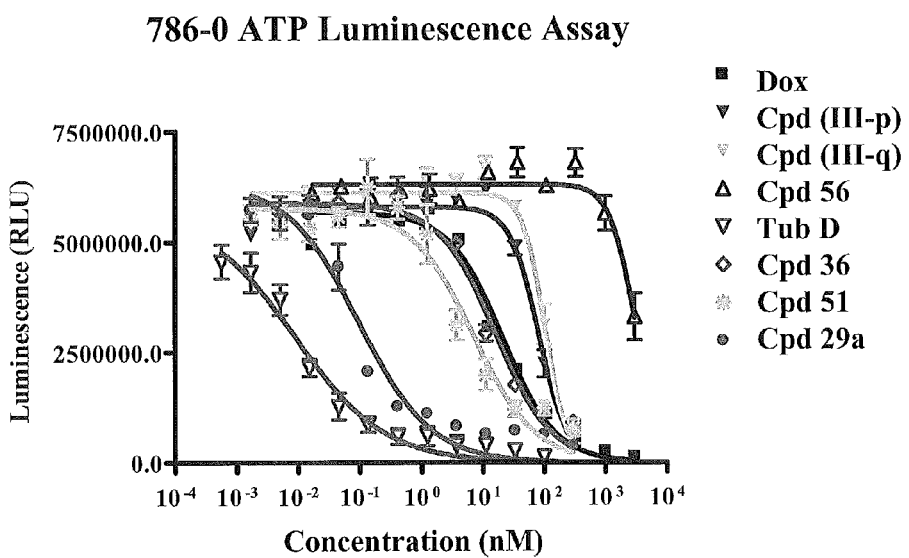
Figure 12C:
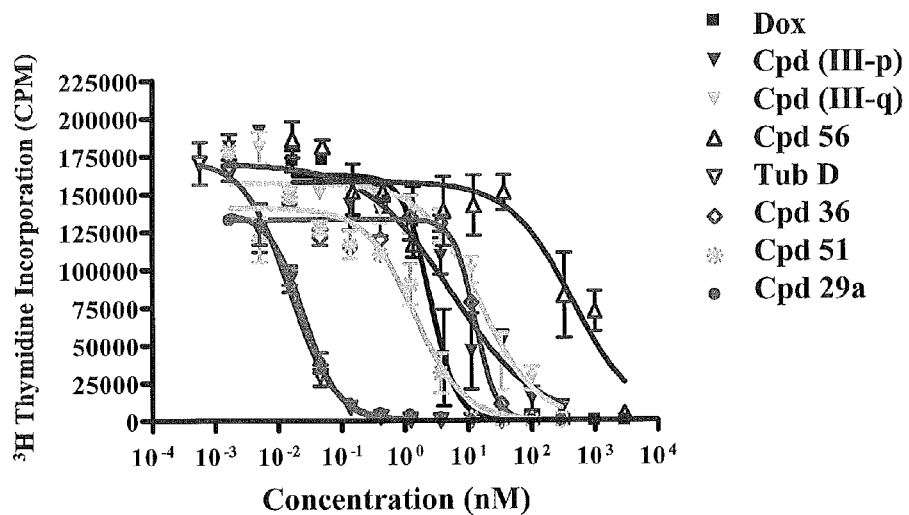
Figure 12D:
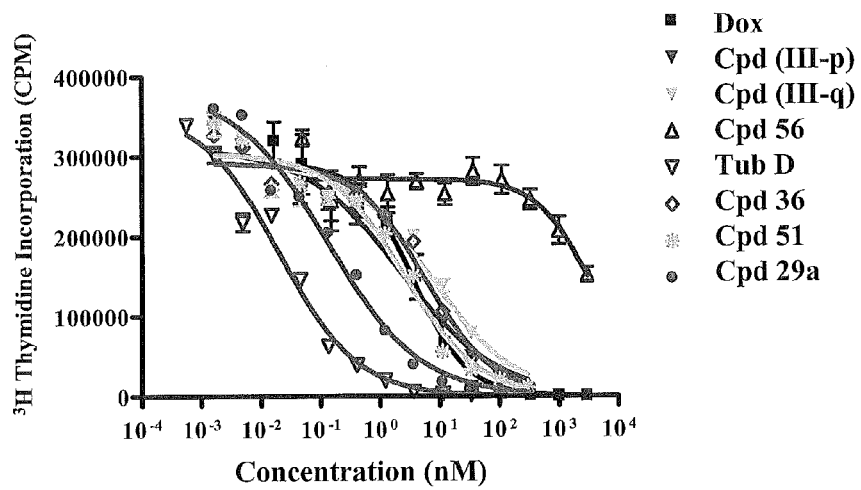

FIGS. 12a and 12b show the plots for ATP luminescence proliferation assays for a second set of compounds of this invention, against two different types of cancer cells. FIGS. 12c and 12d show the plots for $^3$H thymidine proliferation assays for the same second set of compounds and against the same two types of cancer cells.

Figure 13:
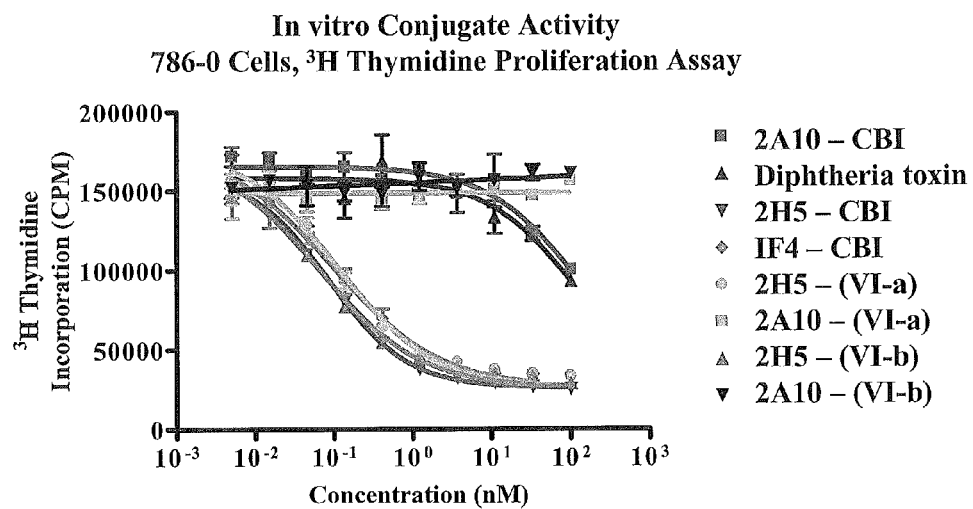

FIG. 13 shows the activity against renal cancer cells of conjugates of compounds of this invention in $^3$H thymidine proliferation assays.

Figure 14:
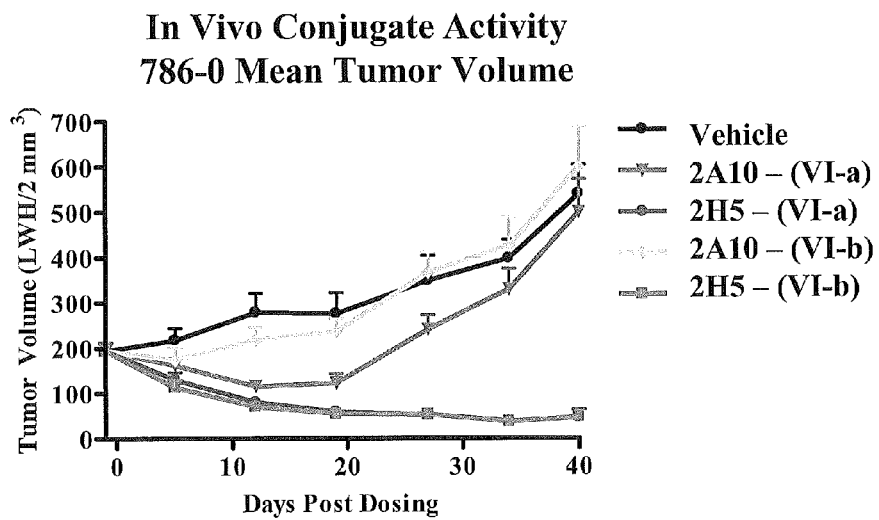

FIG. 14 shows the activity against renal cancer cells of conjugates of compounds of this invention in xenograft studies.

Figure 15:
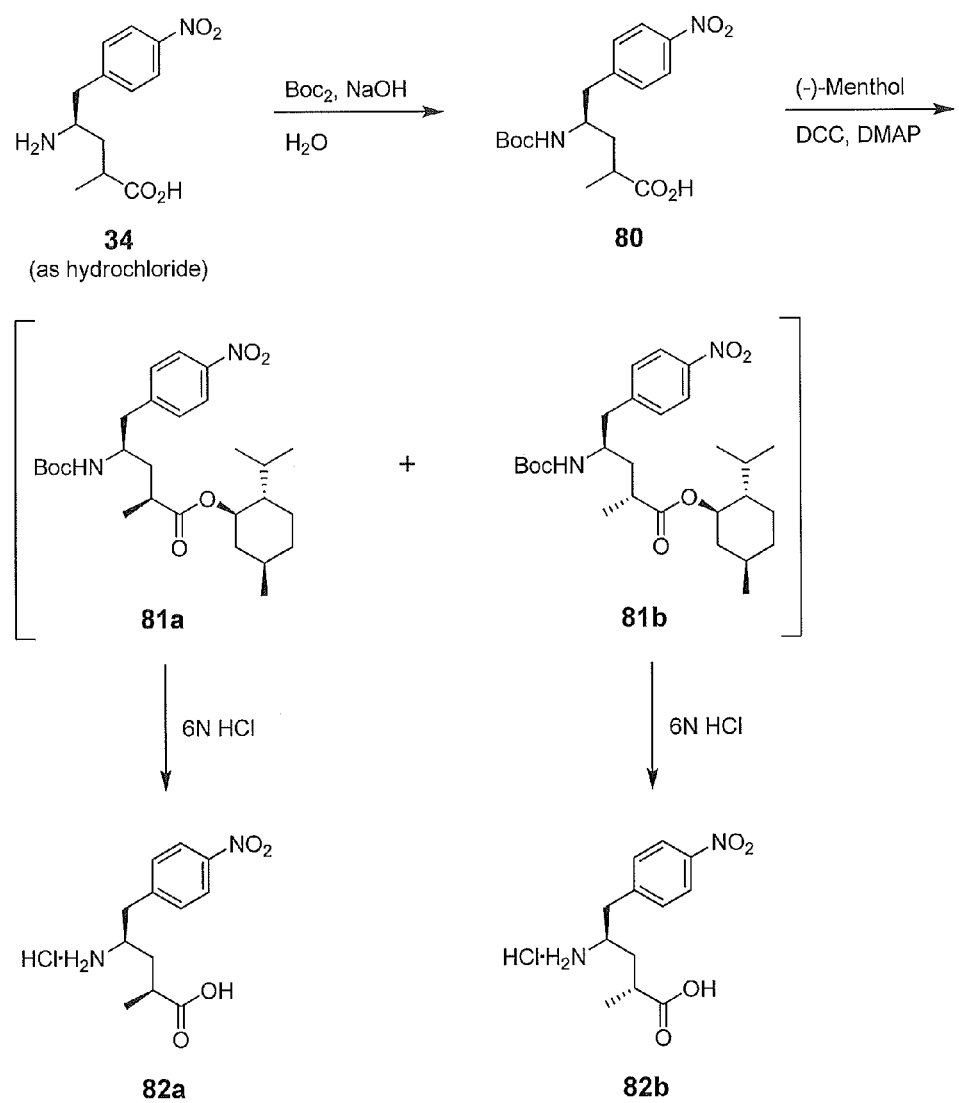

FIG. 15 shows a Scheme 13 for making intermediates useful for making compounds of this invention.

Figure 16:
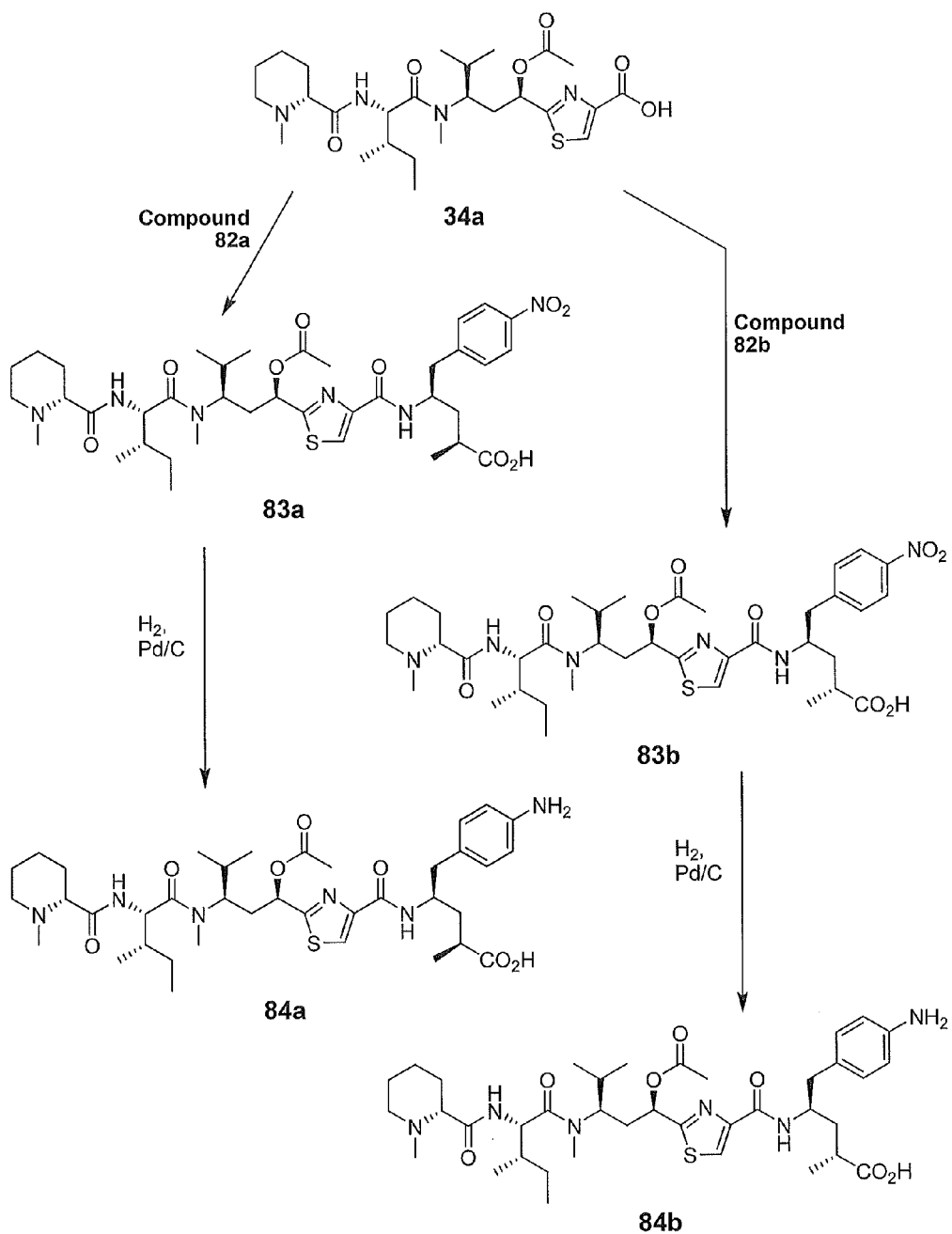

FIG. 16 shows a Scheme 14 for making compounds of this invention from intermediates made per Scheme 13.

Figure 17:
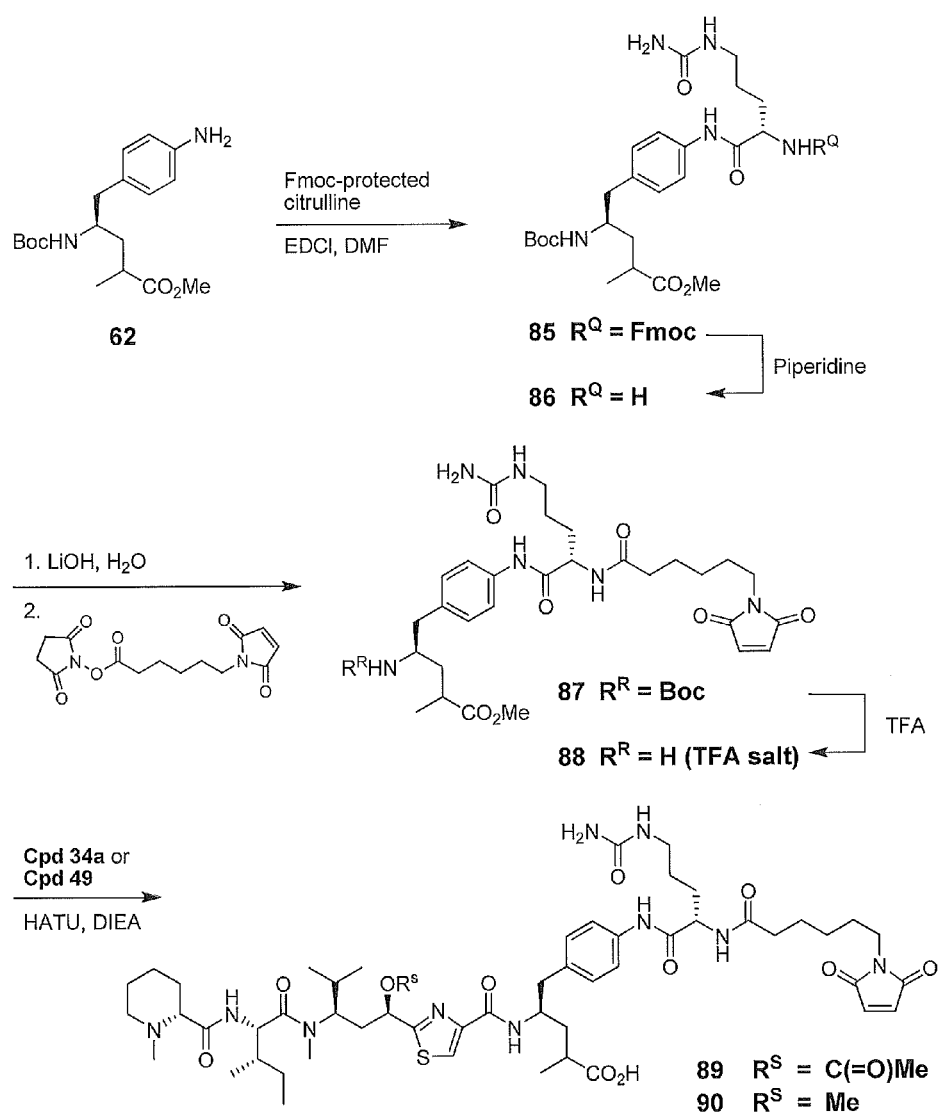
Figure 18:
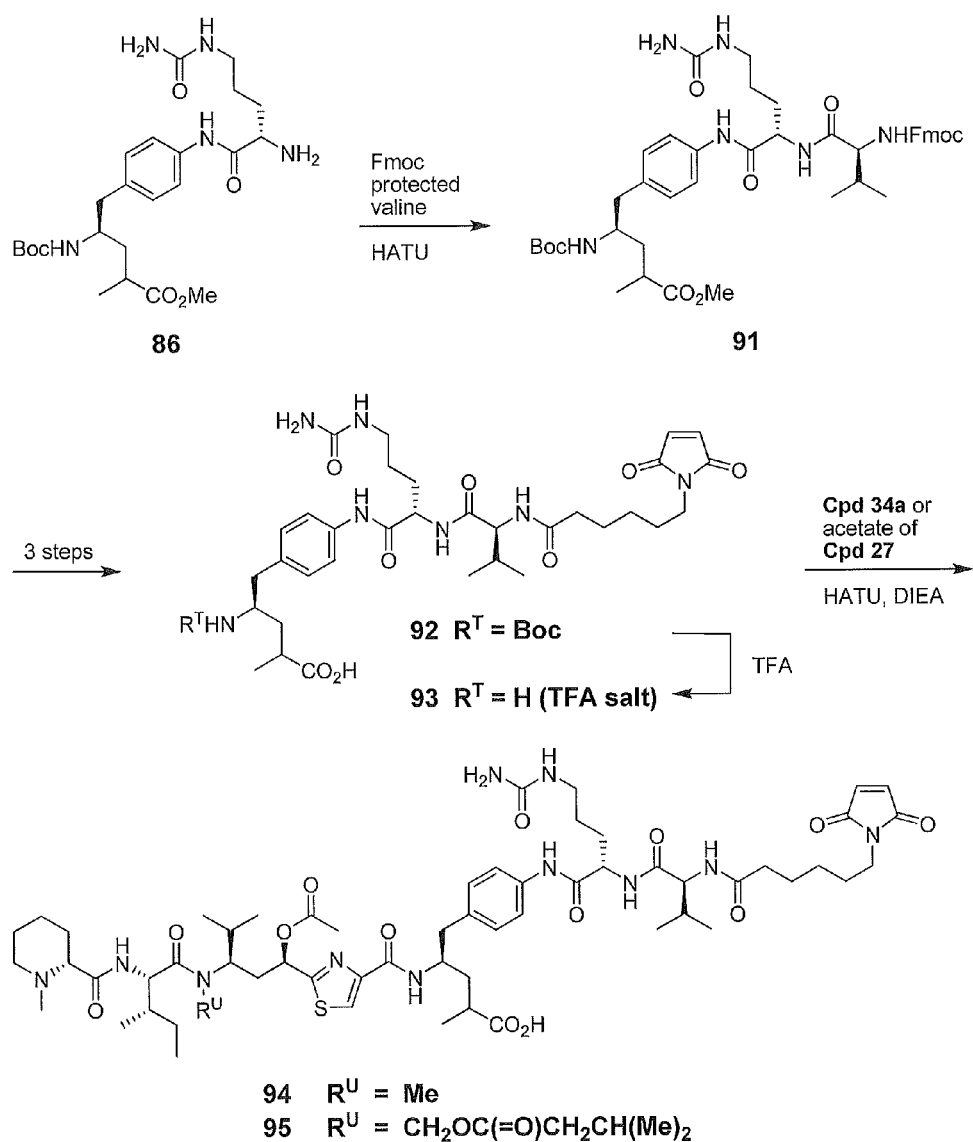

FIGS. 17 and 18 show Schemes 15 and 16, respectively, for making conjugation-ready compounds of this invention.

Figure 19:
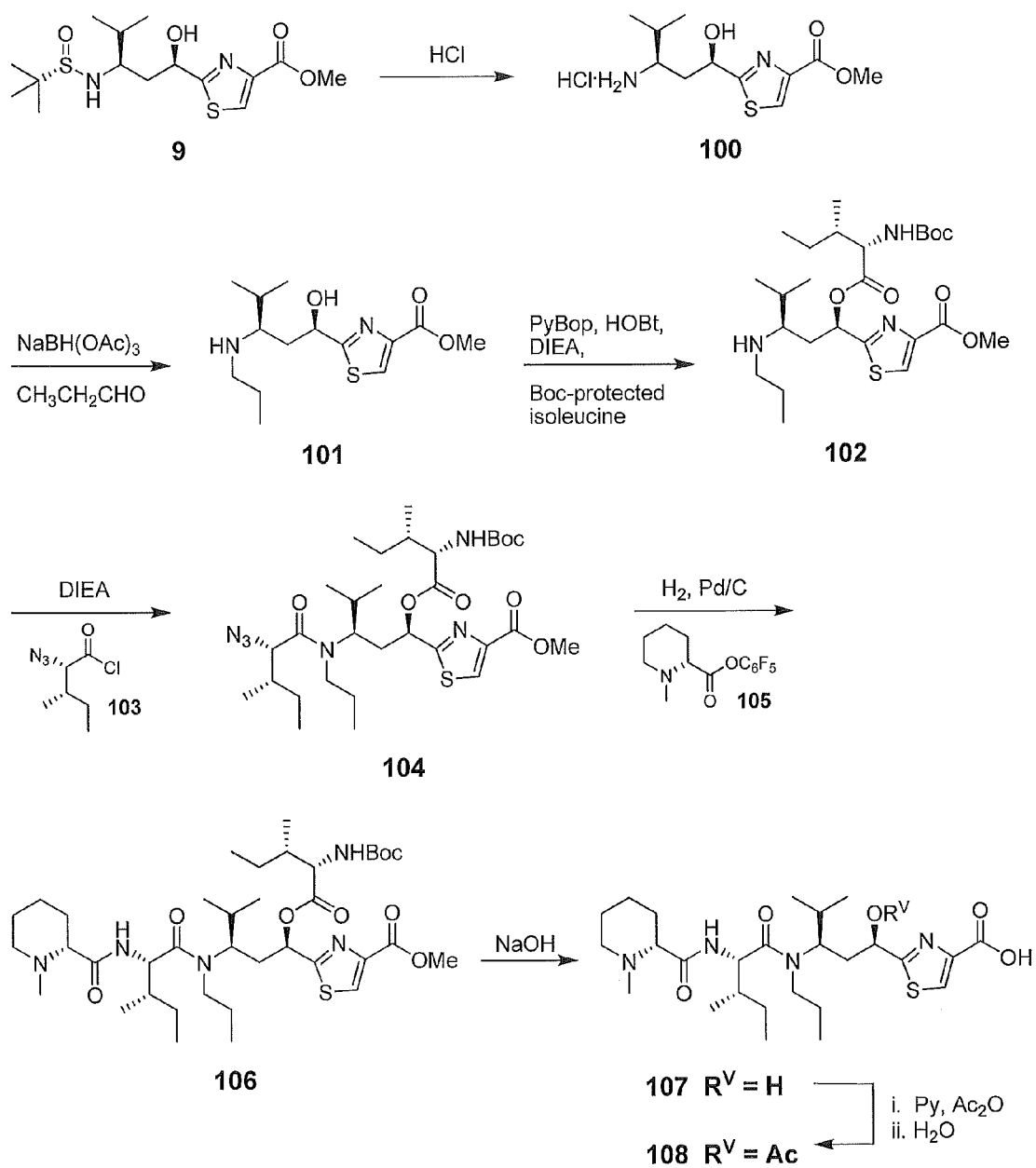

FIG. 19 shows Scheme 17 for making an intermediate useful for making compounds of this invention.

Figure 20A:
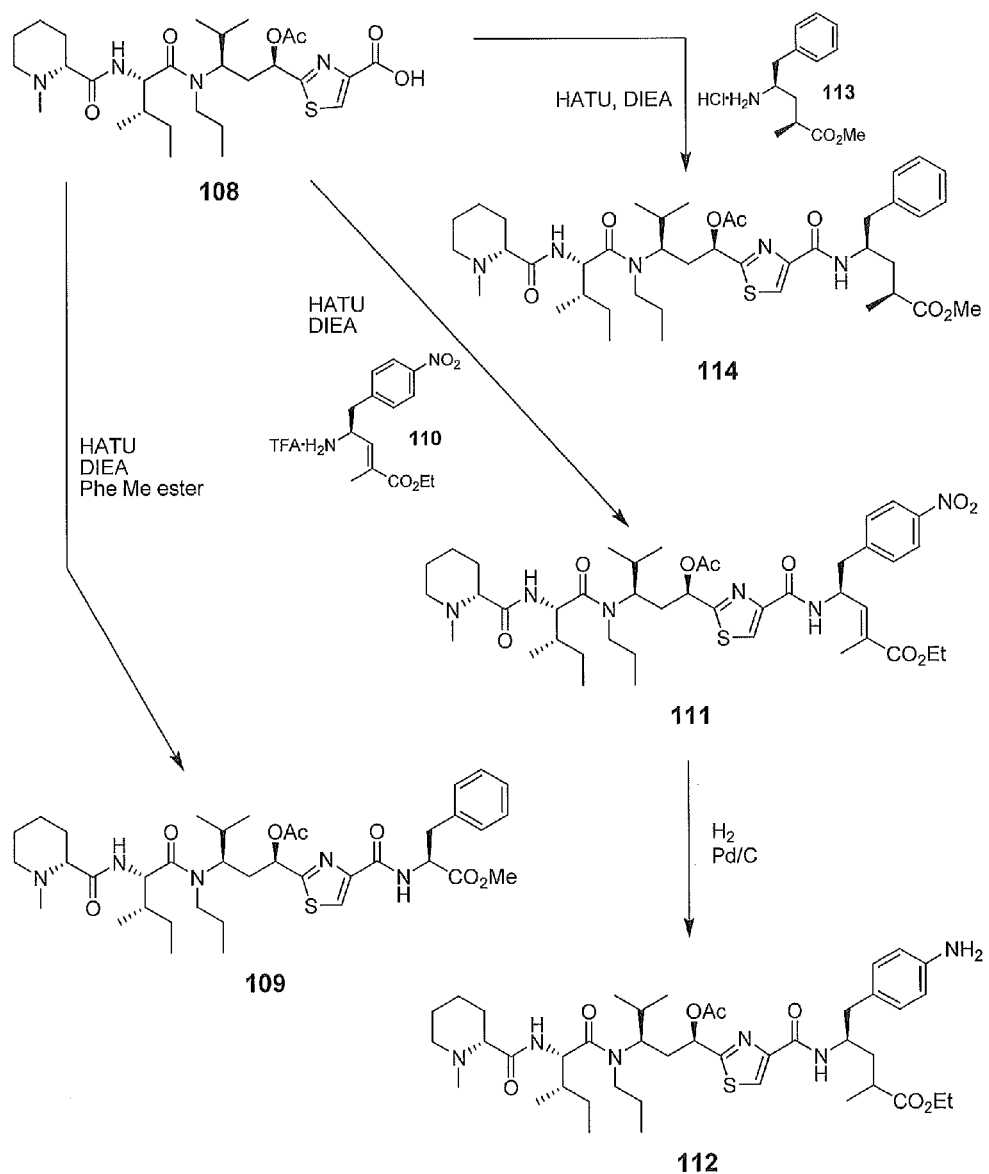
Figure 20B:
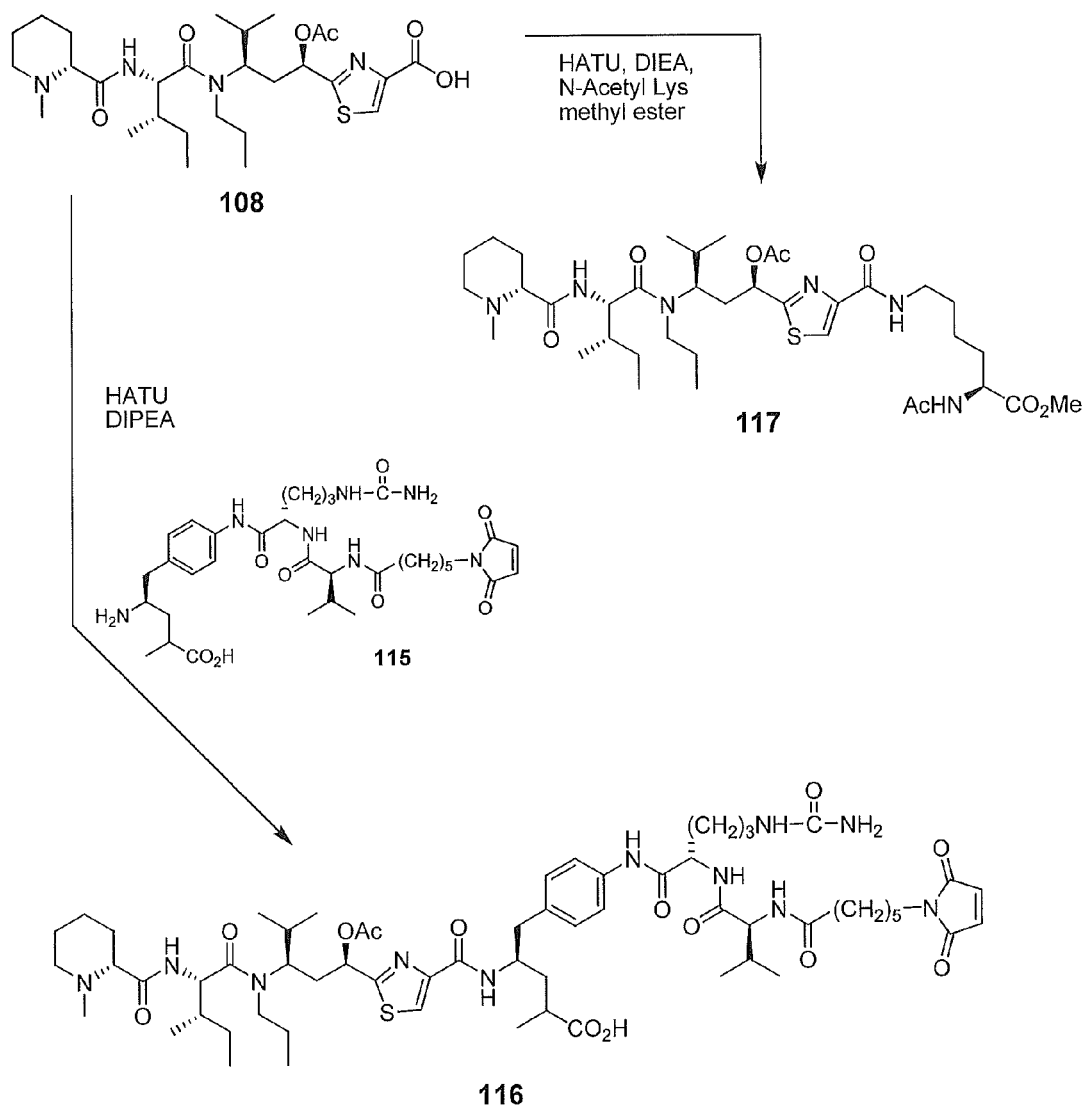

FIGS. 20a and 20b show in combination Scheme 18 for the preparation of compounds of this invention from the intermediate of Scheme 17.

Figure 21:
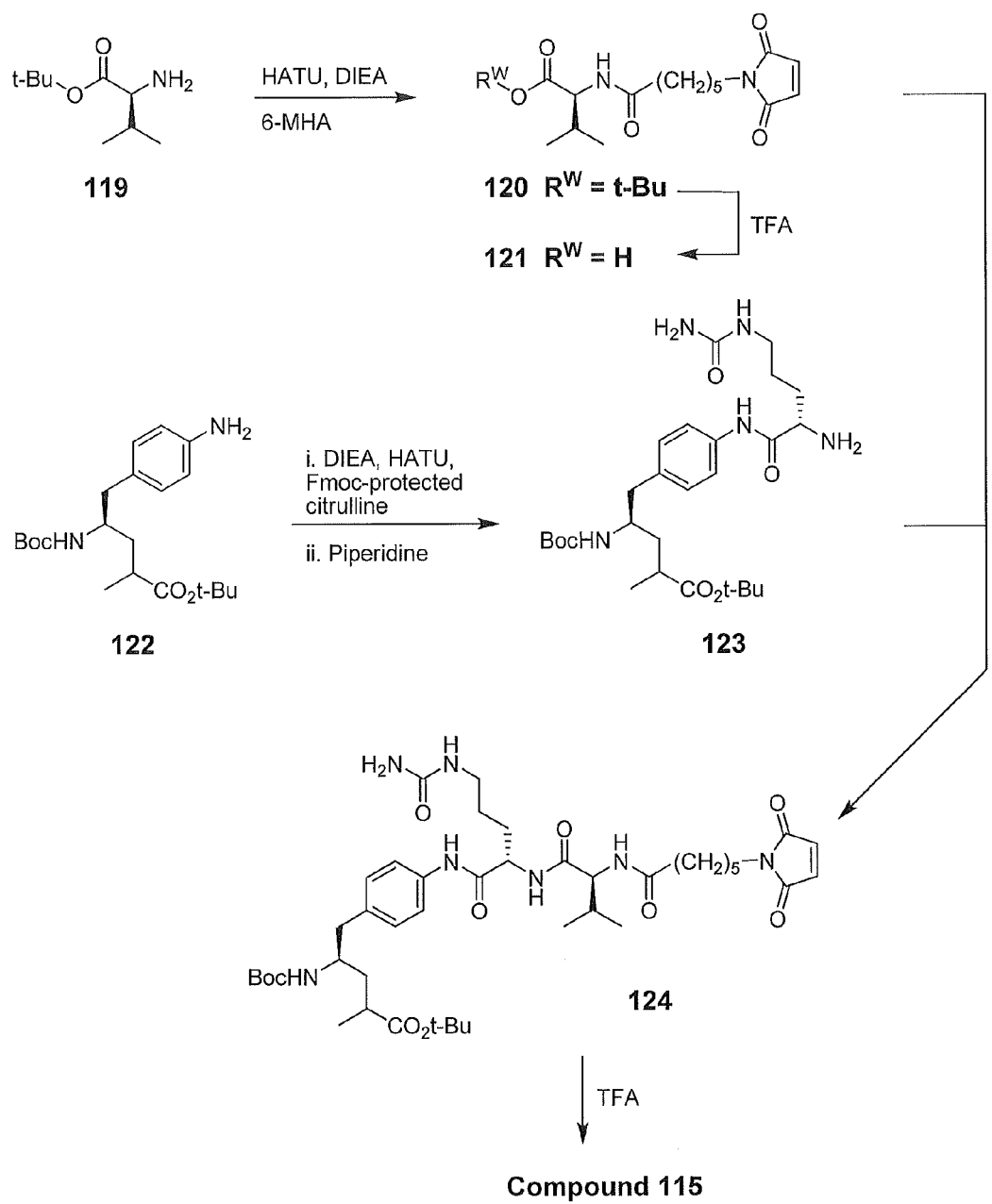

FIG. 21 shows Scheme 19 for making an intermediate used in Scheme 18.

Figure 22:
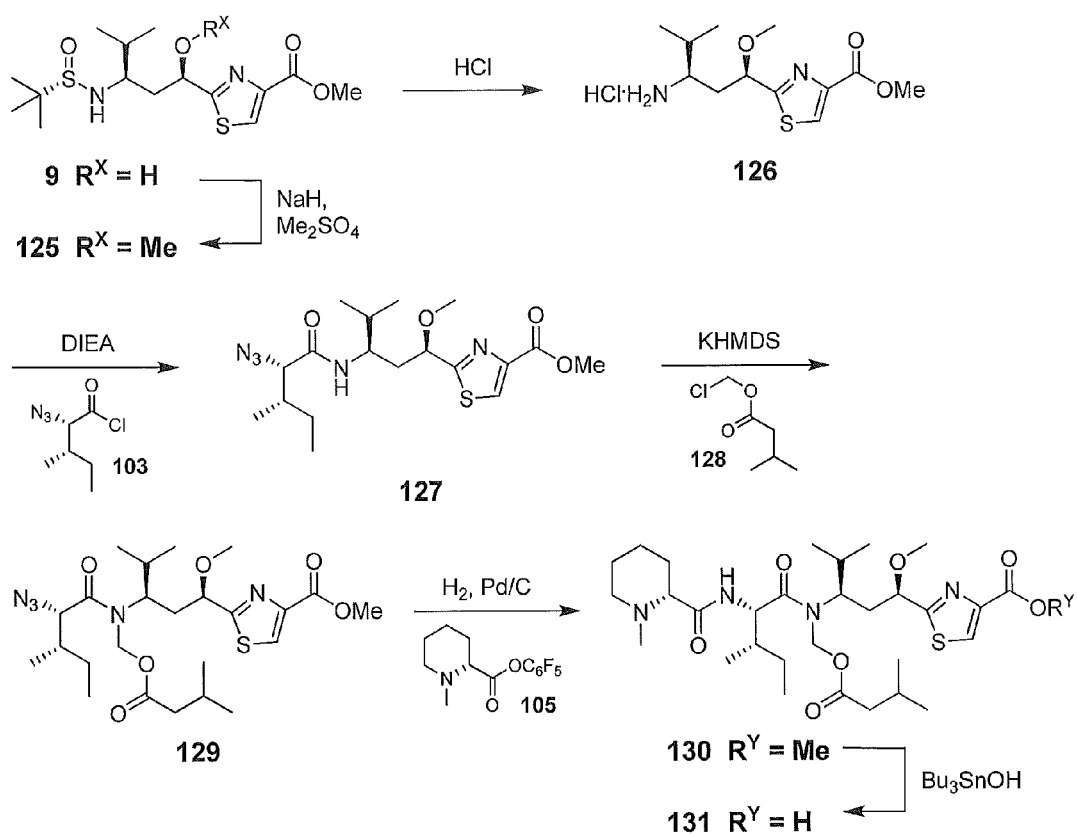

FIG. 22 shows Scheme 20 for the synthesis of an intermediate used in making compounds of this invention.

Figure 23:
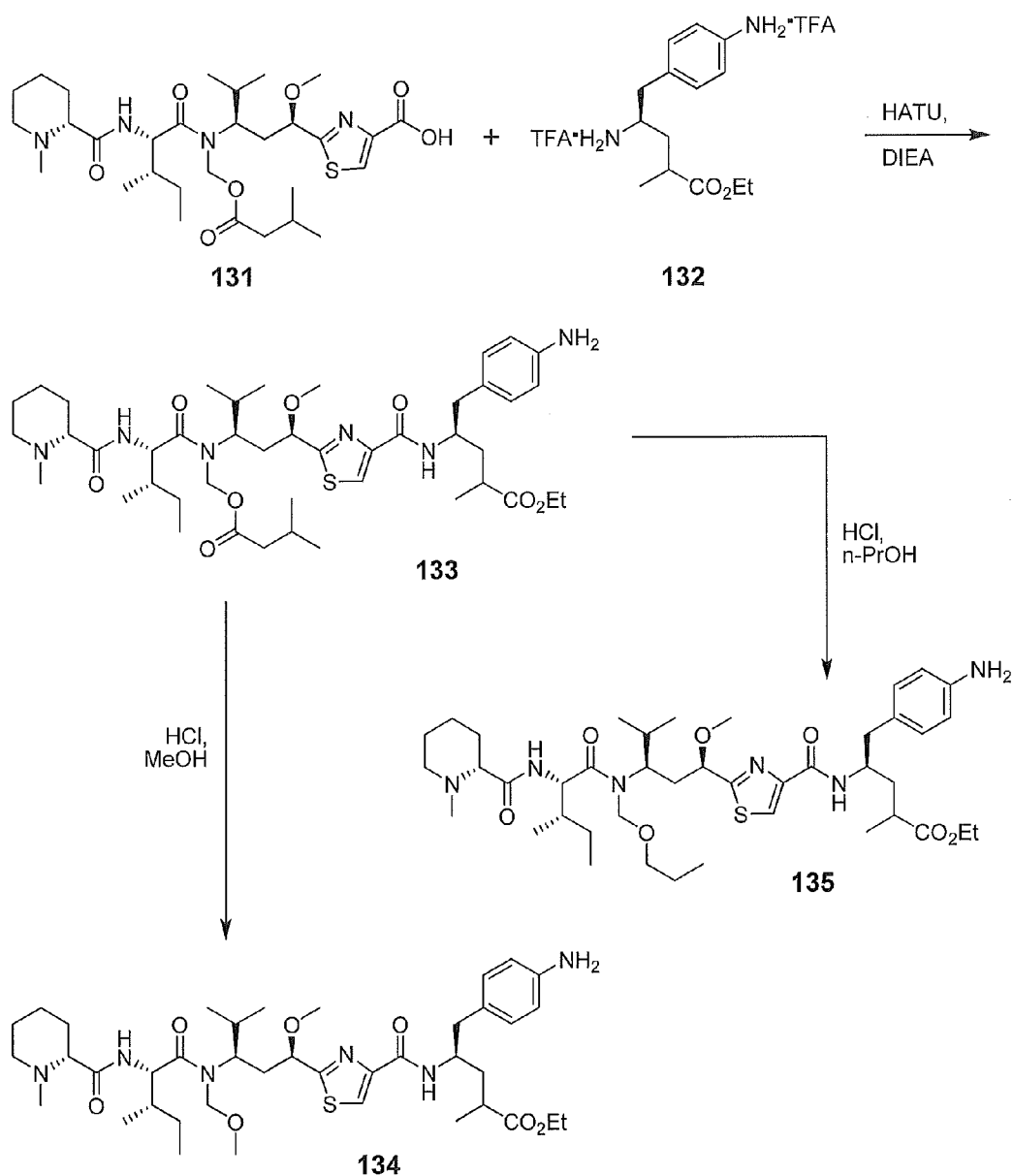

FIG. 23 shows Scheme 21 for making compounds of this invention from the intermediate of Scheme 20.

Figure 24:
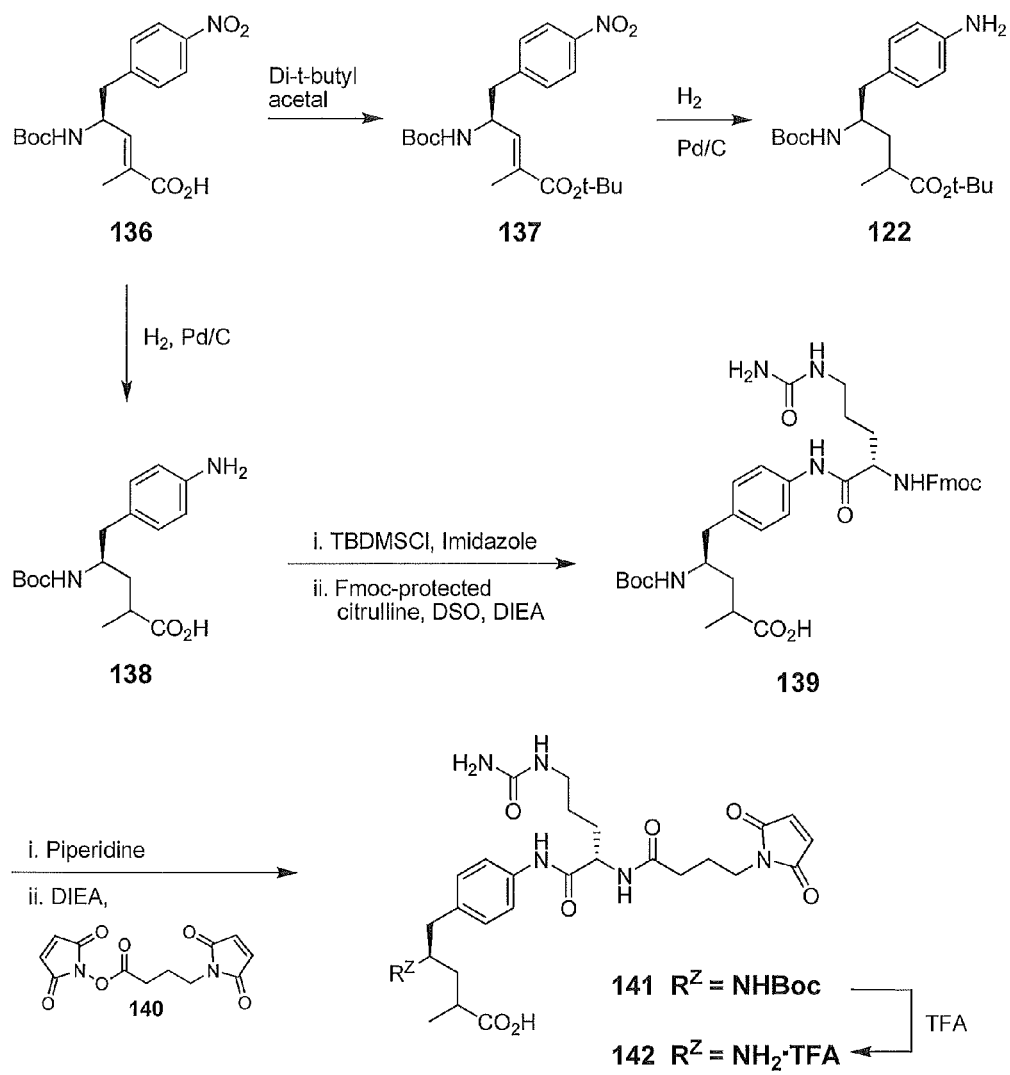

FIG. 24 shows the Scheme 22 for making yet another intermediate useful for making compounds of this invention.

Figure 25:
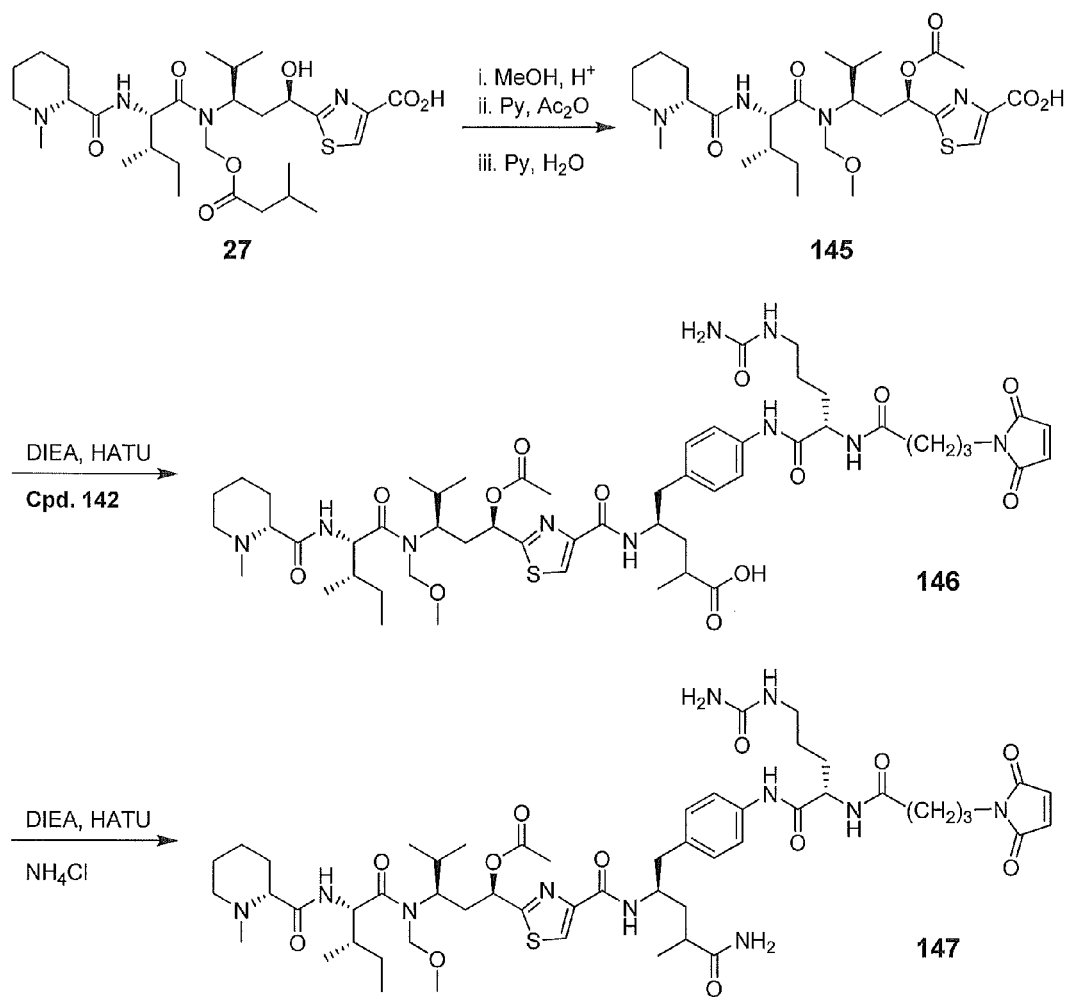

FIG. 25 shows Scheme 23 for making compounds of this invention from the intermediate of Scheme 22.

DETAILED DESCRIPTION OF THE INVENTION

Definitions

"Antibody" means whole antibodies and any antigen binding fragment (i.e., "antigen-binding portion") or single chains thereof. A whole antibody is a glycoprotein comprising at least two heavy (H) chains and two light (L) chains interconnected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5 \times 10^{-8}$ M or less, more preferably $1 \times 10^{-8}$ M or less, more preferably $6 \times 10^{-9}$ M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antibody fragment" and "antigen-binding portion" of an antibody (or simply "antibody portion") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementtarity determining region (CDR); and (viii) a nanobody, a heavy chain variable region containing a single variable domain and two constant domains. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242: 423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_1$-$C_5$ aliphatic," or "$C_1$ to $C_5$ aliphatic," the latter two phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties).

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like.

Where it is indicated that a moiety may be substituted, such as by use of "substituted or unsubstituted" or "optionally substituted" phrasing as in "substituted or unsubstituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

By way of illustration, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —NH(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$.

Where a range is stated, as in "$C_1$-$C_5$ alkyl" or "5 to 10%," such range includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

Compounds

A preferred embodiment of compounds of formula (II) is represented by formula (II-a)

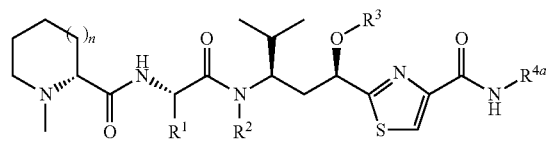

(II-a)

wherein n, $R^1$, $R^2$, and $R^3$ are as defined hereinabove in respect of formula (II) and $R^{4a}$ is

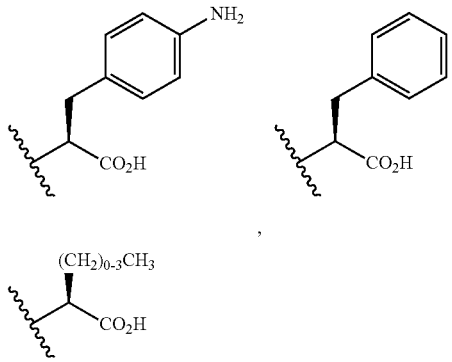

In the compounds of formula (II-a), the subunit corresponding to Tup/Tut in the naturally occurring tubulysins has been reduced in size and lipophilicity by at least two carbons, via deletion of the two aliphatic carbon atoms immediately following the carboxylic acid group—that is, the amino group is now α- to the carboxylic acid group, instead of γ- to it. In the instance in which $R^4$ is 4-aminophenylalanine, the amine group constitutes a polar moiety that further reduces lipophilicity. SAR studies show that lipophilicity is an important factor in the biological activity of the tubulysins and their analogs or derivatives. Steinmetz et al. 2004 and Neri et al. 2006 both disclose that the more lipophilic naturally occurring tubulysins—i.e., those having a Tup subunit ($R^A$ equals H in formula I) instead of a Tut subunit ($R^A$ equals OH in formula I)—possessed greater biological activity. Further, the differences in activities were retained regardless of the size and lipophilicity of the 11-acyloxy residue (group $R^C$ in formula (I)) in the Tuv subunit (Steinmetz et al. 2004). These results indicate that a lipophilic Tup/Tut subunit is a particularly important SAR element.

The above observations are partially corroborated in two studies by Balasubramanian et al. In the first (Balasubramanian et al. 2008), analogs dimethylated at the carbon alpha to the carboxyl group in the Tup subunit were compared against otherwise identical analogs desmethylated at the same position. The dimethylated analogs had greater antiproliferative activity—although the in vitro tubulin inhibition IC$_{50}$s were comparable—as might be expected based on their relative lipophilicities. However, this trend was not followed in the second study (Balasubramanian et al. 2009), in which three analogs (one α-carbon desmethylated, one monomethylated, and one dimethylated) were compared. There, the most active analog was the desmethylated one while the monomethylated one—i.e., with the natural Tup subunit—was by far the least active one. However, the latter analog had additional modifications elsewhere in the molecule rendering it essentially inactive, making it unclear what SAR inferences, if any, can be drawn.

Patterson et al. 2007 and Ellman et al. 2009 compared the cytotoxicities of tubulysin D and analogs in which either only the phenethyl or the γ-carboxy group was retained in the Tup subunit. The phenethyl-retained analog was 3.6 to 13.6 times less active than tubulysin D against three cancer cell lines but when the less lipophilic γ-carboxyl group was retained, there was an even greater loss of activity, from 25.7 to 62.5 times less active. That is, the order of activity was:

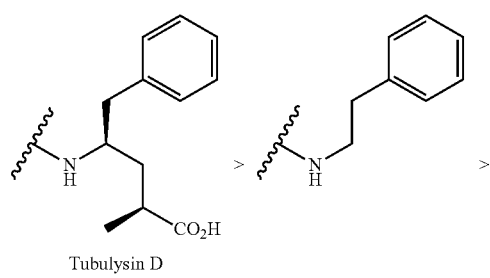

Tubulysin D

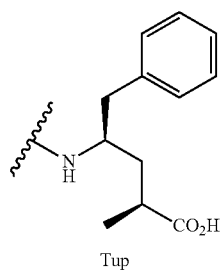

Tup

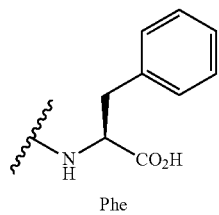

Phe

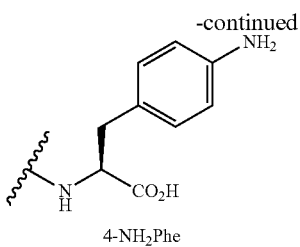

4-NH₂Phe

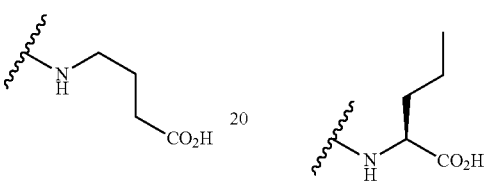

Norvaline

The above documents suggest, individually and in combination, that lipophilicity at the Tup locus is especially important for the biological activity of the tubulysins. Therefore, the prior art suggests that the replacement of the Tup subunit with a phenylalanine (Phe), 4-aminophenylalanine (4-NH₂Phe), norvaline or other $R^4$ subunit in accordance with formula (II-a) is undesirable, as each would lead to the loss of at least two aliphatic carbons and a consequent reduction in lipophilicity at the Tup/Tut locus.

Another preferred embodiment of compounds of formula (II) is represented by formula (II-b):

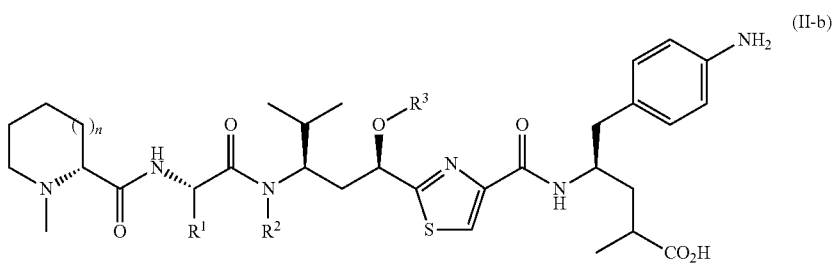

(II-b)

wherein n, $R^1$, $R^2$, and $R^3$ are as defined hereinabove in respect for formula (II). Although chemical formulae can be found in the literature encompassing an —NH₂ group in the 4-position of the Tup aromatic ring (Domling 2005a and 2005b), there has been no disclosure on how a compound having such a feature might be made.

In formulae (II), (II-a), and (II-b), $R^1$ preferably is H, $C_1$-$C_5$ alkyl, $C_2$-$C_5$ alkenyl, or $C_2$-$C_5$ alkenyl, and is more preferably an isoleucyl residue, that is:

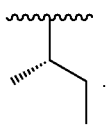

In formulae (II), (II-a), and (II-b), $R^2$ preferably is H, $C_1$-$C_5$ alkyl, $C_2$-$C_5$ alkenyl, CH₂O($C_1$-$C_5$ alkyl), CH₂O($C_2$-$C_5$ alkenyl), CH₂O(C=O)($C_1$-$C_5$ alkyl), or CH₂OC(=O)($C_2$-$C_5$ alkenyl); and more preferably is H, Me, Et, n-Pr, CH₂OMe, CH₂OEt, CH₂O(n-Pr), CH₂OC(=O)i-Bu, CH₂OC(=O)n-Pr, CH₂OC(=O)CH=CH₂, or CH₂OC(=O)Me, with Me, n-Pr, CH₂OMe, CH₂OC(=O)i-Bu, and CH₂O(n-Pr) being especially preferred.

In formulae (II), (II-a), and (II-b), $R^3$ preferably is H, $C_1$-$C_5$ alkyl, $C_2$-$C_5$ alkenyl, C(=O)$C_1$-$C_5$ alkyl, or C(=O)$C_2$-$C_5$ alkenyl; and more preferably is H, Me, Et, or C(=O)Me.

Preferably, in formulae (II) and (II-a), $R^4$ and $R^{4a}$ are:

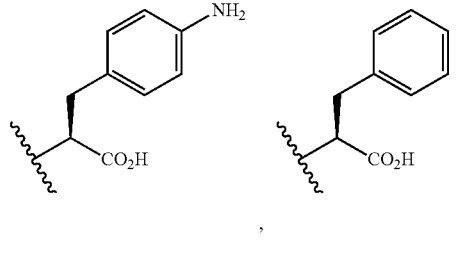

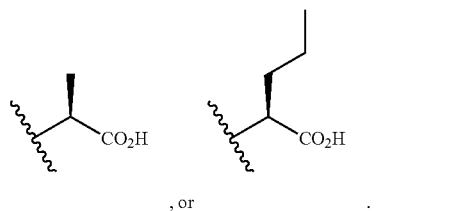

, or .

In formulae (II), (II-a), and (II-b), n preferably is 1 and, in the instance of formula (II), $R^5$ preferably is methyl; that is, the ring in the Mep subunit preferably is an N-methyl piperidinyl one.

A preferred embodiment of compounds according to formula (II-a) is depicted by formula (II-a')

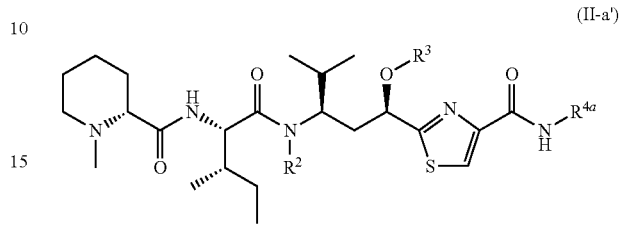

where $R^{4a}$ is as defined above in respect of formula (II-a), $R^2$ is H, $C_1$-$C_5$ alkyl, $C_2$-$C_5$ alkenyl, $CH_2O(C_1$-$C_5$ alkyl), $CH_2O(C_2$-$C_5$ alkenyl), $CH_2O(C=O)(C_1$-$C_5$ alkyl), or $CH_2OC(=O)(C_2$-$C_5$ alkenyl); and $R^3$ is H, $C_1$-$C_5$ alkyl, $C_2$-$C_5$ alkenyl, C(=O)$C_1$-$C_5$ alkyl, or C(=O)$C_2$-$C_5$ alkenyl. Preferably, $R^2$ is H, Me, Et, n-Pr, $CH_2$OMe, $CH_2$OEt, $CH_2$OC(=O)i-Bu, $CH_2$OC(=O)n-Pr, $CH_2$OC(=O)CH=$CH_2$, or $CH_2$OC(=O)Me; more preferably Me, n-Pr, $CH_2$OMe, $CH_2$OC(=O)i-Bu, or $CH_2$O(n-Pr). Preferably, $R^3$ is H, Me, Et, or C(=O)Me.

A preferred embodiment of compounds according to formula (II-b) is depicted by formula (II-b')

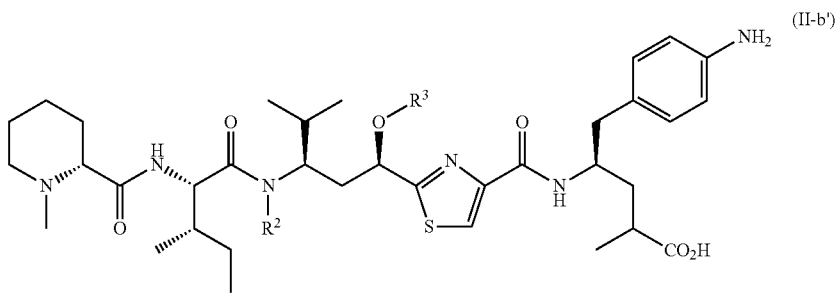

where $R^2$ is H, $C_1$-$C_5$ alkyl, $C_2$-$C_5$ alkenyl, $CH_2O(C_1$-$C_5$ alkyl), $CH_2O(C_2$-$C_5$ alkenyl), $CH_2O(C=O)(C_1$-$C_5$ alkyl), or $CH_2OC(=O)(C_2$-$C_5$ alkenyl); and $R^3$ is H, $C_1$-$C_5$ alkyl, $C_2$-$C_5$ alkenyl, C(=O)$C_1$-$C_5$ alkyl, or C(=O)$C_2$-$C_5$ alkenyl. Preferably, $R^2$ is H, Me, Et, n-Pr, $CH_2$OMe, $CH_2$OEt, $CH_2$OC(=O)i-Bu, $CH_2$OC(=O)n-Pr, $CH_2$OC(=O)CH=$CH_2$, or $CH_2$OC(=O)Me and $R^3$ is H, Me, Et, or C(=O)Me.

Where a carboxyl group in $R^4$ is esterified, preferably the ester is a $C_1$-$C_5$ alkyl ester, such as a Me, Et, or Pr ester. Alternatively, the carboxyl group can be amidated with ammonia or an alkyl amine In another embodiment, this invention provides a compound having a structure represented by formula (II-c)

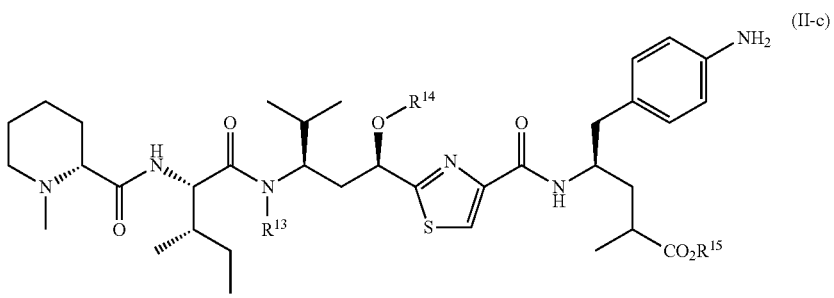
(II-c)

where $R^{13}$ is Me, n-Pr, $CH_2OMe$, or $CH_2OC(=O)CH_2CH(Me)_2$; $R^{14}$ is Me or $C(=O)Me$; and $R^{15}$ is H or $C_1$-$C_5$ alkyl (preferably H, Me, or Et).

In formulae (II-b), (II-b'), and (II-c) the stereochemistry at the methyl alpha to the carboxyl preferably is that corresponding to the naturally-occurring tubulysins, i.e.:

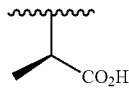

In a preferred embodiment, a compound of this invention is in the form of an amide of the carboxyl group in $R^4$ (or $R^{4a}$, as the case may be) with the α-amine group of an α-amino acid. The α-amino acid can be selected from the group consisting of a proteinogenic amino acid, 4-aminophenylalanine, norvaline, norleucine, and citrulline. Preferably, the α-amino acid is selected from the group consisting of alanine, norvaline, glycine, lysine, arginine, citrulline, norleucine, 4-aminophenylalanine, and phenylalanine. Also preferably, the absolute configuration of the α-amino acid is the proteinogenic one, i.e., L. In this preferred embodiment, $R^4$ (or $R^{4a}$) preferably is:

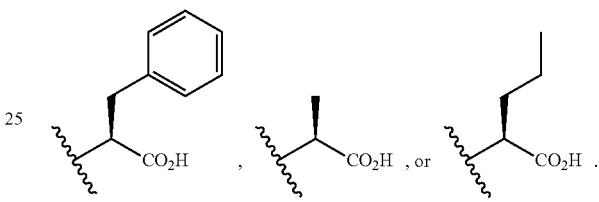

Specific examples of compounds of this invention according to formula (II) include compounds (III-a) through (III-y). Some of the compounds are depicted as a pharmaceutically acceptable ester or a pharmaceutically acceptable amide of the $R^4$ carboxyl group with the α-amine group of an α-amino acid or methyl ester thereof

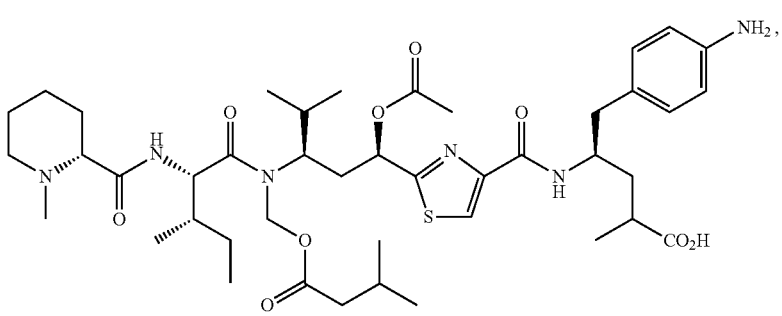
(III-a)

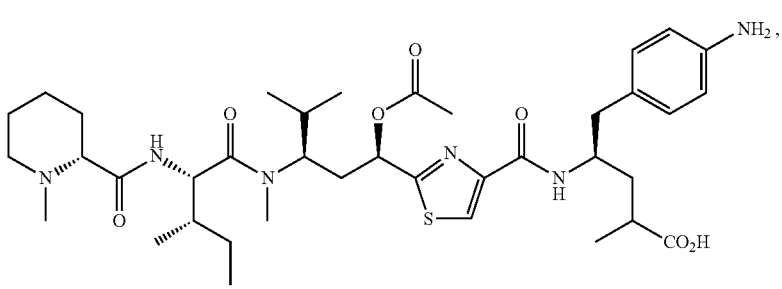
(III-b)

-continued
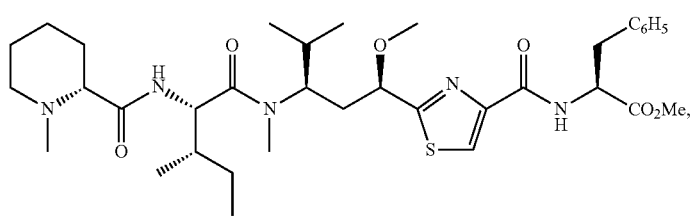
(III-c)
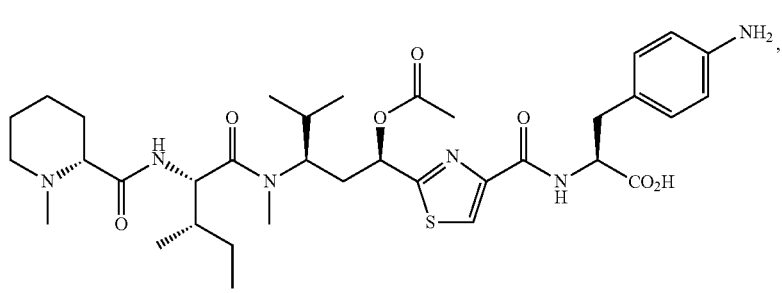
(III-d)
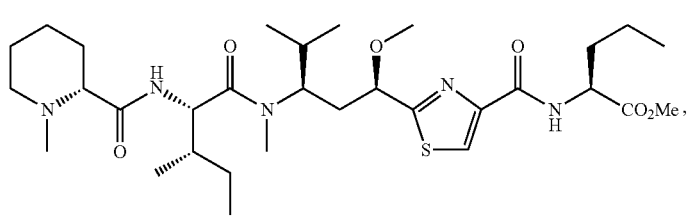
(III-e)
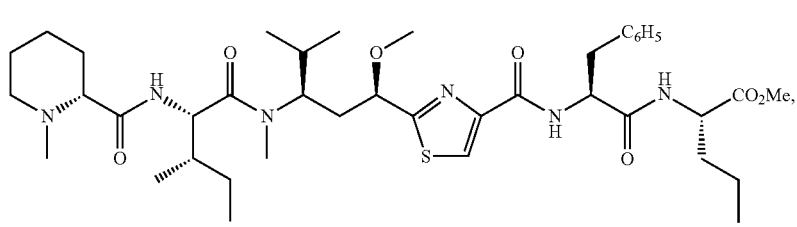
(III-f)
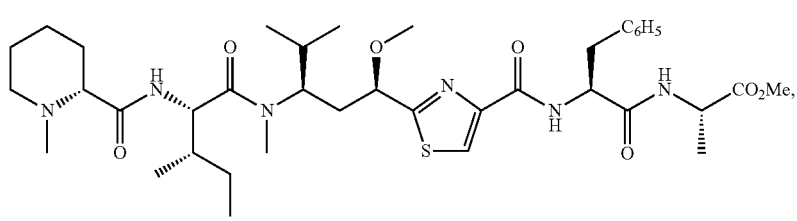
(III-g)
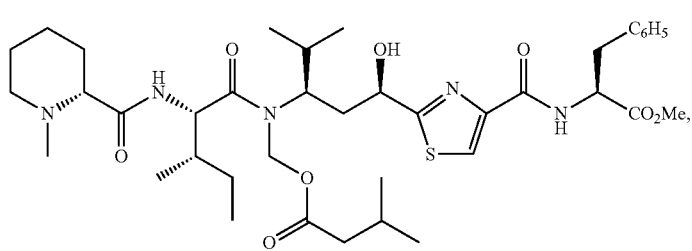
(III-h)

(III-i)
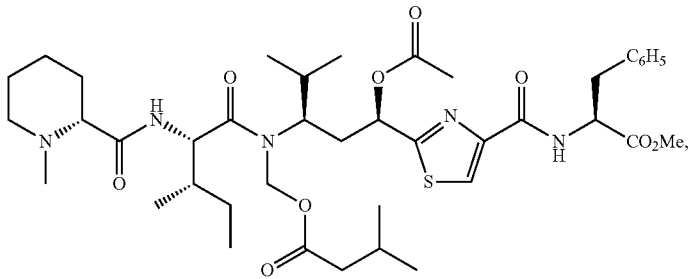
(III-j)
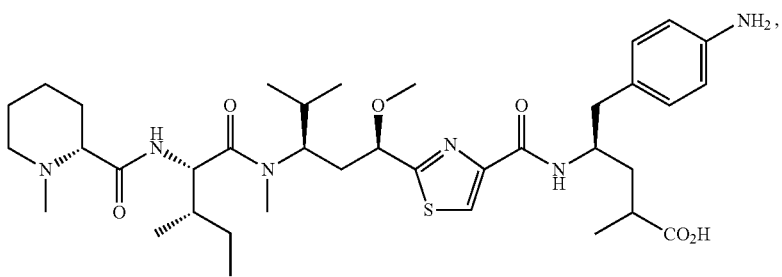
(III-k)
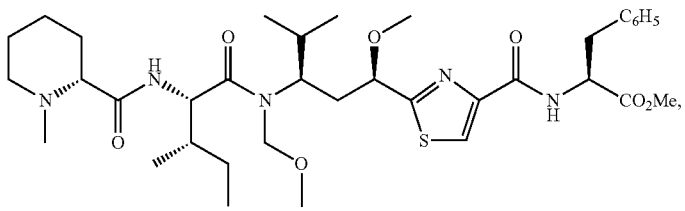
(III-l)
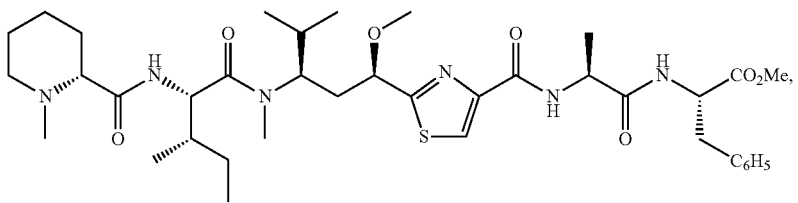
(III-m)
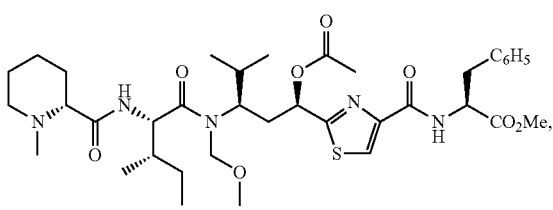
(III-n)
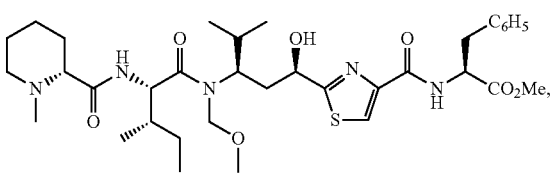
(III-o)
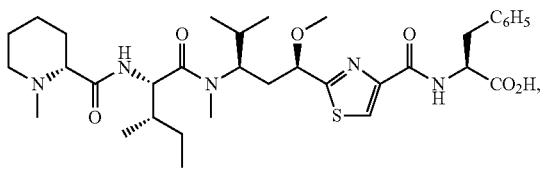
(III-p)
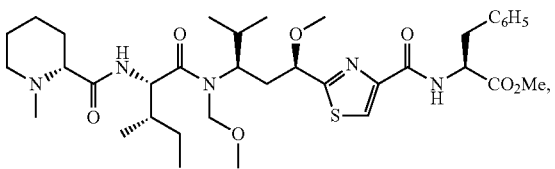

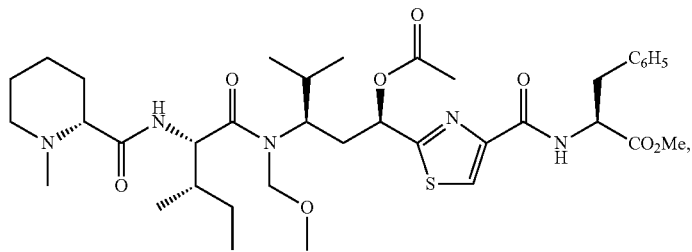
(III-q)
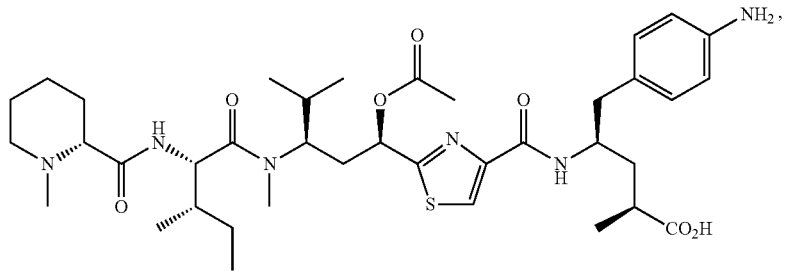
(III-r)
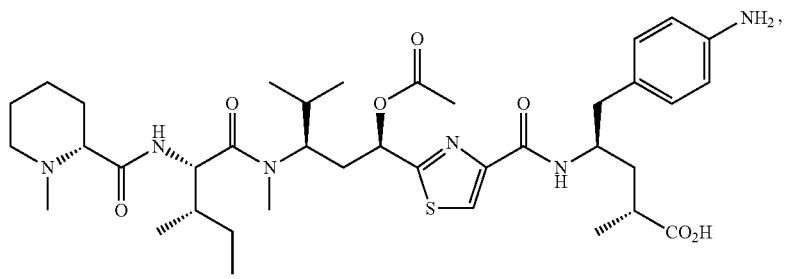
(III-s)
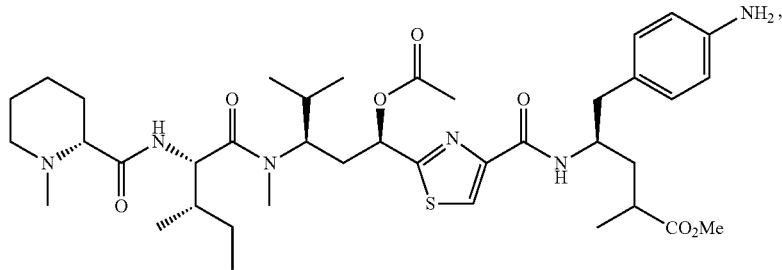
(III-t)
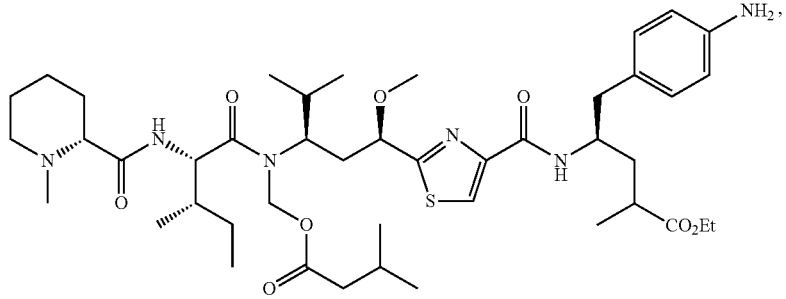
(III-u)

-continued
(III-v)
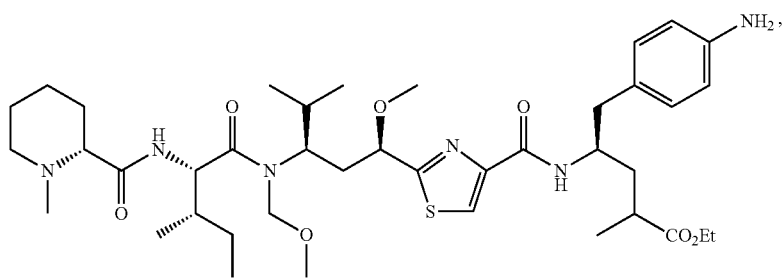
(III-w)
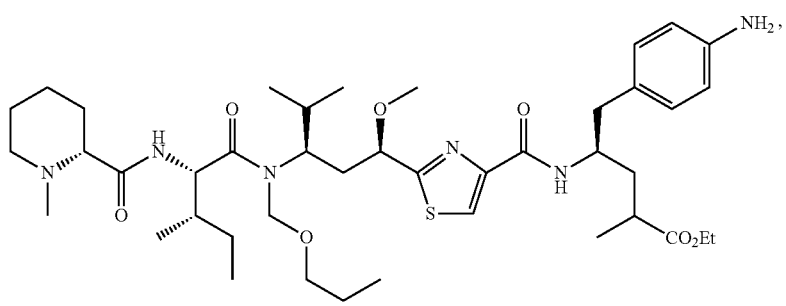
(III-x)
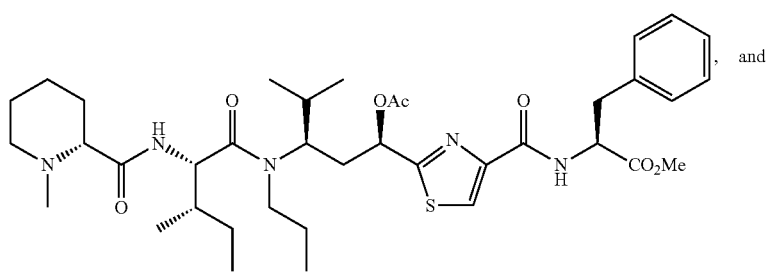
, and
(III-y)
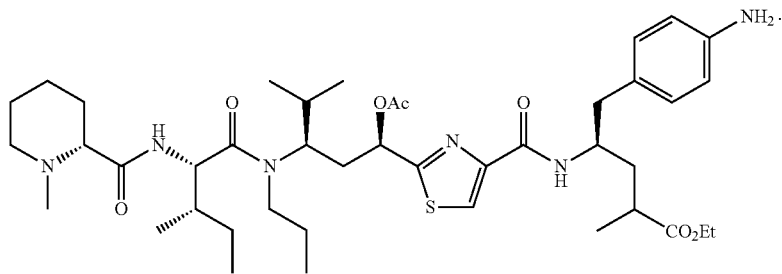

This invention also provides novel intermediates that can be utilized for the synthesis of compounds of this invention. Compounds according to formula (VIII-a) can be used for the making of compounds according to formula (II) or (II-b), as taught in the figures and examples herein.

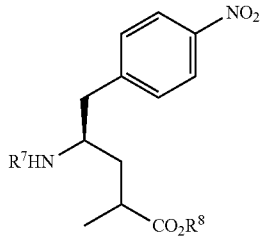

(VIII-a)

In formula (VIII-a), $R^7$ is H or an amine protecting group and $R^8$ is H, $C_1$-$C_{10}$ alkyl, $C_2$-$C_{10}$ alkenyl, $C_2$-$C_{10}$ alkynyl, aryl, cycloaliphatic, alkylcycloaliphatic, arylalkyl, or alkylaryl. Preferably, $R^7$ is H, Boc (t-butoxycarbonyl), Troc (2,2,2-trichloroethoxy carbonyl), Bpoc ((1-methyl-1-(4-biphenyl)ethoxycarbonyl)), Cbz (benzyloxy carbonyl), Aloc (allyloxycarbonyl), methyl amine, or Fmoc (9-fluorenylmethoxycarbonyl). Preferably, $R^8$ is H or $C_1$-$C_5$ alkyl (especially Me).

Another novel intermediate useful for synthesis of compounds of this inventtion has a structure according to formula (VIII-b) The use of compounds of formula (VIII-b) to make compounds of this invention is taught in the figures and examples herein.

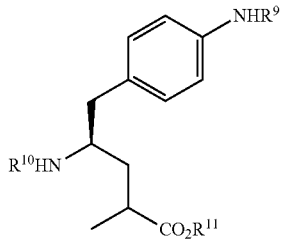

(VIII-b)

In formula (VIII-b), $R^9$ and $R^{10}$ are independently H or an amine protecting group and $R^{11}$ is H, $C_1$-$C_{10}$ alkyl, $C_2$-$C_{10}$ alkenyl, $C_2$-$C_{10}$ alkynyl, aryl, cycloaliphatic, alkylcycloaliphatic, arylalkyl, or alkylaryl. Preferably, $R^9$ and $R^{10}$ are independently selected from H, Boc, Troc, Bpoc, Cbz, Aloc, methylamine, and Fmoc. Preferably, $R^{11}$ is H or $C_1$-$C_5$ alkyl (especially Me). Preferably, where $R^9$ and $R^{10}$ are each an amine protecting group, they are different amine protecting groups.

Additional suitable amine protecting groups for the compounds of formula (VIII-a) and (VIII-b) are disclosed in Greene and Wuts, *Protective Groups in Organic Synthesis*, 3rd edition, pp. 464-653 (John Wiley & Sons, New York, 1999), the disclosure of which is incorporated herein by reference.

Conjugates

In another aspect, there is provided a conjugate comprising cytotoxic compound according to this invention and a ligand, represented by formula (IV)

$$[D(X^D)_a C(X^Z)_b]_m Z \qquad (IV)$$

where Z is ligand; D is a cytotoxic compound according to this invention; and $—(X^D)_a C(X^Z)_b—$ are collectively referred to as a "linker moiety" or "linker" because they link Z and D. Within the linker, C is a cleavable group designed to be cleaved at the site of intended biological action of compound D; $X^D$ and $X^Z$ are referred to as spacer moieties (or "spacers") because they space apart D and C and C and Z, respectively; subscripts a and b are independently 0 or 1 (that is, the presence of $X^D$ and/or $X^Z$ are optional); and subscript m is 1, 2, 3, 4, 5, 6, 7, 8, 9, or 10 (preferably 1, 2, 3, or 4). D, $X^D$, C, $X^Z$ and Z are more fully defined hereinbelow.

Ligand Z—for example an antibody—serves a targeting function. By binding to a target tissue or cell where its antigen or receptor is located, ligand Z directs the conjugate there. Preferably, the target tissue or cell is a cancer tissue or cell and the antigen or receptor is a tumor-associated antigen, that is, an antigen that is uniquely expressed by cancerous cells or is overexpressed by cancer cells, compared to non-cancerous cells. Cleavage of group C at the target tissue or cell releases compound D to exert its cytotoxic effect locally. In some instances, the conjugate is internalized into a target cell by endocytosis and cleavage takes place within the target cell. In this manner, precise delivery of compound D is achieved at the site of intended action, reducing the dosage needed. Also, compound D is normally biologically inactive (or significantly less active) in its conjugated state, thereby reducing undesired toxicity against non-target tissue or cells. As anticancer drugs are often highly toxic to cells in general, this is an important consideration.

As reflected by the subscript m, each molecule of ligand Z can conjugate with more than one compound D, depending on the number of sites D has available for conjugation and the experimental conditions employed. Those skilled in the art will appreciate that, while each individual molecule of ligand Z is conjugated to an integer number of compounds D, a preparation of the conjugate may analyze for a non-integer ratio of compounds D to ligand Z, reflecting a statistical average.

Ligand Z and Conjugation Thereof

Preferably, ligand Z is an antibody. For convenience and brevity and not of limitation, the detailed subsequent discussion herein about the conjugation of ligand Z is written in the context of its being an antibody, but those skilled in the art will understand that other types of ligand Z can be conjugated, mutatis mutandis. For example, conjugates with folic acid as the ligand can target cells having the folate receptor on their surfaces (Vlahov et al. 2008a, 2008b and 2010; Leamon et al. 2009). For the same reason, the detailed discussion below is primarily written in terms of a 1:1 ratio of antibody Z to compound D.

Preferably, ligand Z is an antibody against a tumor associated antigen, allowing a conjugate comprising such a ligand Z to selectively target cancer cells. Examples of such antigens include: mesothelin, prostate specific membrane antigen (PSMA), CD19, CD22, CD30, CD70, B7H4 (also known as O8E), protein tyrosine kinase 7 (PTK7), RG1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., US 2009/0074660 A1 (B7H4); Rao-Naik et al., US 2009/0142349 A1 A2 (CD19); King et al., WO 2008/070569 A2 (CD22); Keler et al., U.S. Pat. No. 7,387,776 B2 (2008) (CD30); Terrett et al., US 2009/0028872 A1 (CD70); Korman et al., U.S. Pat. No. 6,984,720 B1 (2006) (CTLA-4); Korman et al., US 2009/0217401 A1 (PD-1); Huang et al., US 2008/

0279868 A1 (PSMA); Lu et al., US 2010/0034826 A1 (PTK7); Harkins et al., U.S. Pat. No. 7,335,748 B2(2008) (RG1); Terrett et al., WO 2009/045957 A1 (mesothelin); and Xu et al., US 2010/0092484 A1 (CD44); the disclosures of which are incorporated herein by reference.

Ligand Z can also be an antibody fragment or antibody mimetic, such as an affibody, a domain antibody (dAb), a nanobody, a unibody, a DARPin, an anticalin, a versabody, a duocalin, a lipocalin, or an avimer.

Any one of several different reactive groups on ligand Z can be a conjugation site, including ε-amino groups in lysine residues, pendant carbohydrate moieties, carboxylic acid groups, disulfide groups, and thiol groups. Each type of reactive group represents a trade-off, having some advantages and some disadvantages. For reviews on antibody reactive groups suitable for conjugation, see, e.g., Garnett, *Adv. Drug Delivery Rev.* 53 (2001), 171-216 and Dubowchik and Walker, *Pharmacology & Therapeutics* 83 (1999), 67-123, the disclosures of which are incorporated herein by reference.

In one embodiment, ligand Z is conjugated via a lysine ε-amino group. Most antibodies have multiple exposed lysine ε-amino groups, which can be conjugated via amide, urea, thiourea, or carbamate bonds using techniques known in the art, including modification with a heterobifunctional agent (as further described hereinbelow). However, it is difficult to control which and how many ε-amino groups react, leading to potential batch-to-batch variability in conjugate preparations. Also, conjugation may cause neutralization of a protonated ε-amino group important for maintaining the antibody's native conformation or may take place at a lysine near or at the antigen binding site, neither being a desirable occurrence.

In another embodiment, ligand Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with sodium cyanoborohydride. For additional disclosures on conjugation via carbohydrate side chains, see, e.g., Rodwell et al., *Proc. Nat'l Acad. Sci. USA* 83, 2632-2636 (1986); the disclosure of which is incorporated herein by reference. As with lysine ε-amino groups, there are concerns regarding reproducibility of the location of the conjugation site(s) and stoichiometry.

In yet another embodiment, ligand Z can be conjugated via a carboxylic acid group. In one embodiment, a terminal carboxylic acid group is functionalized to generate a carbohydrazide, which is then reacted with an aldehyde-bearing conjugation moiety. See Fisch et al., *Bioconjugate Chemistry* 1992, 3, 147-153.

In yet another embodiment, antibody Z can be conjugated via a disulfide group bridging a cysteine residue on antibody Z and a sulfur on the other portion of the conjugate. Some antibodies lack free thiol (sulfhydryl) groups but have disulfide groups, for example in the hinge region. In such case, free thiol groups can be generated by reduction of native disulfide groups. The thiol groups so generated can then be used for conjugation. See, e.g., Packard et al., *Biochemistry* 1986, 25, 3548-3552; King et al., *Cancer Res.* 54, 6176-6185 (1994); and Doronina et al., *Nature Biotechnol.* 21(7), 778-784 (2003); the disclosures of which are incorporated herein by reference. Again, there are concerns regarding conjugation site location and stoichiometry and the possible disruption of antibody native conformation.

A number of methods are known for introducing free thiol groups into antibodies without breaking native disulfide bonds, which methods can be practiced with a ligand Z of this invention. Depending on the method employed, it may be possible to introduce a predictable number of free sulfhydryls at predetermined locations. In one approach, mutated antibodies are prepared in which a cysteine is substituted for another amino acid. See, for example, Eigenbrot et al., US 2007/0092940 A1; Chilkoti et al., *Bioconjugate Chem.* 1994, 5, 504-507; Urnovitz et al., U.S. Pat. No. 4,698,420 (1987); Stimmel et al., *J. Biol. Chem.*, 275 (39), 30445-30450 (2000); Bam et al., U.S. Pat. No. 7,311,902 B2 (2007); Kuan et al., *J. Biol. Chem.*, 269 (10), 7610-7618 (1994); Poon et al., *J. Biol. Chem.*, 270 (15), 8571-8577 (1995). In another approach, an extra cysteine is added to the C-terminus See, e.g. Cumber et al., *J. Immunol.*, 149, 120-126 (1992); King et al, *Cancer Res.*, 54, 6176-6185 (1994); Li et al., *Bioconjugate Chem.*, 13, 985-995 (2002); Yang et al., *Protein Engineering*, 16, 761-770 (2003); and Olafson et al., *Protein Engineering Design & Selection*, 17, 21-27 (2004). A preferred method for introducing free cysteines is that taught by Liu et al., WO 2009/026274 A1, in which a cysteine bearing amino acid sequence is added to the C-terminus of the heavy chain of an antibody. This method introduces a known number of cysteine residues (one per heavy chain) at a known location remote from the antigen binding site. The disclosures of the documents cited in this paragraph are all incorporated herein by reference.

In yet another embodiment, lysine ε-amino groups can be modified with heterobifunctional reagents such as 2-iminothiolane or N-succinimidyl-3-(2-pyridyldithio)-propionate (SPDP), converting an ε-amino group into a thiol or disulfide group—creating a cysteine surrogate, as it were. However, this method suffers from the same conjugation location and stoichiometry limitations associated with ε-amino groups proper.

In yet another preferred embodiment, ligand Z is conjugated via the nucleophilic addition product of a thiol group to an acceptor moiety. A preferred acceptor moiety is a maleimide group, whose reaction with an antibody thiol group is generically illustrated below. The thiol group can be a native one, or one introduced as described above.

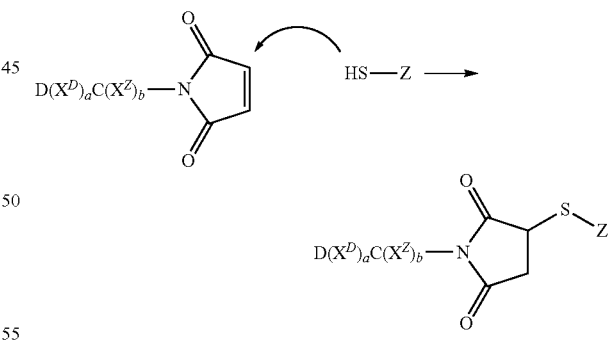

Linker—$(X^D)_aC(X^Z)_b$—

As noted above, the linker portion of a conjugate of this invention comprises up to three elements: a cleavable group C and optional spacers $X^Z$ and $X^D$.

Cleavable group C is a group cleavable under physiological conditions, preferably is selected such that it is relatively stable while the conjugate is in general circulation in the blood plasma, but is readily cleaved once the conjugate reaches its site of intended action, that is, near, at, or within the target cell. Preferably, the conjugate is internalized by endocytosis by a target cell upon binding of antibody Z to an antigen displayed on the surface of the target cell. Subsequently, cleavage of group C occurs in a vesicular body of the target cell (an early endosome, a late endosome, or, especially, a lysosome).

In one embodiment, group C is a pH sensitive group. The pH in blood plasma is slightly above neutral, while the pH inside a lysosome is acidic, circa 5. Thus, a group C whose cleavage is acid catalyzed will cleave at a rate several orders of magnitude faster inside a lysosome than in the blood plasma rate. Examples of suitable acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 102, 1048-1054 (1981) and Yang et al., *Proc. Natl Acad. Sci (USA)*, 85, 1189-1193 (1988); the disclosures of which are incorporated herein by reference.

In another embodiment, group C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. For additional disclosures relating to disulfide cleavable groups in conjugates, see, e.g., Thorpe et al., *Cancer Res.* 48, 6396-6403 (1988); Santi et al., US 2005/0287155 A1; Ng et al., U.S. Pat. No. 6,989,452 B2 (2006); Ng et al., WO 2002/096910 A1; Boyd et al., U.S. Pat. No. 7,691,962 B2; and Sufi et al., WO 2008/083312 A2; the disclosures of which are incorporated herein by reference.

A preferred group C comprises a peptide bond that is cleaved, preferentially by a protease, at the intended site of action, as opposed to by a protease in the serum. Typically, group C comprises from 1 to 20 amino acids, preferably from 1 to 6 amino acids, more preferably from 1 to 3 amino acids. The amino acid(s) can be natural and/or unnatural α-amino acids. Natural amino acids are those encoded by the genetic code, as well as amino acids derived therefrom, e.g., hydroxyproline, γ-carboxyglutamate, citrulline, and O-phosphoserine. The term amino acid also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The term "unnatural amino acid" is intended to represent the "D" stereochemical form, the natural amino acids being of the "L" form.

Preferably, group C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of the target tissue, e.g., a protease released by nearby dying cells or a tumor-associated protease. Exemplary extracellular tumor-associated proteases are matrix metalloproteases (MMP), thimet oligopeptidase (TOP) and CD10.

For conjugates that are designed to be internalized by a cell, group C preferably comprises an amino acid sequence selected for cleavage by an endosomal or lysosomal protease, especially the latter. Non-limiting examples of such proteases include cathepsins B, C, D, H, L and S, especially cathepsin B. Cathepsin B preferentially cleaves peptides at a sequence -$AA^2$-$AA^1$- where $AA^1$ is a basic or strongly hydrogen bonding amino acid (such as lysine, arginine, or citrulline) and $AA^2$ is a hydrophobic amino acid (such as phenylalanine, valine, alanine, leucine, or isoleucine), for example Val-Cit (where Cit denotes citrulline) or Val-Lys. (Herein, amino acid sequences are written in the N-to-C direction, as in $H_2N$-$AA^2$-$AA^1$-$CO_2H$, unless the context clearly indicates otherwise.) For additional information regarding cathepsin-cleavable groups, see Dubowchik et al., *Biorg. Med. Chem. Lett.* 8, 3341-3346 (1998); Dubowchik et al., *Bioorg. Med. Chem. Lett.*, 8 3347-3352 (1998); and Dubowchik et al., *Bioconjugate Chem.* 13, 855-869 (2002); the disclosures of which are incorporated by reference. Another enzyme that can be utilized for cleaving peptidyl linkers is legumain, a lysosomal cysteine protease that preferentially cleaves at Ala-Ala-Asn.

In one embodiment, Group C is a peptide comprising the two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to five amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu.

The preparation and design of cleavable groups C consisting of a single amino acid is disclosed in Chen et al., US 2010/0113476 A1, the disclosure of which is incorporated herein by reference.

Group C can also be a photocleavable one, for example a nitrobenzyl ether that is cleaved upon exposure to light.

Group C can be bonded directly to antibody Z or compound D; that is, spacers $X^Z$ and $X^D$, as the case may be, can be absent. For example, if group C is a disulfide, one of the two sulfurs can be a cysteine residue or its surrogate on antibody Z. Or, group C can be a hydrazone bonded to an aldehyde on a carbohydrate side chain of the antibody. Or, group C can be a peptide bond formed with a lysine ε-amino group of antibody Z. In a preferred embodiment, compound D is directly bonded to group C via a peptidyl bond to a carboxyl or amine group in compound D.

When present, spacer $X^Z$ provides spatial separation between group C and antibody Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

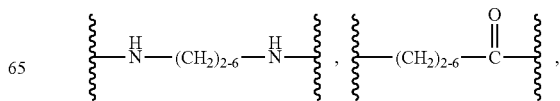

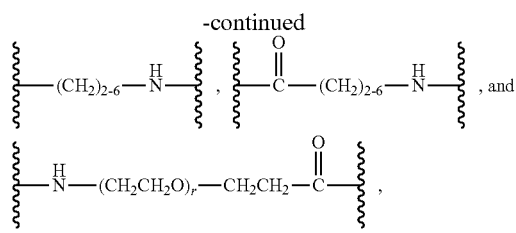

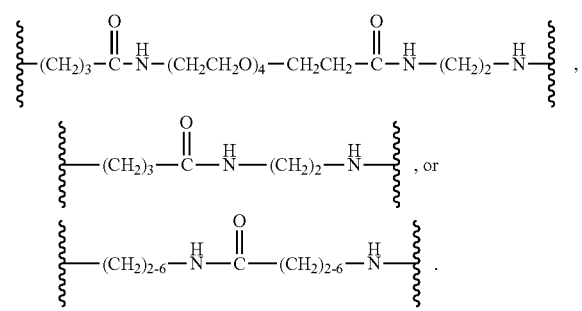

where the subscript r is 1 to 24, preferably 2 to 4. These segments can be combined to make spacers $X^Z$ such as:

Spacer $X^D$, if present, provides spatial separation between group C and compound D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, as described above in the context of spacer $X^Z$.

Either spacer $X^Z$ or $X^D$, or both, can comprise a self-immolating moiety. A self-immolating moiety is a moiety that (1) is bonded to group C and either antibody Z or cytotoxin D and (2) has a structure such that cleavage from group C initiates a reaction sequence resulting in the self-immolating moiety disbonding itself from antibody Z or cytotoxin D, as the case may be. In other words, reaction at a site distal from antibody Z or cytotoxin D (cleavage from group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof were to remain attached to cytotoxin D, the biological activity of the latter may be impaired. The use of a self-immolating moiety is especially desirable where cleavable group C is a polypeptide.

Exemplary self-immolating moieties (i)-(v) bonded to a hydroxyl or amino group on a partner molecule D are shown below:

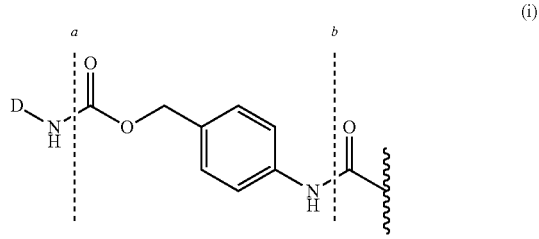
(i)

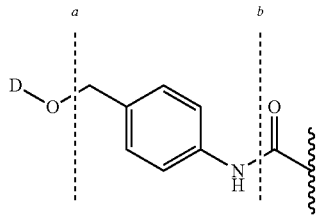
(ii)

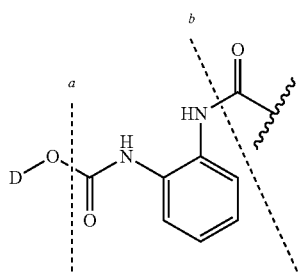
(iii)

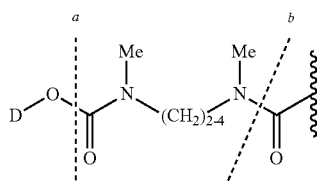
(iv)

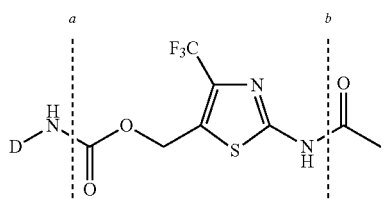
(v)

The self-immolating moiety is the structure between dotted lines a and b, with adjacent structural features shown to provide context. Self-immolating moieties (i) and (v) are bonded to a compound D-NH$_2$ (i.e., compound D is conjugated via an amino group), while self-immolating moieties (ii), (iii), and (iv) are bonded to a compound D-OH (i.e., compound D is conjugated via a hydroxyl or carboxyl group). Cleavage of the amide bond at dotted line b releases the amide nitrogen as an amine nitrogen, initiating a reaction sequence that results in the cleavage of the bond at dotted line a and the consequent release of D-OH or D-NH$_2$, as the case may be. For additional disclosures regarding self-immolating moieties, see Carl et al., *J. Med. Chem.*, 24 (3), 479-480 (1981); Carl et al., WO 81/01145 (1981); Dubowchik et al., *Pharmacology & Therapeutics*, 83, 67-123 (1999); Firestone et al., U.S. Pat. No. 6,214,345 B1 (2001); Toki et al., *J. Org. Chem.* 67, 1866-1872 (2002); Doronina et al., *Nature Biotechnology* 21 (7), 778-784 (2003) (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; and Senter et al., US 2003/0096743 A1; the disclosures of which are incorporated by reference.

Compound D—Linker Compositions

Conjugates of this invention preferably are prepared by first joining a compound D and linker $(X^D)_aC(X^Z)_b$ to form a drug-linker composition represented by formula (V-a):

$$D\text{-}(X^D)_aC(X^Z)_b\text{—}R^{31} \tag{V-a}$$

where $R^{31}$ is a functional group suitable for reacting with a functional group on antibody Z to form the conjugate. Examples of suitable groups $R^{31}$ include:

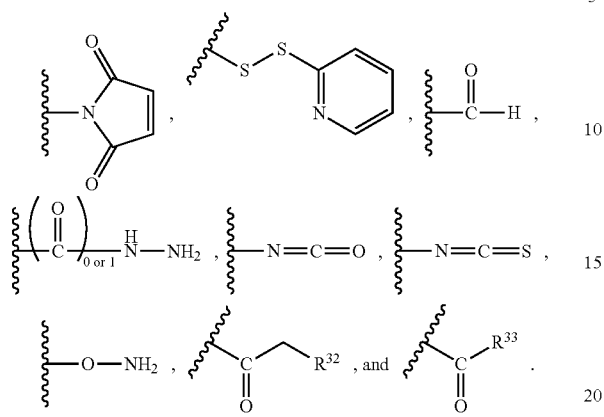

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties $D\text{-}(X^D)_aC(X^Z)_b\text{---}R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., US 2006/0004081 A1; Gangwar et al., US 2006/0247295 A1; Boyd et al., US 2008/0279868 A1; Gangwar et al., US 2008/0281102 A1; Gangwar et al., US 2008/0293800 A1; Sufi et al., WO 2008/083312 A2; and Chen et al., US 2010/0113476 A1; the disclosures of which are incorporated herein by reference.

In a preferred embodiment, $R^{31}$ is a maleimide group and the cytotoxic compound-linker molecule can be represented by formula (V-b):

$C(=O)(C_2\text{-}C_{10}$ alkenyl), unsubstituted or substituted $C(=O)(C_2\text{-}C_{10}$ alkynyl), unsubstituted or substituted cycloaliphatic, unsubstituted or substituted heterocycloaliphatic, unsubstituted or substituted arylalkyl, or unsubstituted or substituted alkylaryl;

$R^{4'}$ is

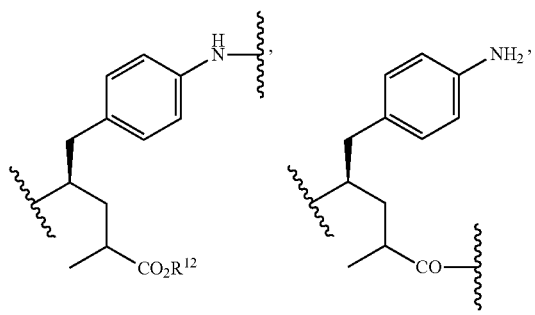

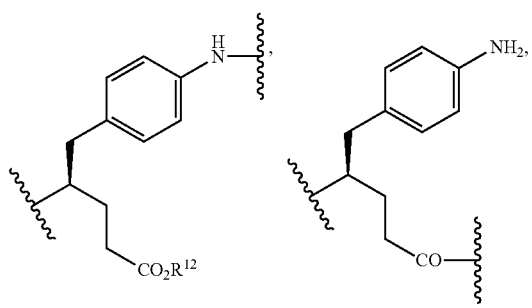

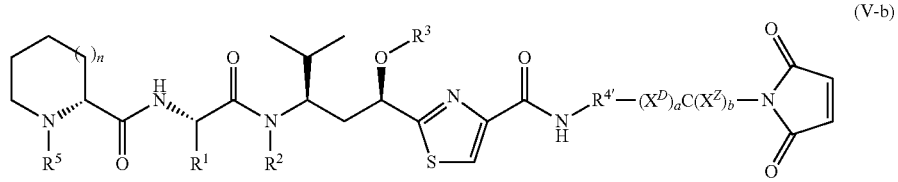

(V-b)

wherein n is 0, 1, or 2;

$R^1$, $R^2$ and $R^3$ are independently H, unsubstituted or substituted $C_1\text{-}C_{10}$ alkyl, unsubstituted or substituted $C_2\text{-}C_{10}$ alkenyl, unsubstituted or substituted $C_2\text{-}C_{10}$ alkynyl, unsubstituted or substituted aryl, unsubstituted or substituted heteroaryl, unsubstituted or substituted $(CH_2)_{1\text{-}2}O(C_1\text{-}C_{10}$ alkyl), unsubstituted or substituted $(CH_2)_{1\text{-}2}O(C_2\text{-}C_{10}$ alkenyl), unsubstituted or substituted $(CH_2)_{1\text{-}2}O(C_2\text{-}C_{10}$ alkynyl), $(CH_2)_{1\text{-}2}OC(=O)(C_1\text{-}C_{10}$ alkyl), unsubstituted or substituted $(CH_2)_{1\text{-}2}OC(=O)$ $(C_2\text{-}C_{10}$ alkenyl), unsubstituted or substituted $(CH_2)_{1\text{-}2}$ $OC(=O)(C_2\text{-}C_{10}$ alkynyl), unsubstituted or substituted $C(=O)(C_1\text{-}C_{10}$ alkyl), unsubstituted or substituted -continued

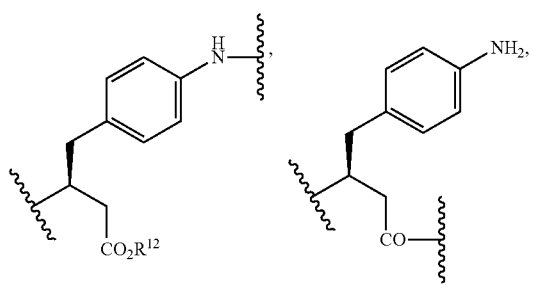

-continued

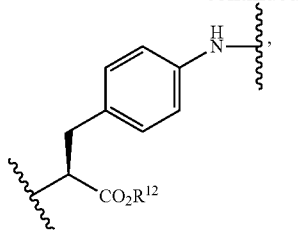

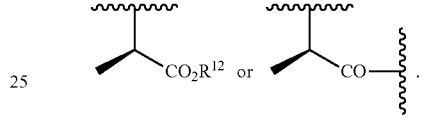

In the structures

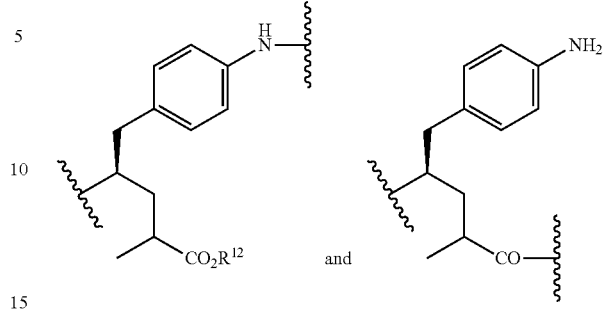

the stereochemistry at the methyl group alpha to the carboxyl group preferably corresponds to that of the naturally occurring tubulysins, i.e.:

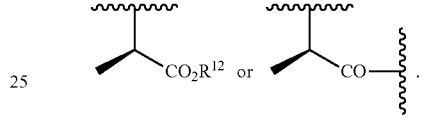

Preferably, in formula (V-b) n is 1, $R^1$ is an isoleucyl residue, a is 0, b is 1, and C comprises one to five amino acids (preferably one to two), and $R^{4'}$ is bonded to C by a peptidyl bond that is enzymatically cleavable, and $R^5$ is Me. This preferred embodiment is represented by formula (V-c):

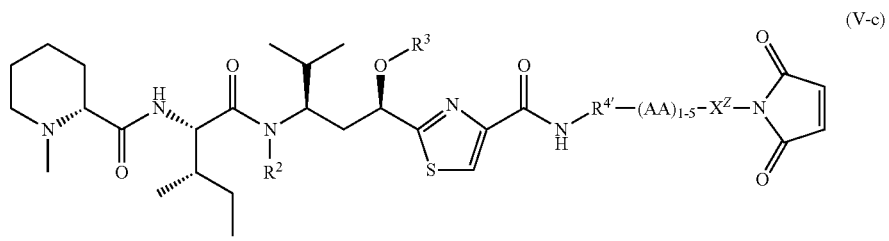

wherein $R^{12}$ is H, $C_1$-$C_5$ alkyl, $C_2$-$C_5$ alkenyl, or $C_2$-$C_5$ alkynyl; and $R^5$ is H, $C_1$-$C_5$ alkyl, $C_2$-$C_5$ alkenyl, $C_2$-$C_5$ alkynyl, CO($C_1$-$C_5$ alkyl), CO($C_2$-$C_5$ alkenyl), or CO($C_2$-$C_5$ alkynyl);

$X^D$ and $X^Z$ are spacer groups;

C is a cleavable group; and a and b are independently 0 or 1;

wherein group $R^{4'}$ is linked via a carboxyl or amine group therein to either group $X^D$ in the event a is 1 or to group C in the event a is 0.

Preferably, the link between the carboxyl or amine group in $R^{4'}$ and group $X^D$ or C, as the case may be, is via an amide bond.

where $R^2$, $R^3$, and $R^{4'}$ are as defined in respect of formula (V-b), each AA independently is a natural amino acid, and $X^Z$ is $CH_2CH_2NHC(=O)(CH_2)_{2-5}$ or $C(=O)(CH_2)_{2-5}$. Preferred amino acids AA are lysine, citrulline, alanine, valine, glycine, and phenylalanine.

In formula (V-b), $R^1$ preferably is H, $C_1$-$C_5$ alkyl, $C_2$-$C_5$ alkenyl, or $C_2$-$C_5$ alkenyl, and is more preferably an isoleucyl residue, that is:

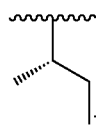

In formulae (V-b) and (V-c), $R^2$ preferably is H, $C_1$-$C_5$ alkyl, $C_2$-$C_5$ alkenyl, $CH_2O(C_1$-$C_5$ alkyl), $CH_2O(C_2$-$C_5$ alkenyl), $CH_2O(C=O)(C_1$-$C_5$ alkyl), or $CH_2OC(=O)(C_2$-$C_5$ alkenyl); and more preferably is H, Me, Et, $CH_2OMe$, $CH_2OEt$, $CH_2OC(=O)i$-Bu, $CH_2OC(=O)n$-Pr, $CH_2OC(=O)CH=CH_2$, or $CH_2OC(=O)Me$.

In formulae (V-b) and (V-c), $R^3$ preferably is H, $C_1$-$C_5$ alkyl, $C_2$-$C_5$ alkenyl, $C(=O)C_1$-$C_5$ alkyl, or $C(=O)C_2$-$C_5$ alkenyl; and more preferably is H, Me, Et, or $C(=O)$Me.

In formulae (V-b) and (V-c), $R^{4'}$ preferably is

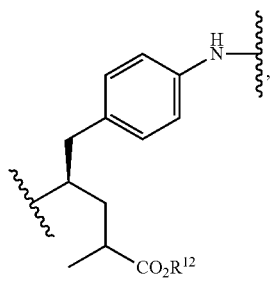

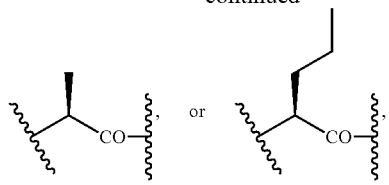

with $R^{4'}$ equaling

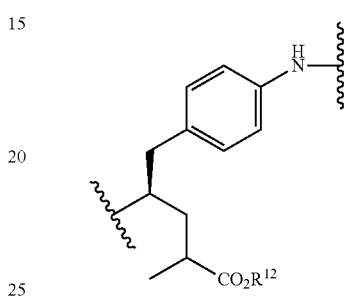

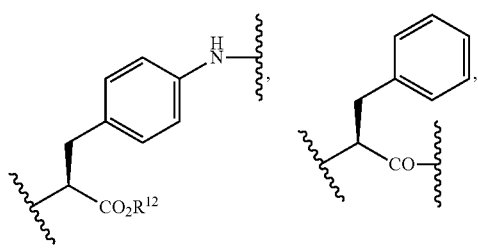

and $R^{12}$ equaling H, Me, or Et being especially preferred.

In formula (V-b), n preferably is 1 and $R^5$ preferably is methyl; that is, the ring in the Mep subunit preferably is an N-methyl piperidinyl one.

In another embodiment, this invention provides a compound having a structure represented by formula (V-d)

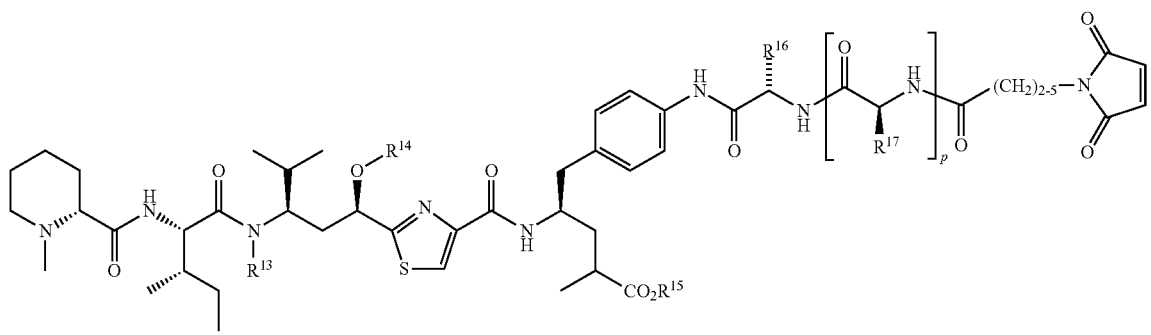

(V-d)

where $R^{13}$ is Me, n-Pr, $CH_2OMe$, or $CH_2OC(=O)CH_2CH(Me)_2$; $R^{14}$ is Me or $C(=O)Me$; and $R^{15}$ is H or $C_1$-$C_5$ alkyl (preferably H, Me, or Et); $R^{16}$ is a lysine $((CH_2)_4NH_2)$ or citrulline $((CH_2)_3NHC(=O)NH_2)$ side chain group; $R^{17}$ is a valine $(C(Me)_2)$ or alanine (Me) side chain group; and p is 0 or 1.

Examples of specific cytotoxic compound-linker constructs of this invention are shown below in formulae (VI-a) through (VI-t). Compound-linker (VI-n) is especially preferred. They have a maleimide group and are ready for conjugation to an antibody via a sulfhydryl group thereon, by a procedure such as that described below.

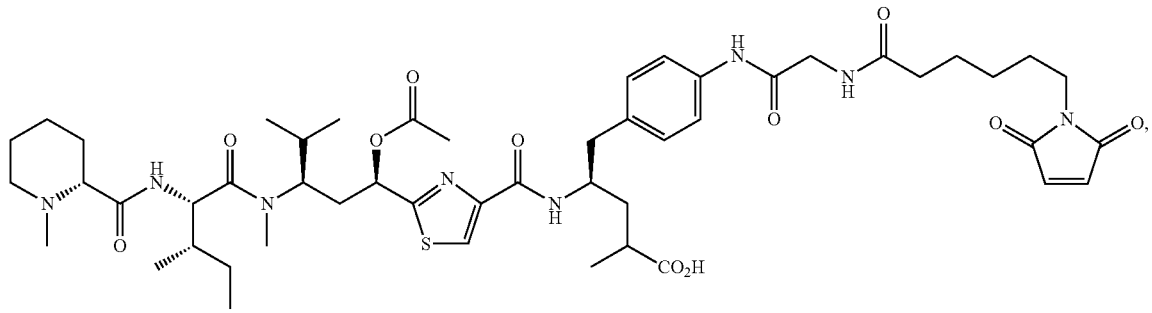
(VI-a)

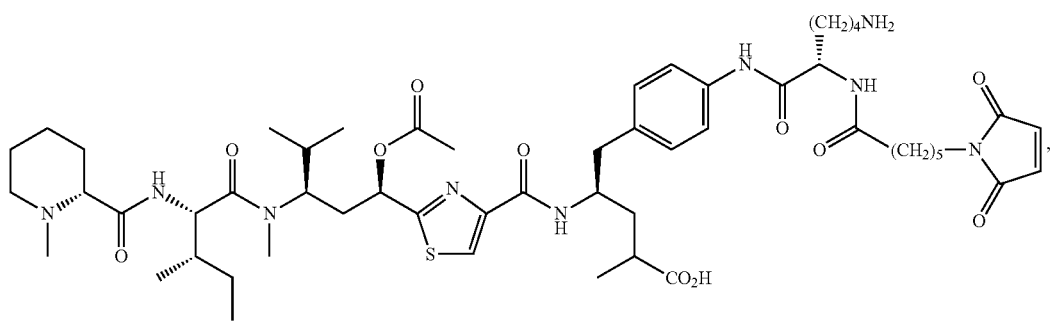
(VI-b)

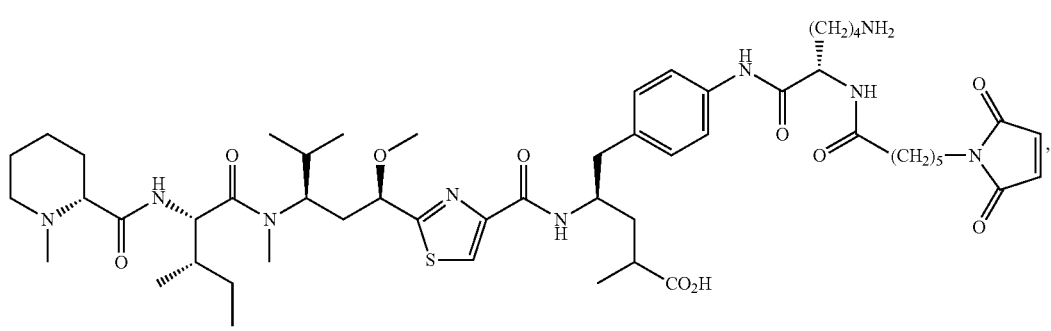
(VI-c)

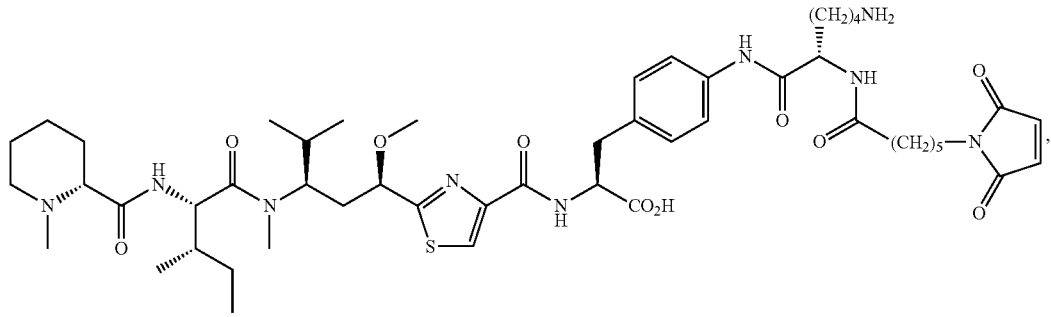
(VI-d)

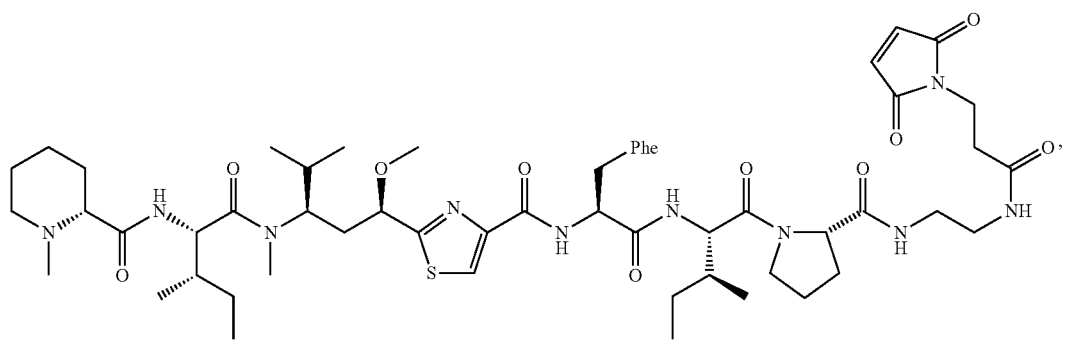
(VI-e)
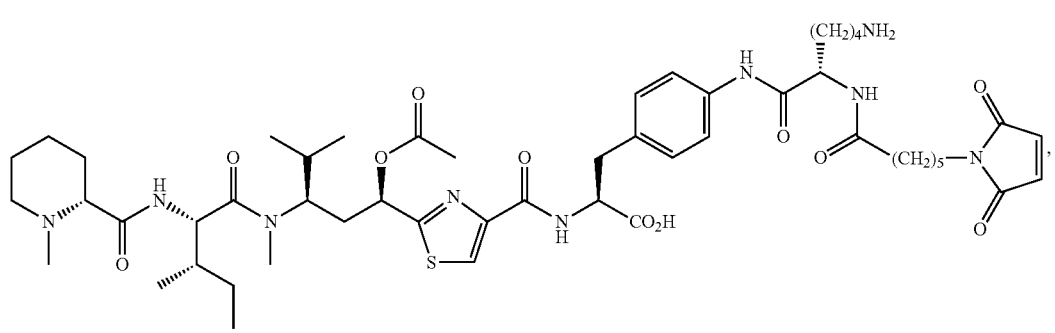
(VI-f)
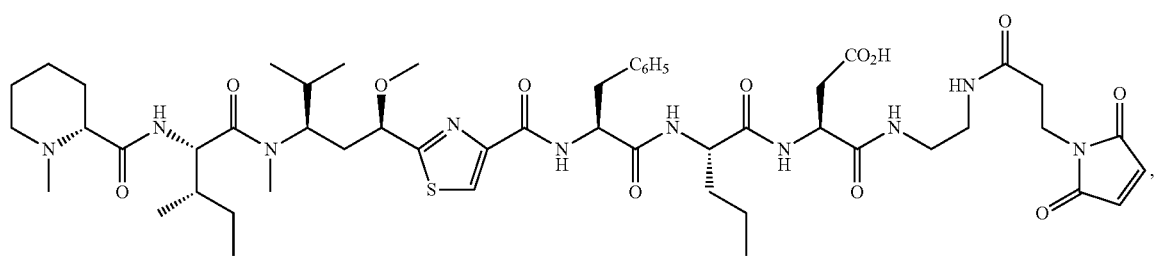
(VI-g)
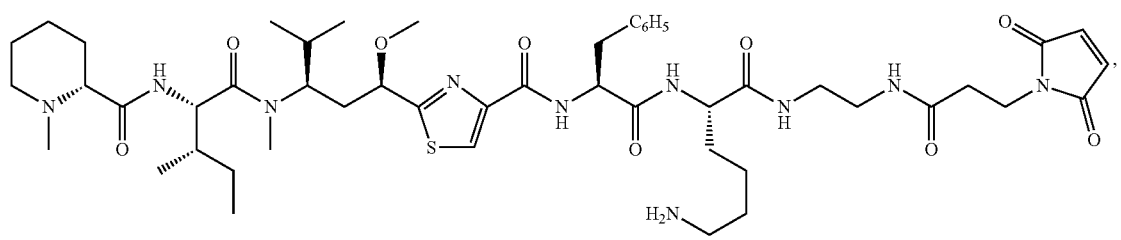
(VI-h)
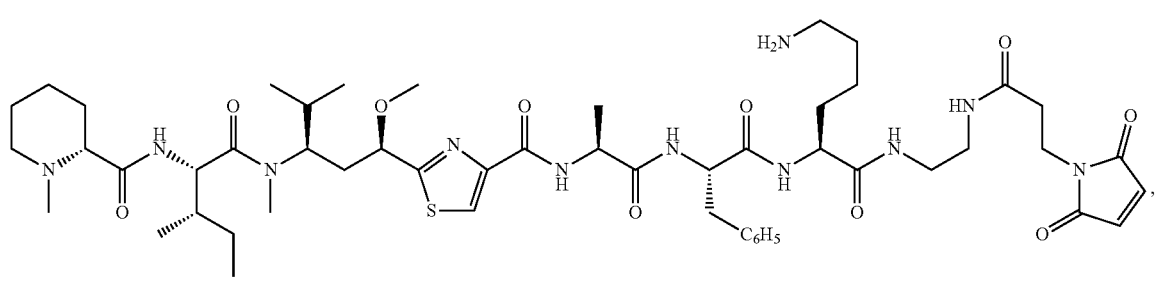
(VI-i)

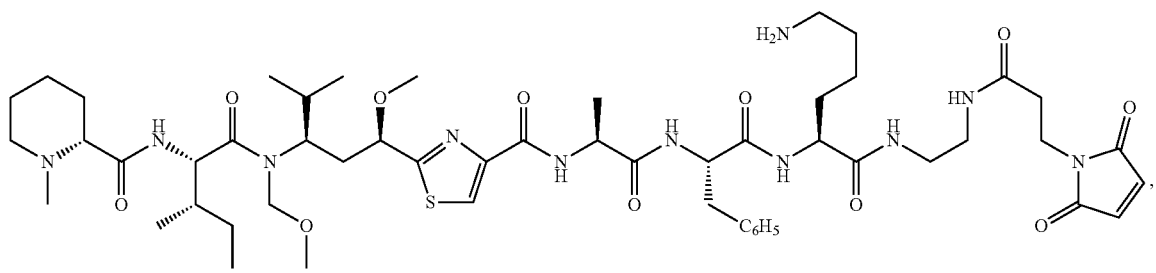
(VI-j)
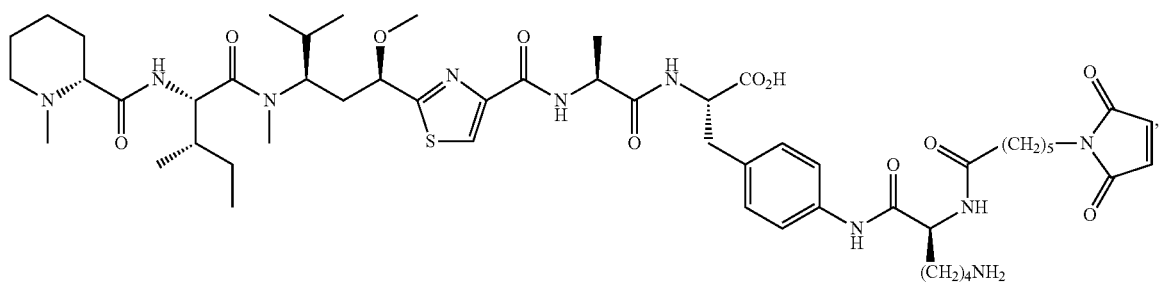
(VI-k)
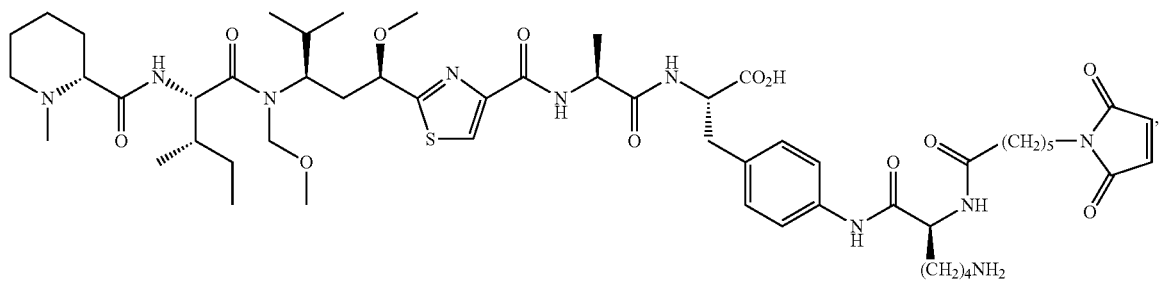
(VI-l)
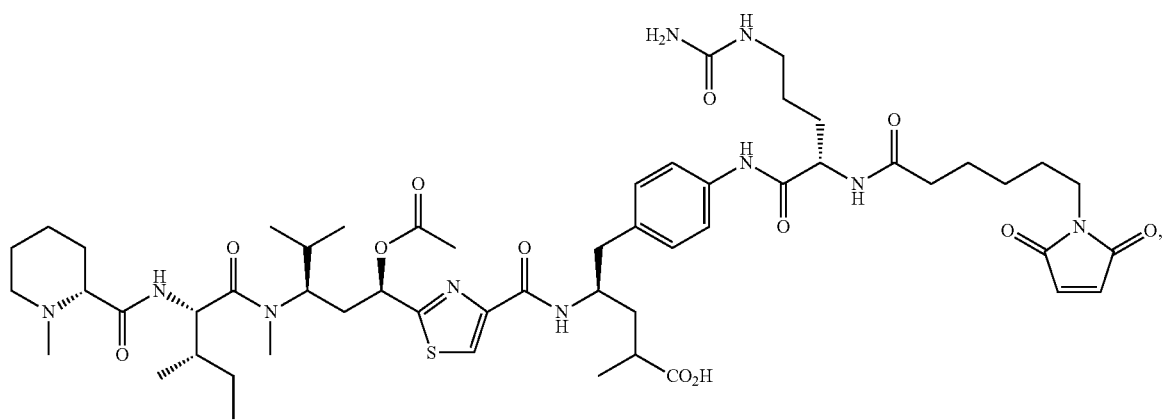
(VI-m)

-continued
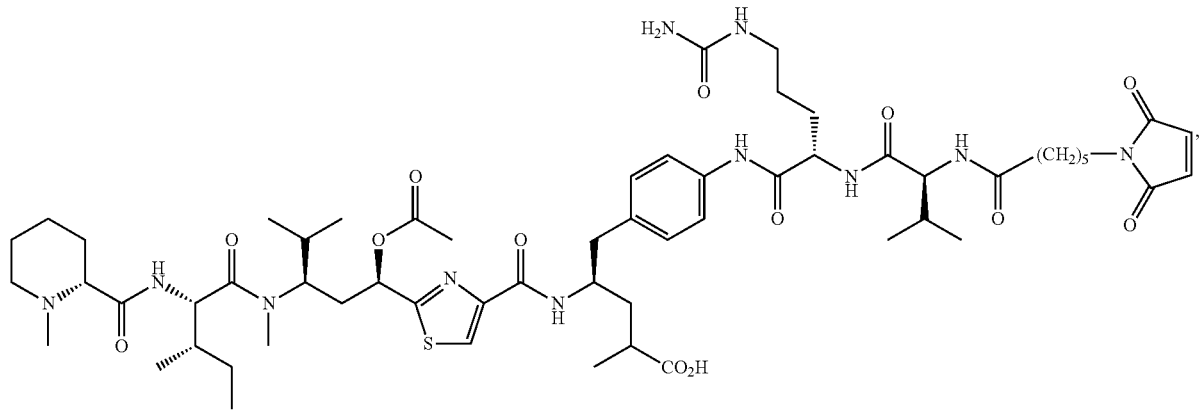
(VI-n)
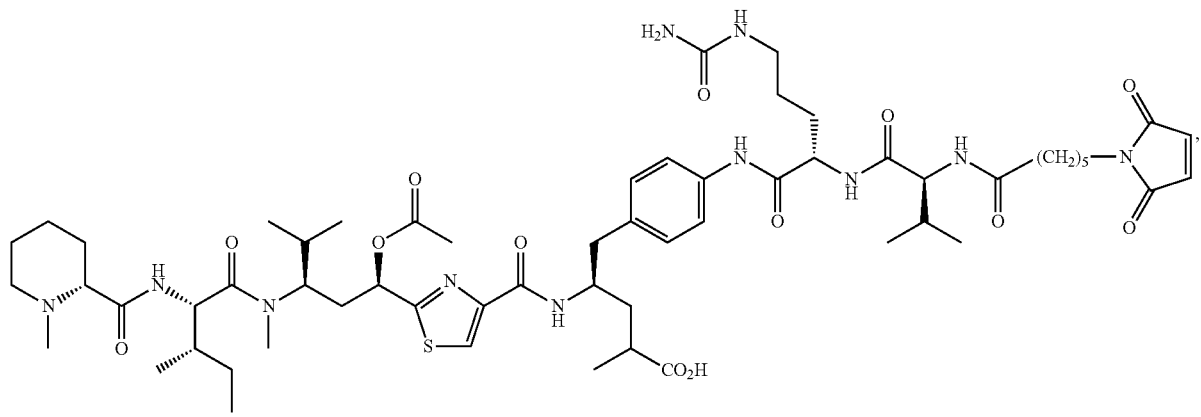
(VI-o)
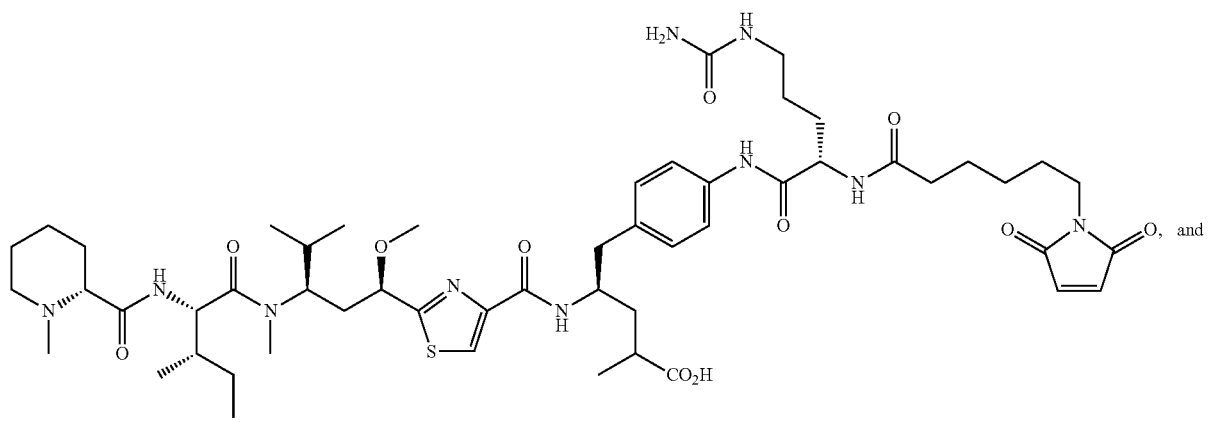
(VI-p)

-continued
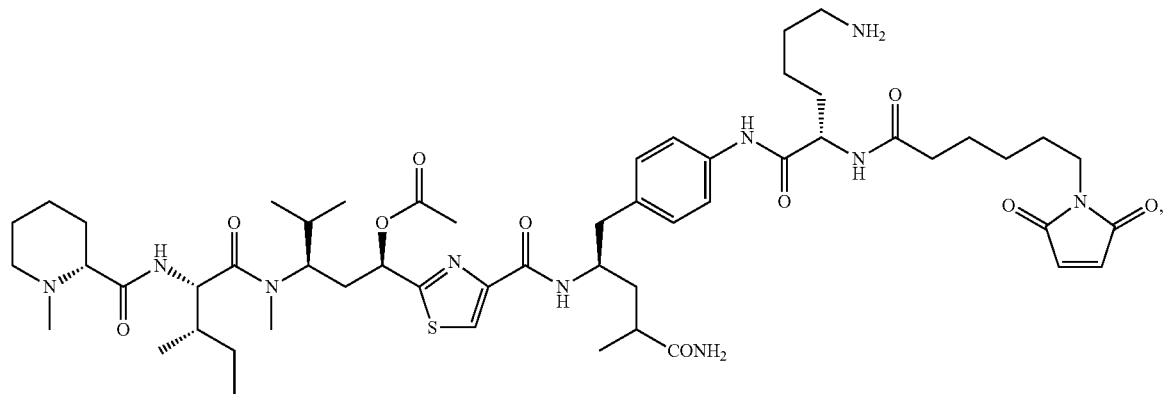
(VI-q)
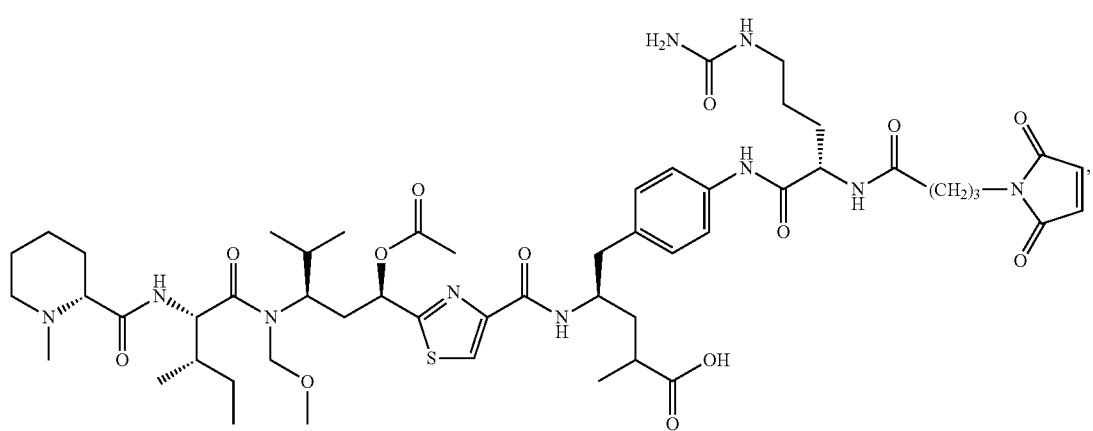
(VI-r)
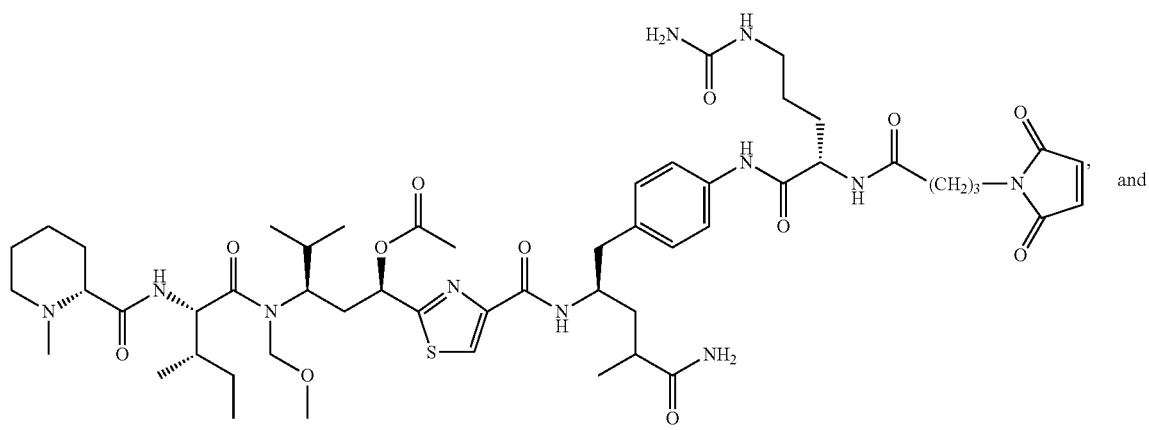
(VI-s), and (VI-t)

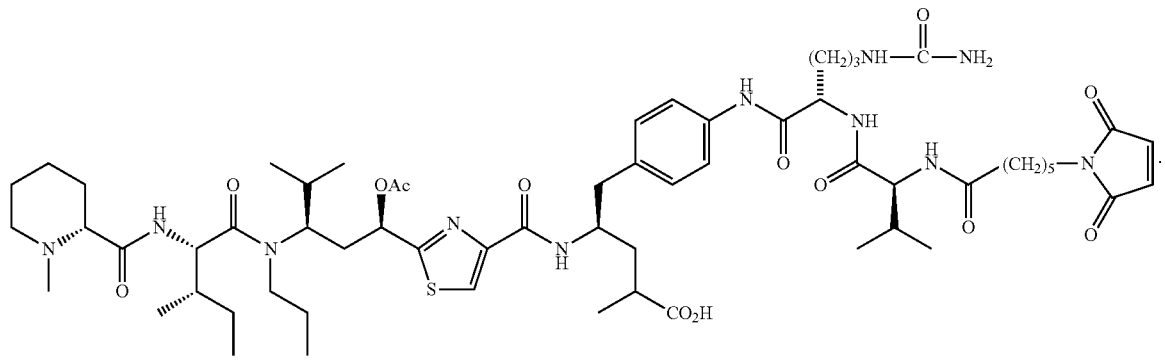

Preparation of Conjugates

The following is an illustrative procedure, based on introduction of free thiol groups into an antibody by reaction of lysine ε-amino groups with 2-iminothiolane, followed by reaction with a maleimide-containing drug-linker moiety such as described above. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT (room temperature, circa 25° C.), the antibody is desalted into 50 mM pH 6.0 HEPES buffer using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM pH 6.0 HEPES buffer containing 5 mM glycine and 2 mM DTPA). The thiolated material is maintained on ice while the number of thiols introduced is quantitated as described above.

After verification of the number of thiols introduced, the drug-linker moiety is added at a 3-fold molar excess per thiol. The conjugation reaction is allowed to proceed in conjugation buffer also containing a final concentration of 5% dimethylsulfoxide (DMSO), or similar alternative solvent. Commonly, the drug-linker stock solution is dissolved in 100% DMSO. The stock solution is added directly to the thiolated antibody, which has enough DMSO added to bring the final concentration to 10%, or pre-diluted in conjugation buffer containing a final concentration of 10% DMSO, followed by addition to an equal volume of thiolated antibody.

The conjugation reaction mixture is incubated at RT for 2 h with stirring. Following incubation, the conjugation reaction mixture is centrifuged and filtered through a 0.2 μm filter. Purification of the conjugate can be achieved through chromatography using a number of methods. In one method, the conjugate is purified using size-exclusion chromatography on a SEPHACRYL™ S200 column pre-equilibrated with 50 mM pH 7.2 HEPES buffer containing 5 mM glycine and 50 mM NaCl. Chromatography is carried out at a linear flow rate of 28 cm/h. Fractions containing conjugate are collected, pooled and concentrated. In an alternative method, purification can be achieved through ion-exchange chromatography. Conditions vary from antibody to antibody and should to be optimized in each case. For example, antibody-drug conjugate reaction mix is applied to an SP-SEPHAROSE™ column pre-equilibrated in 50 mM pH 5.5 HEPES containing 5 mM glycine. The antibody conjugate is eluted using a gradient of 0-1 M NaCl in equilibration buffer at pH 5.5. Relevant fractions containing the conjugate are pooled and dialyzed against formulation buffer (50 mM pH 7.2 HEPES buffer containing 5 mM glycine and 100 mM NaCl).

Those skilled in the art will understand that the above-described conditions and methodology are exemplary and non-limiting and that other approaches for conjugation are known in the art and usable in the present invention.

Using the foregoing techniques, compounds of this invention were conjugated using antibodies 2A10, an anti-PSMA antibody (Huang et al., US 2009/0297438); 2H5, an anti-CD70 antibody (Terrett et al., US 2009/0028872); 1F4, an anti-CD70 antibody (Coccia et al., WO 2008/074004); or 6A4, an anti-mesothelin antibody (Terrett et al., WO 2009/045957). The resulting conugates may be depicted by the following formulae, where Ab represents an antibody. Those skilled in the art will understand that in these formulae the cytotoxin-antibody compound ratio is shown as 1:1 for simplicity, but that in actuality the ratio is usually greater, such as between 2 to 3.

53 54
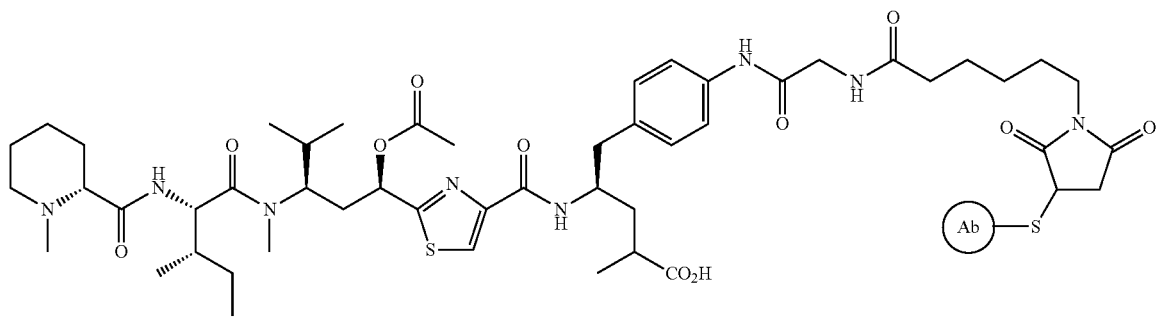
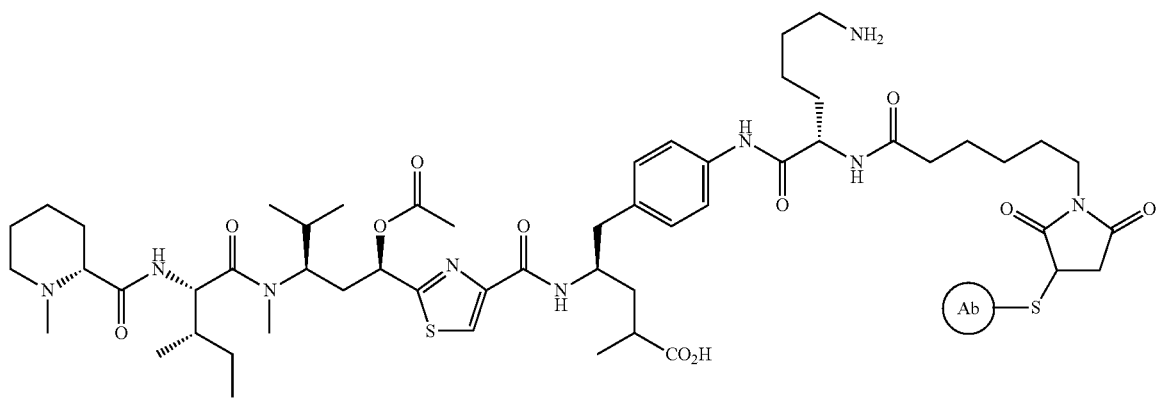
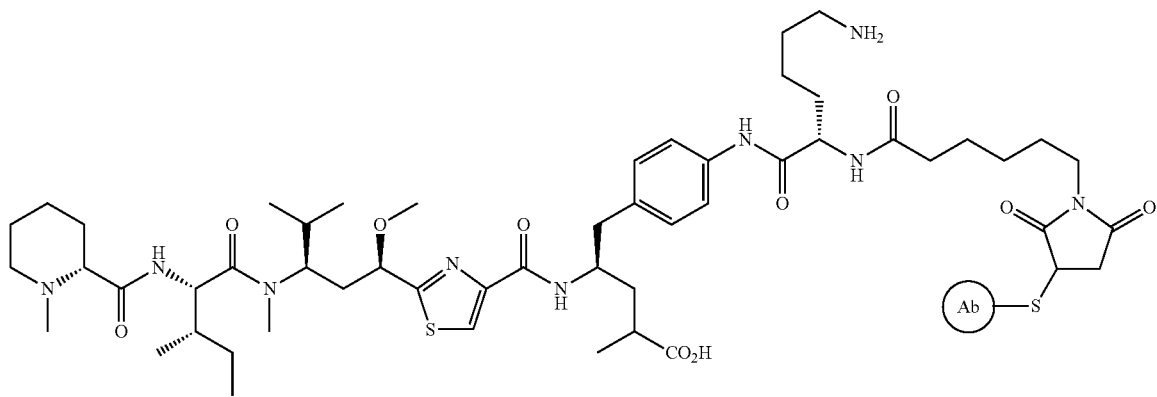
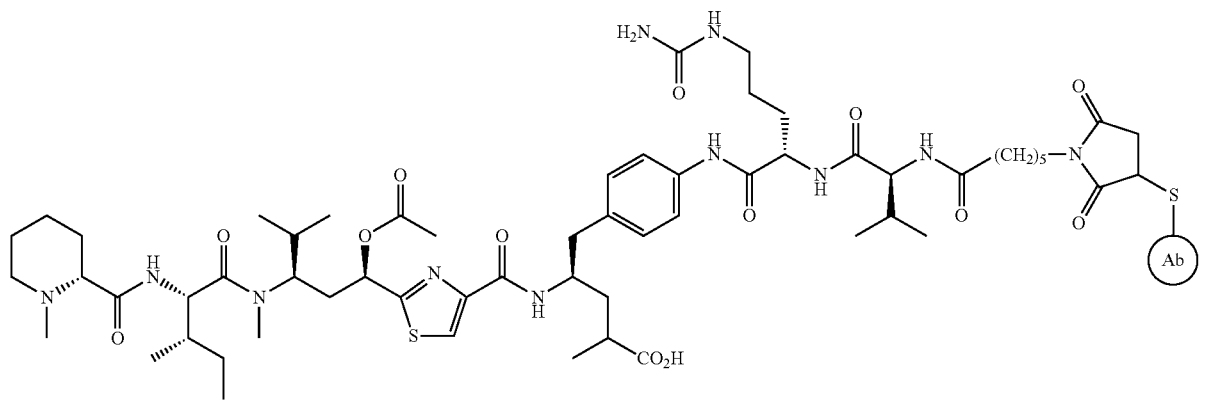

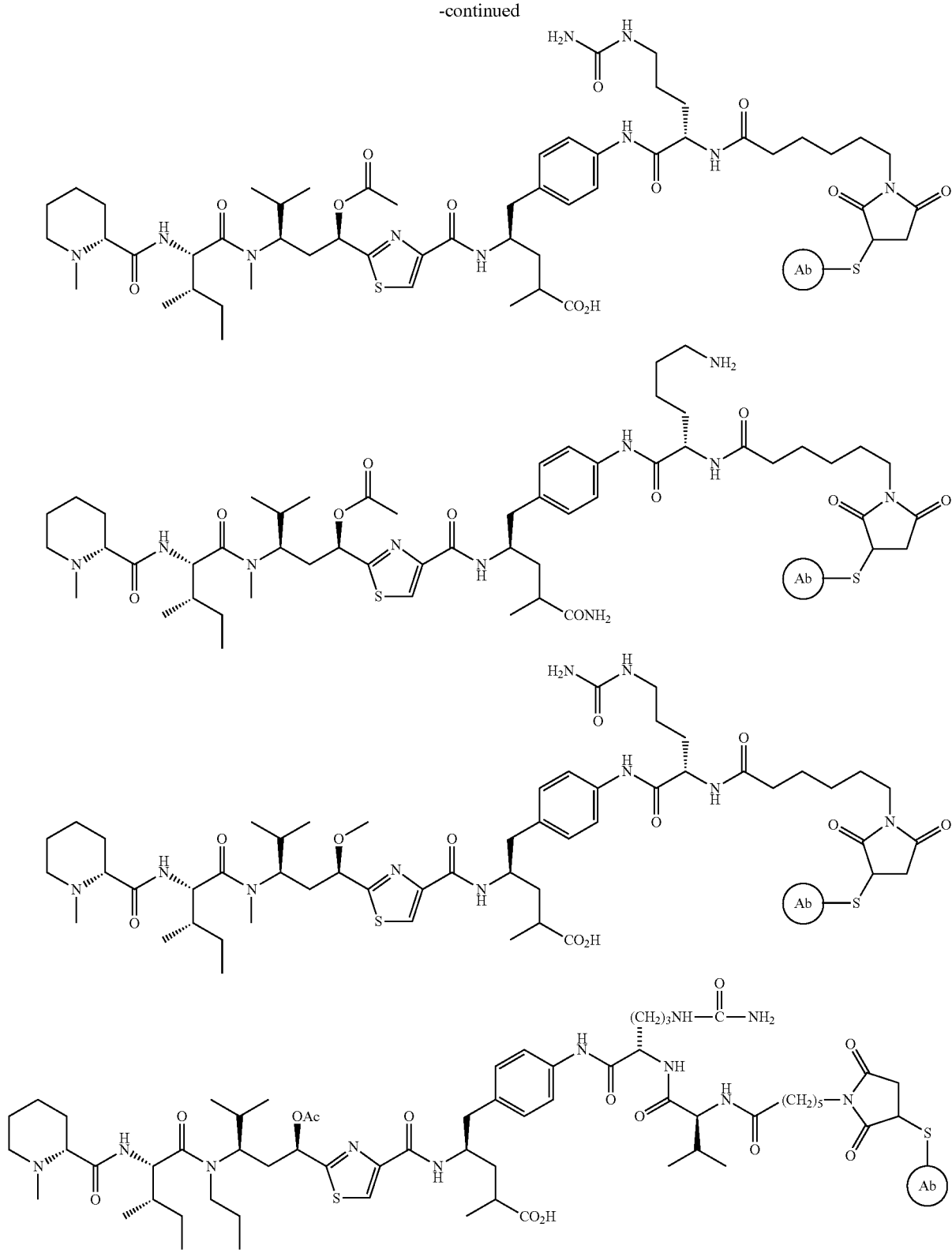

Pharmaceutical Compositions

In another aspect, the present disclosure provides a pharmaceutical composition comprising a compound of the present disclosure formulated together with a pharmaceutically acceptable excipient. It may optionally contain one or more additional pharmaceutically active ingredients, such as an antibody or another drug. The pharmaceutical compositions can be administered in a combination therapy with another therapeutic agent, especially another anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy,* 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred per cent, this amount will range from about 0.01 per cent to about ninety-nine percent of active ingredient, preferably from about 0.1 per cent to about 70 per cent, most preferably from about 1 per cent to about 30 per cent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/mL and in some methods about 25-300 μg/mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal.

The pharmaceutical composition can be a controlled or sustained release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems,* J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V.V. Ranade (1989) *J. Clin. Pharmacol.* 29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses

Compounds of this invention or their conjugatescan be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be colorectal cancer, liver cancer, prostate cancer, breast cancer, melanoma, glioblastoma, lung cancer, pancreatic cancer, ovarian cancer, multiple myeloma, renal cancer, leukemia (especially ALL, APL, or AML), or lymphoma.

Compounds of this invention or their conjugates can be administered in combination with other anti-cancer or cytotoxic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific anti-cancer or cytotoxic agents include β-lapachone, ansamitocin P3, auristatin, bicalutamide, bleomycin, bortezomib, busulfan, callistatin A, camptothecin, capecitabine, CC-1065, cisplatin, cryptophycins, daunorubicin, disorazole, docetaxel, doxorubicin, duocarmycin, dynemycin A, epothilones, etoposide, floxuridine, floxuridine, fludarabine, fluoruracil, gefitinib, geldanamycin, 17-allylamino-17-demethoxygeldanamycin (17-AAG), 17-(2-dimethylaminoethyl)amino17-demethoxygeldanamycin (17-DMAG), gemcitabine, hydroxyurea, imatinib, interferons, interleukins, irinotecan, maytansine, methotrexate, mitomycin C, oxaliplatin, paclitaxel, suberoylanilide hydroxamic acid (SAHA), thiotepa, topotecan, trichostatin A, vinblastine, vincristine, vindesine, lenalidomide (REVLIMID®), bevacizumab (AVASTIN®), trastuzumab (HERCEPTIN®), and cetuximab (ERBITUX®).

EXAMPLES

The practice of this invention can be further understood by reference to the following examples, which are provided by way of illustration and not of limitation.

Example 1

Scheme 1

Figure 1A:
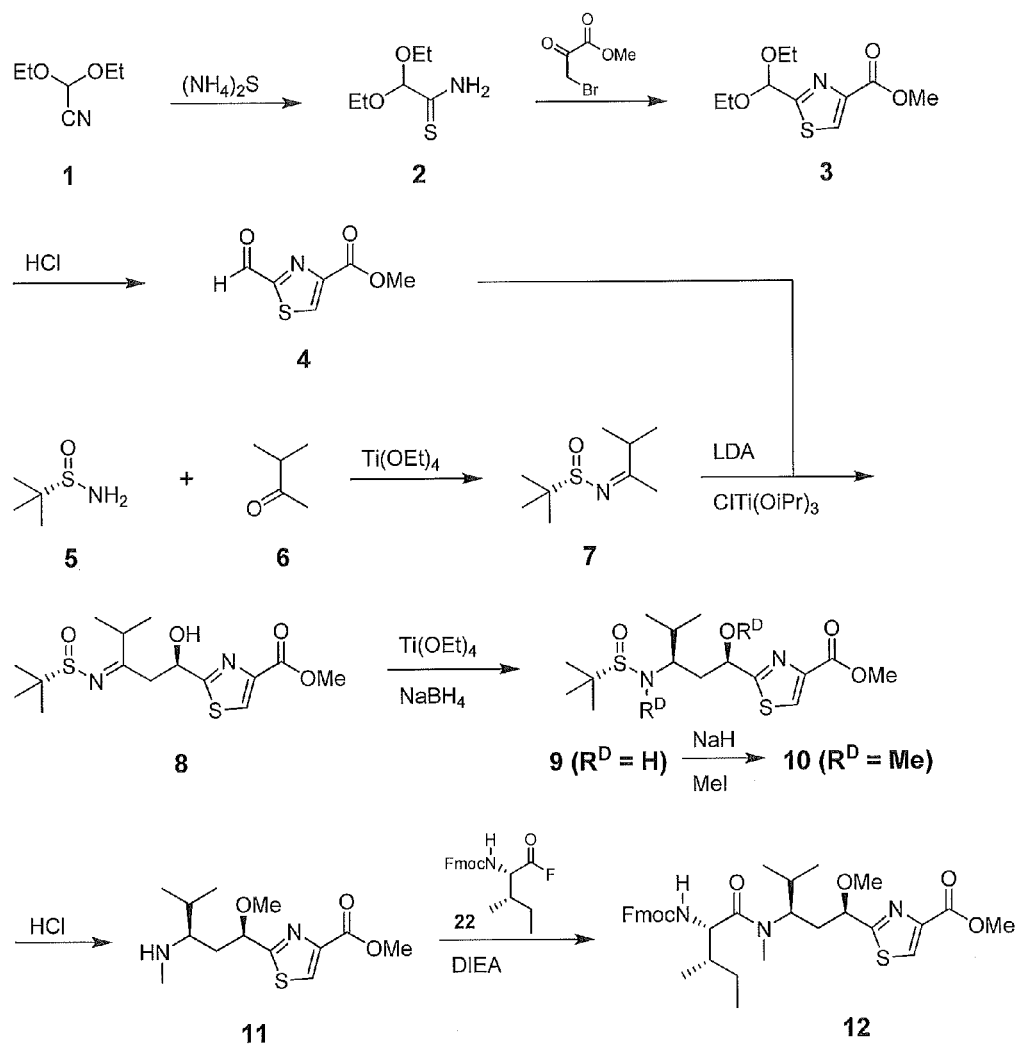
FIGS. 1a and 1b depict, in combination, Scheme 1 for making compounds of this invention.
Figure 1B:
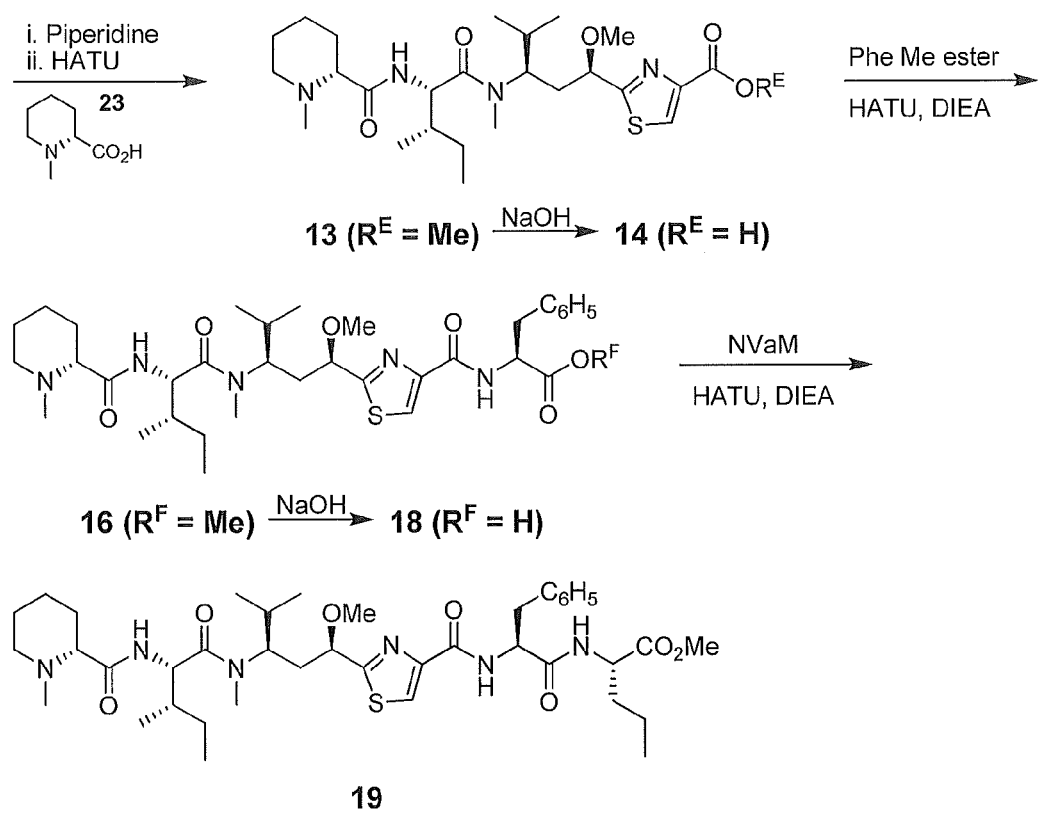

Scheme 1 (FIGS. 1a and 1b) depicts a method for making compounds of this invention.

Thioamide 2

2,2-Diethoxyacetonitrile 1 (25 g, 193 mmol) was mixed with $(NH_4)_2S$ (40 mL, 265 mmol, 45% aq. solution in) in 300 mL of methanol (MeOH) at room temperature (RT). After keeping the reaction mixture overnight, it was concentrated under vacuum and the residue was taken up in ethyl acetate (EtOAc). The EtOAc solution was washed with saturated $NaHCO_3$ solution then brine and dried over anhydrous $Na_2SO_4$. The EtOAc was evaporated to give thioamide 2 (26 g, 159 mmol, 82%) as a white solid. $^1H$ NMR (400 MHz, $CDCl_3$) δ 5.01 (s, 1H), 3.67 (m, 4H), 1.22 (t, J=7.2 Hz, 6H).

Methyl 2-(diethoxymethyl)thiazole-4-carboxylate 3

100 g of molecular sieves (3A) was added to a reaction mixture of thioamide 2 (25 g, 153 mmol) and methyl bromopyruvate (20 mL, 163 mmol) in 300 mL of MeOH. After the mixture was refluxed for 1.5 h, it was cooled and filtered through CELITE™. The filtrate was concentrated and passed through a column (dichloromethane (DCM):EtOAc, 8:1) to give thiazole carboxylate 3 (34.5 g, 140 mmol, 91%) as a solid, which was used for next step without further purification.

Methyl 2-formylthiazole-4-carboxylate 4

Thiazole-4-carboxylate 3 (30 g, 122 mmol) was dissolved in 300 mL of acetone, to which was added aqueous HCl (21 mL, 2M). After keeping the reaction mixture at RT for overnight, the reaction mixture was heated up and kept at 60° C. for 2 h. The reaction mixture was then cooled and evaporated under vacuum to give a residue which was taken up in 200 mL of DCM. DCM solution was then washed with saturated $NaHCO_3$ solution and then brine and dried over anhydrous $Na_2SO_4$. DCM solution was filtered and concentrated under vacuum to give the concentrated solution which was triturated by ether to give methyl 2-formylthiazole-4-carboxylate 4 (14 g, 82 mmol, 54% for two steps) as a white solid. $^1HNMR$ (400 MHz, $CDCl_3$) δ 133-8-p 110.16 (d, J=1.3 Hz, 1H), 8.53 (d, J=1.3 Hz, 1H), 4.01 (s, 3H).

Sulfinimine 7

(S)-2-Methylpropane-2-sulfinamide 5 (7.3 mL, 68 mmol) was dissolved in 100 mL tetrahydrofuran (THF), to which was added $Ti(OEt)_4$ (27 mL, 130 mmol) and 3-methyl-2-butanone 6 (8 g, 41 mmol) at RT. The reaction mixture was refluxed overnight and then cooled and added to a brine solution. The resultant mixture was filtered and the cake was washed with EtOAc. The organic phase was concentrated to give a residue which was subjected silica gel column chromatography (DCM:EtOAc, 4:1) to give sulfinimine 7 (9.5 g, 37 mmol, 75%) as an oil. $^1HNMR$ (400 MHz, $CDCl_3$) δ 2.53 (m, 1H), 2.29 (s, 3H), 1.22 (s, 9H), 1.12 (d, J=4.2 Hz, 3H), 1.10 (d, J=4.2 Hz, 3H) MS (ES+) m/z, calculated: m+1, 190.12. found, 190.

Compound 8

Lithium diisopropyl amide ("LDA," 60 mL, 108 mmol, 1.8M) was added to 200 mL of ether at −78° C. followed by the addition of sulfinimine 7 (18.9 g, 100 mmol) in 200 mL ether and the resultant reaction mixture was stirred for 40 min. $ClTi(OiPr)_3$ (203 mmol, 48.4 mL) was added to the reaction mixture and the solution was stirred for 60 min. A solution of methyl 2-formylthiazole-4-carboxylate 4 (12.5 g, 72.6 mmol) in 180 mL of THF was added slowly to the reaction mixture. After another 2 h at −78° C., a mixture of acetic acid and THF (⅕ v/v, 4.9 mL) was added. The mixture was warmed to 5° C. over 1 h and then poured into brine solution. The desired product was then extracted from the brine solution with ether and EtOAc solution. The organic phase was then dried over anhydrous MgSO$_4$, filtered and evaporated. The residue was passed through 2 columns (DCM:EtOAc and hexane:EtOAc) to give compound 8 (19.6 g, 54 mmol, 75%) as an oil. MS (ES+) m/z, calculated: m+1, 361.12. found, 361.

Compound 9

A solution of compound 8 (19 g, 52.7 mmol) in 200 mL of THF was cooled to −78° C., after which Ti(OEt)$_4$ (21.7 mL, 105 mmol) was added slowly. After 60 min, when the solution became clear, NaBH$_4$ (31 mmol, 1.17 g) was added, after 2 h (longer reaction time caused reduction of the ester) 10 mL MeOH was added. The mixture was then warmed to 0° C., poured into 1 mL HOAc in a lot of ice. The mixture was filtered and the cake was washed with EtOAc. After separation, the organic phase was dried with Na$_2$SO$_4$ and evaporated. The final residue was passed through a column (DCM:EtOAc, 1:4) to give compound 9 (19 g, 52 mmol, 99%) as an oil. $^1$HNMR (400 MHz, CDCl$_3$) δ 8.1 (s, 1H), 5.54 (d, J=6.7 Hz, 1H), 5.16 (m, 1H), 3.92 (s, 3H), 3.42 ((m, 1H), 3.32 (d, J=8.4 Hz, 1H), 2.25 (m, 1H), 1.88 (m, 1H), 1.68 (m, 1H), 1.26 (s, 9H), 0.91 (d, J=6.8 Hz, 3H), 0.87 (d, J=6.7 Hz, 3H). $^{13}$CNMR (100 MHz, CDCl$_3$) δ 177.9, 162.1, 146.6, 127.7, 67.9, 58.6, 56.4, 52.5, 40.8, 33.9, 23.1, 19.8, 17.4. MS (ES+) m/z, calculated: m+1, 363.13. found, 363.

Dimethylated Compound 10

Sodium hydride (9.69 mmol, 60%, 387 mg) was added to a solution of compound 9 in 6 mL N,N-dimethylformamide (DMF) at 5° C. followed by methyl iodide (607 uL, 9.7 mmol) after 60 minutes. After stirring the reaction mixture for 3 h, the mixture was poured into ice-cooled saturated NH$_4$Cl solution. Ethyl ether was added and the organic layer was washed with brine, dried over anhydrous MgSO$_4$ and concentrated to give a residue. The residue was passed through a column (hexane:EtOAc 1:4) to give dimethylated compound 10 (314 mg, 0.805 mmol, 33%) as a liquid. $^1$HNMR (400 MHz, CDCl$_3$) δ 8.17 (s, 1H), 4.87 (dd, J=11.0 Hz, J=2.5 Hz, 1H), 3.94 (s, 3H), 3.50 (s, 3H), 3.40 (m, 1H), 2.58 (s, 3H), 1.99 (m, 1H), 1.83 (m, 2H), 1.25 (s, 9H), 0.98 (d, J=6.8 Hz, 3H), 0.95 (d, J=6.7 Hz, 3H) MS (ES+) m/z, calculated: m+1, 391.16. found, 391.

Monomethyl Amine 11

Aqueous HCl (4N, in dioxane, 0.5 mL) was added to a solution of dimethylated compound 10 (370 mg, 0.95 mmol) in 5 mL MeOH. After stirring the reaction mixture for 60 min, it was evaporated under vacuum to give monomethyl amine 11 (362 mg) as its HCl salt, which was used for next step without further purification. MS (ES+) m/z, calculated: m+1, 287.14. found, 287.

Amide 12

Monomethyl amine 11 (362 mg, 1.12 mmol), Fmoc compound 22 (prepared per Wipf et al. 2007; 1.2 g, 3.38 mmol) and N,N-diisopropylethylamine (DIEA, 976 uL, 5.6 mmol) were mixed in 5 mL DMF at RT. After stirring for 24 h, the mixture was concentrated and the residue was dissolved in EtOAc. The organic phase was washed with NaHCO$_3$, brine, dried over anhydrous MgSO$_4$ and concentrated to give a residue. The residue was passed through a column (hexane:EtOAt:MeOH 7:3:0.6) to give amide 12 (466 mg, 0.75 mmol, 67%) as an oil. (ES+) m/z, calculated: m+1, 622.2. found, 622.

Compound 13

Amide 12 (466 mg, 0.75 mmol) was dissolved in 8 mL DCM containing 5% piperidine at RT. After 1 h, the mixture was evaporated under vacuum and the residue was passed through a column to give an oil (150 mg) which was then mixed with(D)-N-methyl pipecolinic acid 23 ("D-Mep," prepared per Peltier et al., 2006; 50 mg, 0.35 mmol), N,N,N',N'-tetramethyl-O-(7-azabenzotriazol-1-yOuronium hexafluorophosphate ("HATU," 126 mg, 0.33 mmol), DIEA (152 uL, 0.84 mmol) in 2 mL DCM. After stirring for 2.5 h, the solvent was evaporated to give a residue which was dissolved in EtOAc. The organic phase was then washed with saturated NaHCO$_3$, brine, dried over anhydrous MgSO$_4$ and concentrated to give a residue. The residue was passed through a column (DCM:MeOH 0-10%) to give compound 13 (99 mg, 0,188 mmol, 25%) as an oil. MS (ES+) m/z, calculated: m+1, 525.3. found, 525.

Acid 14

Compound 13 (99 mg, 0.18 mmol) was dissolved in a 3 mL mixture of MeOH and water (3:1 v:v), to which was added NaOH (370 uL, 0.37 mmol, 1M). After stirring for two h, the reaction mixture was neutralized and concentrated to give a residue. The residue was passed through a C-18 column (water (1% trifluoroacetic acid ("TFA")):acetonitrile (ACN) (1% TFA), 0-100%) to give acid 14 (78 mg, 0.125 mmol, 69%) as a TFA salt. MS (ES+) m/z, calculated: m+1, 511.29. found, 511.

Compound 15

DIEA (24 uL, 137 μmol) was added to a solution of acid 14 (9 mg, 14.4 umol, TFA salt) and HATU (6 mg, 15 umol) in DMF (0.5 mL) at RT. After all of acid 14 was activated (monitored by HPLC), tubuphenylalanine (prepared per Peltier et al. 2006; 6.5 mg, 27 umol, HCl salt) was added. After stirring for 20 mins, the reaction mixture was passed through a C-18 column (water (1% TFA):ACN (1% TFA), 0-100%) to give compound 15 (2.5 mg, 3 umol, 21%) as a white TFA salt. MS (ES+) m/z, calculated: m+1, 700.4. found, 700.

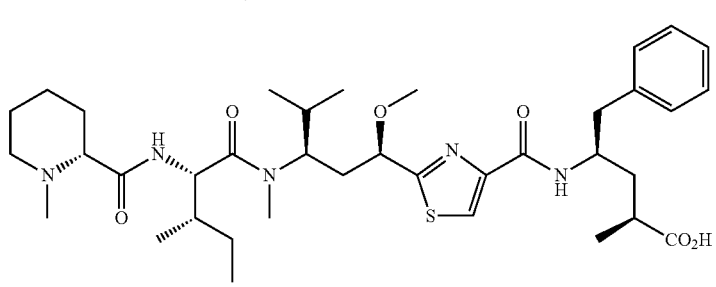

15

Compound 16

DIEA (20 uL, 0.11 mmol) was added to a solution of acid 14 (12 mg, 0.019 mmol, TFA salt), phenylalanine methyl ester (5.3 mg, 0.024 mmol, as HCl salt) and HATU (11.4 mg, 0.03 mmol) in 0.5 mL DMF. After 30 min, the reaction mixture was passed through a C-18 column (water (1% TFA):ACN (1% TFA) 0-100%) to give compound 16 (4.2 mg, 0.005 mmol, 26%) as a white TFA salt. MS (ES+) m/z, calculated: m+1, 672.89. found, 672.5. Compound 16 is also referred to as compound (III-c) hereinabove.

Compound 17

DIEA (7 uL, 0.04 mmol) was added to a solution of acid 14 (5 mg, 0.008 mmol), norvaline methyl ester ("NVaM," 2 mg, 0.012 mmol) and HATU (4.5 mg, 0.012 mmol) in DMF. After stirring the reaction mixture for 30 min the crude mixture was passed through a C-18 column (water (1% TFA):ACN (1% TFA) 0-100%) to give compound 17 (1.3 mg, 0.0017 mmol, 21%) as a white TFA salt. MS (ES+) m/z, calculated: m+1, 624.85. found, 624.5. Compound 17 is also referred to as compound (III-e) hereinabove.

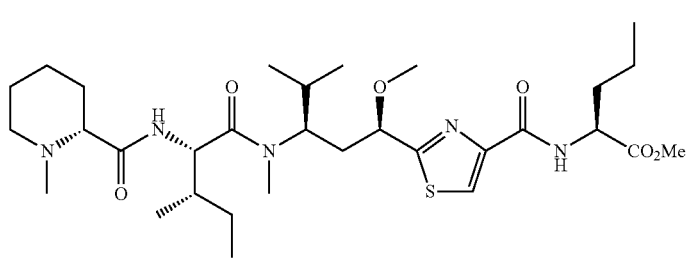

Acid 18

Aqueous NaOH (75 uL, 0.75 mmol, 10M) was added to a solution of compound 16 (168 mg, 0.25 mmol) in a mixture of MeOH and THF. After stirring overnight, the mixture was neutralized and lyophilized to dryness. The solid was used for next step without further purification. MS (ES+) m/z, calculated: m+1, 658.36. found, 658.4. Acid 18 is also referred to as compound (III-o) hereinabove.

Norvalyl Amide 19

DIEA (5, uL, 0.03 mmol) was added to a solution of acid 18 (5 mg, 0.006 mmol), HATU (3.5 mg, 0.009 mmol) and NVaM (1.5 mg, 0.009 mmol) in DMF. After stirring for 30 min, the reaction mixture was passed through a C-18 column (water (1% TFA):ACN (1% TFA) 0-100%) to give norvalyl amide 19 (2.2, 0.0025 mmol, 40%) as a white TFA salt. MS (ES+) m/z, calculated: m+1, 772.02. found, 771.5. Norvalyl amide 19 is also referred to as compound (III-f) hereinabove.

Compounds 24, 25, and 26

These three compounds were synthesized from acid 14 or 18 using procedures analogous to those described above. The products were all purified by a C-18 column (water (1% TFA):ACN (1% TFA) 0-100%). The yields varied from 25-50%. Compound 24: MS (ES+) m/z, calculated: m+1, 743.4. found 743. Compound 25: MS (ES+) m/z, calculated: m+1, 686.39. found 686.5. Compound 26: MS (ES+) m/z, calculated: m+1, 700.40. found 700.5.

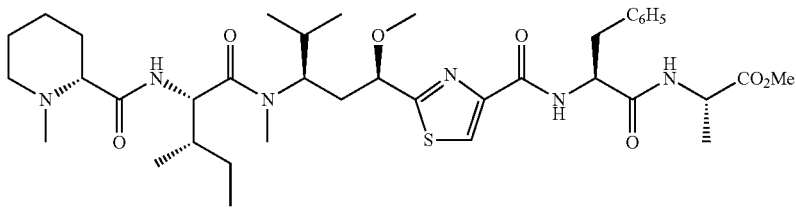

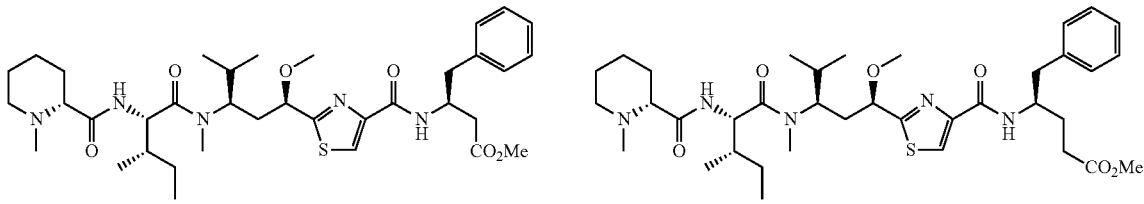

Compound 24 is also referred to as compound (III-g) hereinabove.

Compound 26a

Compound 14 was coupled with Ala-Phe OMe following the same procedure as described for compound 16. The product was purified by a C-18 column (water (1% TFA):ACN (1% TFA), 0-100%). MS (ES+) m/z, calculated: m+1, 743. found 743.4. Compound 26a is also referred to as compound (III-1) hereinabove.

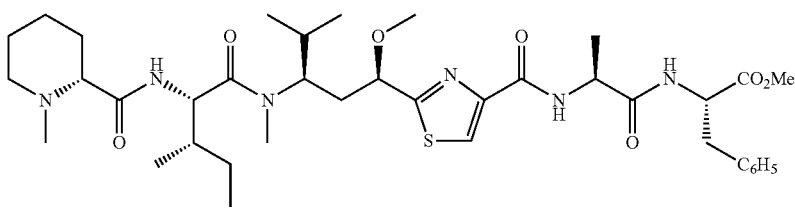

Example 2

Scheme 2

Figure 2:
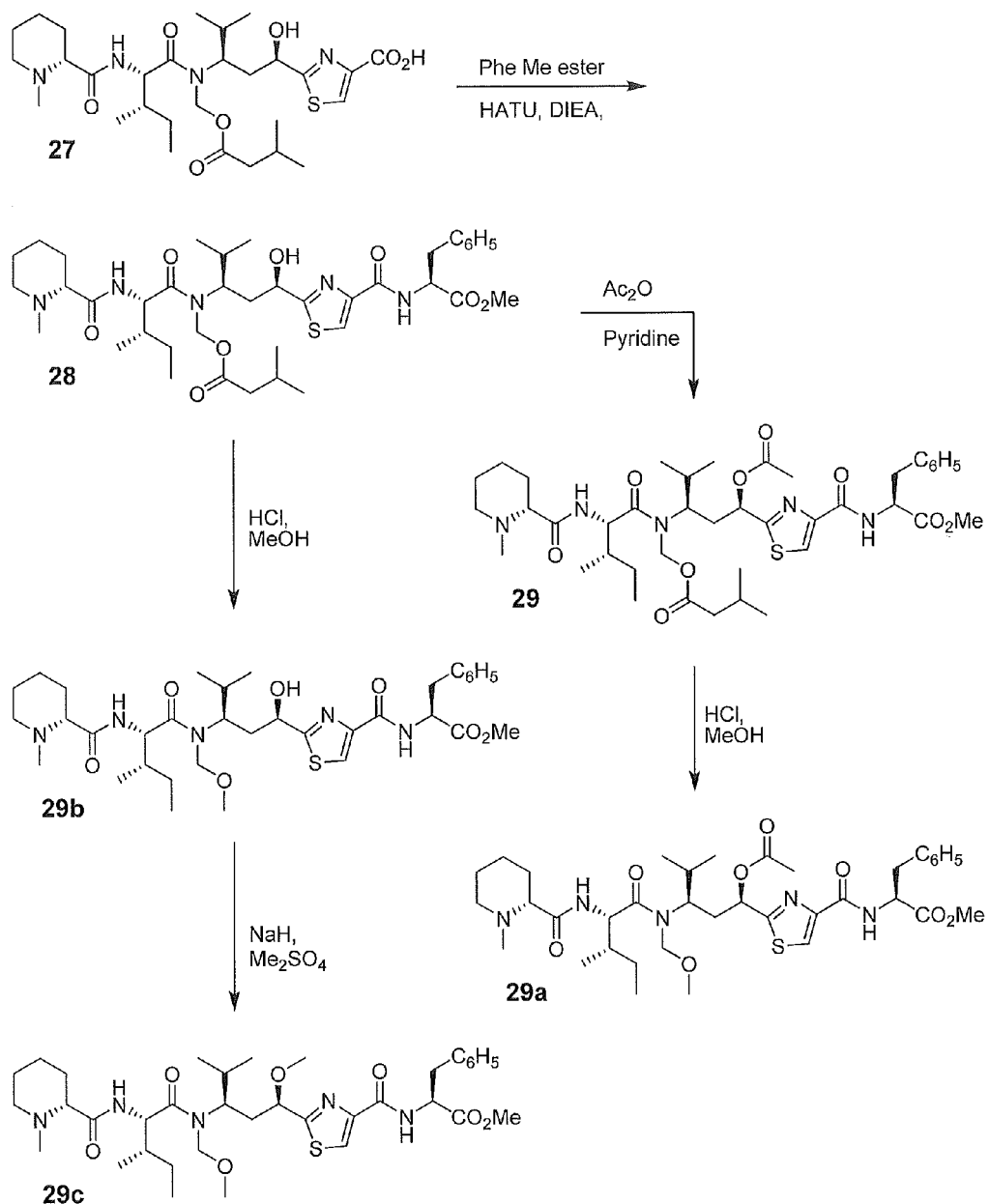
FIGS. 2 and 3 depict Schemes 2 and 3, respectively, also for making compounds of this invention.

This example describes the synthesis of compounds shown in Scheme 2 (FIG. 2).

Compound 28

Phenylalanine methyl ester (10 mg, 46.5 μmol) and HATU (14.7 mg, 38.6 umol) were added to a solution of compound 27 (prepared per Peltier et al., 2006; 10 mg, 15.5 μmol, formate salt) in 0.5 mL DMF followed by DIEA at RT. After stirring for 30 minutes, DMSO (2 mL) was added and the reaction mixture was directly subjected to a C-18 column (water (5 mM ammonium formate, pH 7.2):ACN 0-100%), to give compound 28 (3.2 mg, 25%) as a white solid (formate salt). MS (ES+) m/z, calculated: m+1, 758.41. found 758.4. Compound 28 is also referred to as compound (III-h) hereinabove.

Compound 29

Acetic anhydride (30 μL, 290 μmol) was added to a solution of compound 28 (3.2 mg, 3 μmol, formate salt) in 0.5 mL pyridine at 0° C. After stirring for 24 h, solvent was was evaporated from the reaction mixture and the residue was passed through a regular silica column (DCM:MeOH 0-10%) to give compound 29 (2.0 mg, 83%) as an oil. MS (ES+) m/z, calculated: m+1, 800.42. found 800.4. Compound 29 is also referred to as compound (III-i) hereinabove.

O-Acetyl, N,O-acetal 29a

Compound 29 (2 mg, 2.4 μmol) was dissolved in 0.5 mL MeOH, to which was added a drop of 4N HCl in dioxane. After stirring the reaction mixture overnight at RT, the mixture was concentrated and the residue was dissolved in DMSO, which was then passed through a C-18 column (water (20 mM ammonium formate, pH 6.1): ACN (0-100%) to give O-acetyl, N,O-acetal 29a (1.38 mg, 75%) as a white solid (formate salt) after lyophilization. MS (ES+) m/z, calculated:

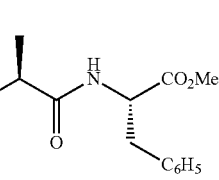

m+1, 730. found 730.4. O-Acetyl, N,O-acetal 29a is also referred to as compound (III-m) hereinabove.

N,O-Acetal 29b

Compound 28 (5 mg, 6 umol) was dissolved in MeOH, to which was added 1 drop of 4N HCl in dioxane. After stirring the reaction mixture for 24 hrs, the solution was concentrated and used for next step reaction without further purification. MS (ES+) m/z, calculated: m+1, 687. found 688.4. N,O-Acetal 29b is also referred to as compound (III-n) hereinabove.

O-Methyl, N,O-acetal 29c

N,O-Acetal 29b (about 5 mg, 7.2 umol) was dissolved in DMF, to which was added dimethylsulfate (3 μL, 37 μmol) and NaH (2 mg, 50 μmol, 60% in mineral oil) at 0° C. After 1 h, the mixture was taken up in DMSO and passed through a C-18 column (water (20 mM ammonium formate, pH 6.1): ACN (0-100%) to give O-methyl, N,O-acetal 29c as a semisolid (0.31 mg, 5%; mixture containing an unidentified compound of same MW). MS (ES+) m/z, calculated: m+1, 702. found 702.4. O-methyl, N,O-acetal 29c is also referred to as compound (III-k) hereinabove.

Example 3

Scheme 3

Figure 3:
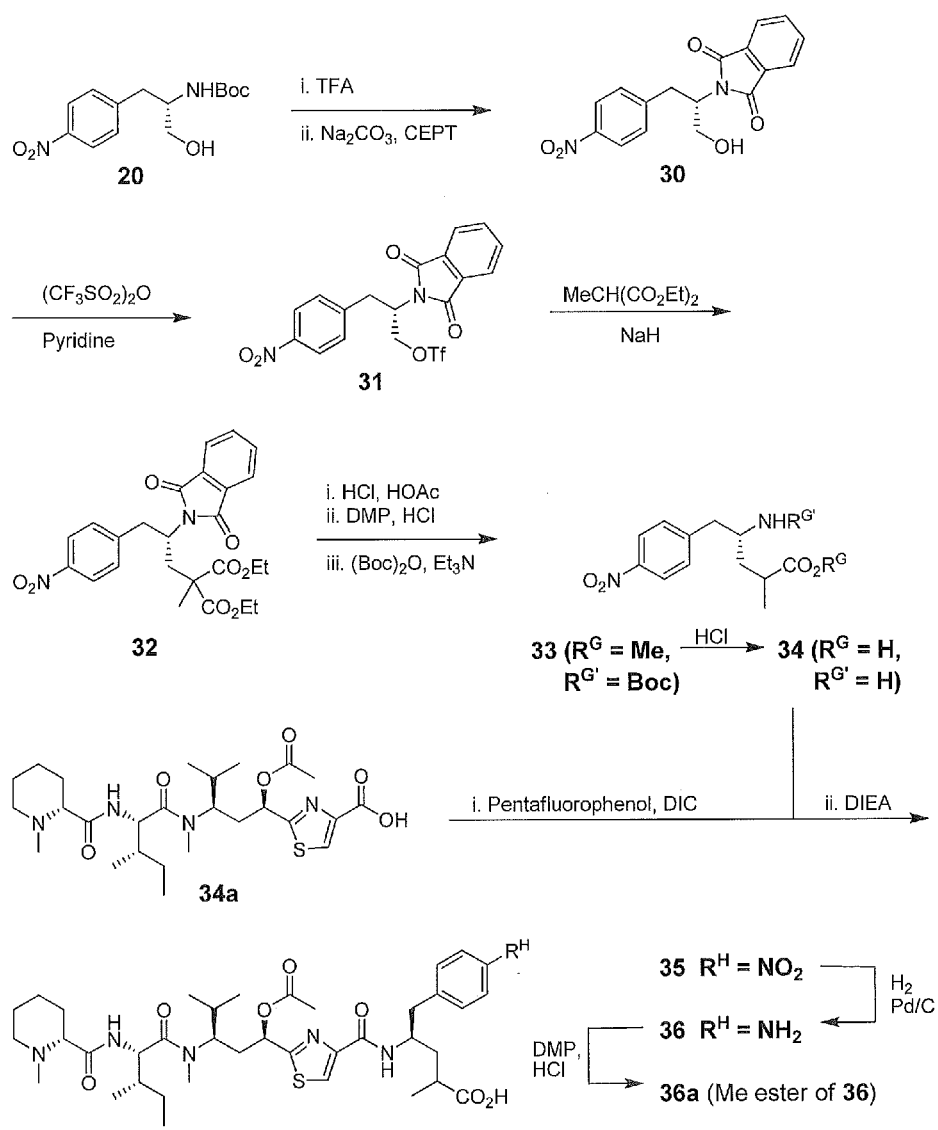

Scheme 3 (FIG. 3) shows a procedure for making compounds according to formula (II-b).

Alcohol 30

TFA (171 mL) was added to a solution of (S)-tert-butyl-1-hydroxy-3-(4-nitrophenyl)propan-2-ylcarbamate 20 (Erlanson et al., U.S. Pat. No. 7,214,487 B2; 13.9 g, 46.9 mmol) in DCM (272 mL) at 0° C. The reaction mixture was warmed to RT and reaction was allowed to proceed for 25 minutes. The solution was concentrated to afford 9.2 g of crude (S)-2-amino-3-(4-nitrophenyl)propan-1-ol as a white solid. To a solution of this crude product and sodium carbonate (12.4 g, 117.3 mmol) in THF (87 mL) and water (87 mL) was added N-carbethoxyphthalimide ("CEPT," 12.3 g, 56.3 mmol). After the reaction mixture was stirred at RT for 4 h, EtOAc (150 mL) was added. The aqueous phase was extracted with EtOAc. The combined organic layers were washed with brine, dried over anhydrous $Na_2SO_4$, filtered and concentrated under vacuum to give a crude residue which was purified by flash chromatography eluting from silica gel with a gradient of 0-100% EtOAc in hexanes to give 12.3 g of alcohol 30. MS: (+) m/z 327.0 (M+1).

Triflate 31

To a solution of alcohol 30 (1 g, 3.06 mmol) in anhydrous DCM (18 mL) was added pyridine (0.274 mL, 3.36 mmol) at −78° C. After the reaction mixture was stirred at −78° C. for 5 min, trifluoromethanesulfonic anhydride (0.568 mL, 3.36 mmol) was added. The reaction mixture was stirred at −78° C. for 45 min, and then at RT for 45 min. After the precipitate was filtered off, the filtrate was purified by flash chromatography eluting from silica gel with DCM to yield 0.84 g of triflate 31. $^1$H NMR (400 MHz, $CDCl_3$) δ 8.10 (2H, d, J=8.8 Hz), 7.81 (2H, m), p 7.74 (2H, m), 7.36 (2H, J=8.8 Hz), 5.13 (1H, t, J=10.0 Hz), 4.99 (1H, m), 4.80 (1H, dd, J=4.8, 5.6 Hz), 3.52 (1H, dd, J=3.2, 11.2 Hz), and 3.27 (1H, dd, J=5.6, 8.8 Hz).

Diester 32

Diethyl methylmalonate (0.71 mL, 4.12 mmol) was added dropwise to a suspension of sodium hydride (0.161 g, 60% dispersion in mineral oil, 4.03 mmol) in anhydrous THF (4.7 mL) at 0° C. The reaction mixture was stirred at 0° C. for 10 min, and then at RT for 10 min. The resulting solution was added slowly to a solution of triflate 31 (0.84 g, 1.83 mmol), in anhydrous THF (9.4 mL) at 0° C. After the reaction mixture was stirred at 0° C. overnight, saturated $NH_4Cl$ aqueous solution (20 mL) was added. The aqueous solution was extracted with EtOAc, and the combined organic layers were washed with brine, dried over $MgSO_4$, filtered, and concentrated under vacuum to give a residue. The crude product was purified by flash chromatography eluting from silica gel with a gradient of 0-50% EtOAc in hexanes to afford 0.57 g of diester 32. MS: (+) m/z 483.3 (M+1).

Monoester 33

A solution of diester 32 in 6 N HCl (10 mL) and acetic acid (10 mL) was heated at 145° C. for 2 days. The organic solution was concentrated to afford 0.41 g of the hydrochloride salt of the crude (R)-4-amino-2-methyl-5-(4-nitrophenyl) pentanoic acid as a white solid.

2,2-Dimethoxypropane ("DMP," 4 mL, 32.6 mmol) was added to a solution of the hydrochloride salt of the crude product and concentrated HCl (1 mL) in anhydrous MeOH (20 mL). The reaction mixture was heated at 60° C. overnight. The organic solution was concentrated to afford 0.43 g of the hydrochloride salt of the crude (R)-methyl 4-amino-2-methyl-5-(4-nitrophenyl)pentanoate as a white solid.

Triethylamine (0.44 mL, 3.1 mmol) was added to a solution of the hydrochloride salt of the crude (R)-methyl 4-amino-2-methyl-5-(4-nitrophenyl)pentanoate and di-tert-butyl dicarbonate (0.369 g, 1.69 mmol) in ACN (10 mL) at RT. After the reaction mixture was stirred at RT for 4 h, the solvent was evaporated. Water (20 mL) was added, and the aqueous solution was extracted with EtOAc. The combined organic layers were washed with brine, dried over $Na_2SO_4$, filtered, and concentrated. The crude product was purified by flash chromatography eluting from silica gel with a gradient of 0-30% EtOAc in hexanes to afford 0.31 g of monoester 33 as a colorless oil. MS: (+) m/z 267.3 (M-99).

Carboxylic Acid 34

A solution of monoester 33 (0.31 g, 0.846 mmol) in 6 N HCl was heated at 130° C. for 1.5 h. The organic solution was concentrated to afford 0.244 g of carboxylic acid 34 as a white solid. MS: (+) m/z 253.1 (M+1).

Nitro Acid 35

Compound 34a (80.4 mg, 0.149 mmol, prepared per Patterson et al. 2008) was added to a 0.2 M solution of pentafluorophenol (41.1 mg, 0.224 mmol) and N,N'-diisopropylcarbodiimide ("DIC," 0.0255 mL, 0.164 mmol) in DCM (0.76 mL) at 0° C. The reaction mixture was warmed to RT and stirred at RT overnight. The solvent was evaporated. EtOAc (18 mL) was added and the crude product was filtered, with rinsing of the reaction vessel with EtOAc. The filtrate was concentrated under reduced pressure and the crude material was used without further purification. DMF (0.6 mL) was added to the crude product, followed by carboxylic acid 34 (0.129 g, 0.448 mmol) and DIEA (0.13 mL, 0.745 mmol). The reaction mixture was stirred at RT overnight and the solvent was evaporated off. The crude product was purified by flash chromatography eluting from silica gel with a gradient of 10-20% MeOH in DCM containing 1% $NH_4OH$ to afford 0.11 g of nitro acid 35 as a white solid. MS: (+) m/z 773.4 (M+1).

Amino Acid 36

A solution of nitro acid 35 (0.11 g, 0.142 mmol) and palladium on carbon (10%, 15 mg) in MeOH (5 mL) was stirred under a hydrogen atmosphere for 4 h. The catalyst was filtered off, and the filtrate was concentrated to afford 91 mg of amino acid 36 as a white solid. MS: (+) m/z 743.5 (M+1) Amino acid 36 is also referred to as compound (III-b) hereinabove.

Methyl Ester 36a

HCl (1 drop, 37%) was added to a solution of amino acid 36 (1.9 mg, 2.5 mmol) and 2, 2-dimethoxypropane ("DMP," 0.05 mL, 0.41 mol) in MeOH (0.5 mL). The reaction mixture was stirred at RT for 2 h and then concentrated. The crude product was purified by preparative HPLC to afford 1.7 mg of methyl ester 36a as a white solid. MS: (+) m/z 757.5 (M+1). Ester 36a is also depicted in this specification by formula (III-t).

Example 4

Scheme 4

Figure 4:
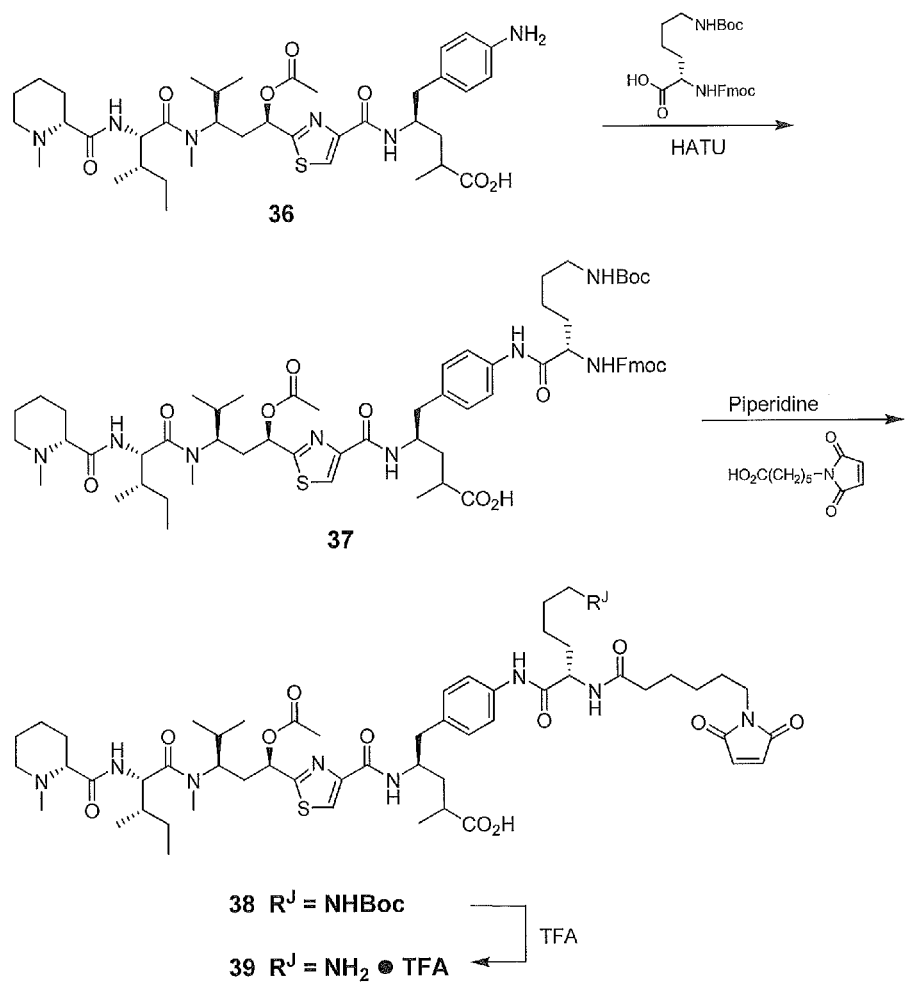
FIG. 4 depicts a Scheme 4 suitable for attaching a peptidyl linker and a maleimide reactive group to compounds of this invention.

Scheme 4 (FIG. 4) shows a method for attaching peptidyl linkers and reactive functional groups to compounds of this invention, ready for conjugation.

Compound 37

A solution of DIEA, Fmoc-Lys(Boc)-OH (17.3 mg, 0.037 mmol), and HATU (12.8 mg, 0.0336 mmol) in DMF (0.3 mL) was stirred at RT for 5 min. The pH of the solution was maintained between 8 and 9. Then a solution of amino acid 36 (25 mg, 0.0336 mmol) in DMF (2 mL) and DIEA was added to the reaction mixture, maintaining the pH between 8 and 9. After stirring at RT for 15 min, saturated $NH_4Cl$ solution (5 mL) was added to quench the reaction. The aqueous solution was extracted with EtOAc, and the combined organic layers were dried, filtered, and concentrated. The crude product was purified by flash chromatography eluting from silica gel with a gradient of 0-20% MeOH in DCM to afford 36.1 mg of compound 37. MS: (+) m/z 1193.6 (M+1).

Compound 38

Piperidine was added to a solution of compound 37 (36.1 mg, 0.0302 mmol) in DMF (2 mL), maintaining pH between 9 and 10. After stirring at RT for 20 min, the organic solution was concentrated to afford 29.3 mg of the crude free α-amino compound.

DIEA was added to a solution of 6-maleimidohexanoic acid (7.0 mg, 0.0332 mmol) and HATU (11.5 mg, 0.0302 mmol) in DMF (0.3 mL) maintaining the pH between 8 and 9. The reaction mixture was stirred at RT for 5 min. Then DIEA and the crude free amino compound in DMF (2 mL) were added, maintaining the pH between 8 and 9. After the reaction mixture was stirred at RT for 15 min, the crude product was purified by preparative HPLC to afford 9.1 mg of compound 38 as a white solid. MS: (+) m/z 1164.6 (M+1).

Compound 39

TFA (1.5 mL) was added to a solution of compound 38 (9.1 mg, 0.0078 mmol) in DCM (1.5 mL). After the reaction mixture was stirred at RT for 15 min, the crude product was purified by preparative HPLC to afford 5.0 mg of the TFA salt of the desired compound 39 as a white solid. MS: (+) m/z 1064.8 (M+1). The free base structure of compound 39 is also shown hereinabove, as compound (VI-b). Some amide of compound 39 was also isolated as a by-product in its preparation. MS: (+) m/z 1063.6 (M+1). The amide is also depicted in this specification by formula (VI-q).

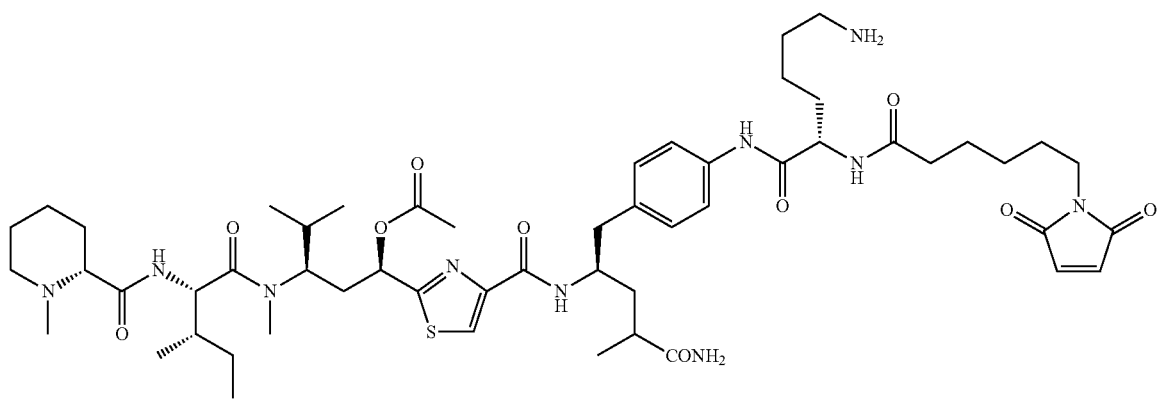

Amide of compound 39

Example 5

Scheme 5

Scheme 5 (FIG. 5) shows an alternative procedure for making compounds according to formula (II-b).

Amino Ester 42

4.0 N HCl in 1,4-dioxane (6.7 mL) was added to a solution of compound 41 (prepared per Patterson et al. 2008; 1 g, 2.66 mmol) in ethanol (17 mL). The reaction mixture was stirred at RT for 2 h, and then concentrated to afford 0.82 g of amino ester 42 as a white solid. MS: (+) m/z 273.3 (M+1).

Azido Ester 43

Oxalyl chloride (1.71 mL, 19.95 mmol) and DMF (0.33 mL, 4.26 mmol) were added to a solution of azido isoleucine (Lundquist et al., *Org. Lett.* 2001, 3, 781; 0.669 g, 4.26 mmol) in hexanes (176 mL). The reaction mixture was stirred at RT for 1 h, filtered, and concentrated to afford the acid chloride. The acid chloride and DIEA (2.32 mL, 13.3 mmol) were added to a solution of amino ester 42 (0.82 g, 2.66 mmol) in DCM (26.7 mL) at 0° C. The reaction mixture was allowed to warm to RT and stirred at RT overnight. Brine was added to quench the reaction, and the aqueous solution was extracted with EtOAc. The combined organic layers were dried over $Na_2SO_4$, filtered, and concentrated under vacuum. The crude product was purified by flash chromatography eluting from silica gel with a gradient of 0-50% EtOAc in hexanes to afford 0.86 g of azido ester 43 as a white solid. MS: (+) m/z 412.3 (M+1).

Triethylsilyl Compound 44

2,6-Lutidine (1.22 mL, 10.45 mmol) and triethylsilyl trifluoromethanesulfonate (1.14 mL, 5.02 mmol) were added to a solution of azido ester 43 (0.86 g, 2.09 mmol) in DCM (11 mL) at 0° C. The reaction mixture was allowed to warm to RT over 1 h, and then stirred at RT for an additional hour. Brine was added to quench the reaction, and the aqueous solution was extracted with EtOAc. The combined organic layers were dried, filtered, and concentrated. The crude product was purified by silica gel flash chromatography eluting with a gradient of 0-30% EtOAc in hexanes to afford 1.1 g of triethylsilyl compound 44. MS: (+) m/z 526.4 (M+1).

N-Methyl Compound 45

A solution of triethylsilyl compound 44 (1.04 g, 1.98 mmol) in THF (6.5 mL) was cooled at −45° C., and potassium hexamethyldisilazide (0.5 M in toluene, 4.75 mL, 2.37 mmol) was added. The resulting mixture was stirred for 20 min at −45° C. Methyl iodide (0.37 mL, 5.94 mmol) was added, and the reaction mixture was allowed to warm to RT over 4 h at which time the reaction was quenched with ethanol (10 mL). The crude product was diluted with EtOAc and washed with brine, and the aqueous layer was extracted with EtOAc. The combined organic layers were dried over anhydrous $Na_2SO_4$, filtered, and concentrated under vacuum. The crude product was purified by flash chromatography eluting from silica gel with a gradient of 0-30% EtOAc in hexanes to afford 0.91 g of N-methyl compound 45. MS: (+) m/z 540.4 (M+1).

Compound 46

A solution of N-methyl compound 45 (1.0 g, 1.85 mmol) in deoxygenated $AcOH/H_2O/THF$ (65 mL, 3:1:1, v/v/v) was stirred at RT for 36 h. Toluene (250 mL) was added and the solution was concentrated. The crude product was purified by flash chromatography eluting from silica gel with a gradient of 0-100% EtOAc in hexanes to afford 0.46 g of compound 46 as oil. MS: (+) m/z 426.3 (M+1).

Methyl Ether 47

Potassium hexamethyldisilazide ("KHMDS," 0.5 M in toluene, 2.54 mL, 1.27 mmol) was added to a solution of compound 46 (0.45 g, 1.06 mmol) in THF (5 mL) at −78° C. The reaction mixture was stirred for 20 min at −78° C. Methyl iodide (0.2 mL, 3.18 mmol) was added, and the reaction mixture was allowed to warm to −20° C. over 2 h at which time the reaction was quenched with saturated $NH_4Cl$ solution. The aqueous solution was extracted with EtOAc. The combined organic layers were dried over anhydrous $Na_2SO_4$, filtered, and concentrated under vacuum. The crude product was purified by flash chromatography eluting from silica gel with a gradient of 0-50% EtOAc in hexanes to afford 0.41 g of compound 47 as colorless oil. MS: (+) m/z 440.3 (M+1).

Compound 48

To a solution of D-Mep (0.45 g, 3.14 mmol) in EtOAc (10 mL) were added pentafluorophenol (0.64 g, 3.47 mmol) and N,N'-dicyclohexylcarbodiimide ("DCC," 0.72 g, 3.47 mmol). After the reaction mixture was stirred at RT overnight, the precipitate was filtered, and washed with EtOAc. To the resulting filtrate waa added compound 47 (0.46 g, 1.05 mmol) and palladium on carbon (10 wt %, 0.36 g). The reaction mixture was stirred under a hydrogen atmosphere overnight. The catalyst was filtered off, and then the filtrate was concentrated under vacuum. The crude product was purified by flash chromatography eluting from silica gel with a gradient of 0-5% MeOH in EtOAc to afford 0.43 g of compound 48 as colorless oil. MS: (+) m/z 539.4 (M+1).

Carboxylic acid 49

To a solution of compound 48 (0.43 g, 0.80 mmol) in deoxygenated 1,4-dioxane (8 mL) was added deoxygenated lithium hydroxide aqueous solution (0.6 M, 4 mL) at RT. The reaction mixture was stirred at RT for 2 h, and then concentrated under vacuum. The crude product was purified by flash chromatography eluting from silica gel with a gradient of 10-30% MeOH in DCM containing 1% $NH_4OH$ to afford 0.3 g of carboxylic acid 49 as a white solid. MS: (+) m/z 511.4 (M+1).

Nitro Acid 50

Carboxylic acid 49 (80 mg, 0.157 mmol) was added to a 0.2 M solution of pentafluorophenol (43.3 mg, 0.235 mmol) and DIC (0.0269 mL, 0.173 mmol) in DCM (0.8 mL) at 0° C. The reaction mixture was warmed to RT, and stirred at such temperature overnight. The solvent was evaporated. Ethyl acetate (18 mL) was added, and the crude product was filtered, with EtOAc rinse of the reaction vessel. The filtrate was concentrated under reduced pressure, and the crude material was used without further purification. DMF (0.6 mL) was added to the crude product, followed by carboxylic acid 34 (0.136 g, 0.47 mmol), and DIEA (0.137 mL, 0.785 mmol). The reaction mixture was stirred at RT overnight, and the solvent was then evaporated under vacuum. The crude product was purified by flash chromatography, eluting from silica gel with a gradient of 10-20% MeOH in DCM containing 1% $NH_4OH$ to afford 0.1 g of nitro acid 50 as a white solid. MS: (+) m/z 745.4 (M+1).

Amino Acid 51

A mixture of nitro acid 50 (0.1 g, 0.134 mmol) and palladium on carbon (10%, 14 mg) in MeOH (5 mL) was stirred under a hydrogen atmosphere for 4 h. The catalyst was filtered off, and the filtrate was concentrated under vacuum to afford 87.3 mg of amino acid 51 as a white solid. MS: (+) m/z 715.5 (M+1) Amino acid 51 is also referred to as compound (III-j) hereinabove.

Example 6

Scheme 6

Scheme 6 (FIG. 6) shows yet another procedure for making compounds according to formula (II-b).

Hydroxy Nitro Compound 52

Compound 27 (Scheme 2) (16.4 mg, 0.0275 mmol), was added to a 0.2 M solution of pentafluorophenol (7.6 mg, 0.0413 mmol) and DIC (0.0094 mL, 0.0606 mmol) in DCM (0.2 mL) at 0° C. The reaction mixture was warmed to RT, and stirred at RT overnight. The solvent was evaporated. EtOAc (3 mL) was added and the crude product was filtered, with rinsing of the reaction vessel with EtOAc. The filtrate was concentrated under reduced pressure, and the crude material was used without further purification. DMF (0.1 mL) was added to the crude product, followed by carboxylic acid 34 (Scheme 3) (20.8 mg, 0.083 mmol), and N,N-diisopropylethylamine (0.024 mL, 0.138 mmol). The reaction mixture was stirred at RT overnight, and the solvent was then evaporated. The crude product was purified by flash chromatography eluting from silica gel with a gradient of 0-10% MeOH in DCM to afford 14.9 mg of hydroxy nitro compound 52 as a white solid. MS: (+) m/z 831.5 (M+1).

Acetyl Nitro Compound 53

A 0.1 M solution of hydroxy nitro compound 52 (14.9 mg, 0.018 mmol) in pyridine (0.23 mL) was cooled at 0° C., and acetic anhydride (0.054 mL, 0.57 mmol) was added. The reaction mixture was allowed to warm to RT over 2 h, and stirred at RT for 24 h. The reaction mixture was cooled to 0° C., and 1:1 mixture of 1,4-dioxane and water was added. The reaction mixture was allowed to warm to RT, followed by stirring at this temperature for 12 h. The solvent was evaporated, and the residue was purified by preparative HPLC to afford 2.2 mg of acetyl nitro compound 53 as a white solid. MS: (+) m/z 873.2 (M+1).

Acetyl Amino Compound 54

A mixture of acetyl nitro compound 53 (2.2 mg, 0.0025 mmol) and palladium on carbon (10%, 1 mg) in methanol (0.2 mL) was stirred under a hydrogen atmosphere for 4 h. The catalyst was filtered off, and the filtrate was concentrated. The crude product was purified by preparative HPLC to afford 0.1 mg of acetyl nitro compound 54 as a white solid. MS: (+) m/z 843.2 (M+1). Acetyl amino compound 54 is also referred to as compound (III-a) hereinabove.

Example 7

Scheme 7

Scheme 7 (FIG. 7) shows yet another procedure for making compounds of this invention.

Compound 55

Compound 34a (Scheme 3) (70 mg, 0.13 mmol) was added to a 0.2 M solution of pentafluorophenol (35.9 mg, 0.195 mmol) and DIC (0.0223 mL, 0.143 mmol) in DCM (0.66 mL) at 0° C. The reaction mixture was warmed to RT and stirred at RT overnight. The solvent was evaporated. EtOAc(16 mL) was added and the crude product was filtered, with rinsing of the reaction vessel with EtOAc. The filtrate was concentrated under reduced pressure, and the crude material was used without further purification. DMF (0.5 mL) was added to the crude product, followed by p-nitrophenylalanine (82.0 mg. 0.39 mmol) and DIEA (0.114 mL, 0.65 mmol). The reaction mixture was stirred at RTovernight, and the solvent was then evaporated. The crude product was purified by flash chromatography eluting from silica gel with a gradient of 10-20% MeOH in DCM containing 1% NH$_4$OH to afford 65.2 mg of compound 55 as a white solid. MS: (+) m/z 731.0 (M+1).

Compound 56

A mixture of compound 55 (65.2 mg, 0.089 mmol) and palladium on carbon (10%, 9.4 mg) in MeOH (3 mL) was stirred under a hydrogen atmosphere for 4 h. The catalyst was filtered off, and the filtrate was concentrated to afford 33.8 mg of compund 56 as a white solid. MS: (+) m/z 701.2 (M+1). Compound 56 is also referred to as compound (III-d) hereinabove.

Example 8

Scheme 8

Scheme 8 (FIG. 8a) shows a method for making a compound according to formula (VIII-b), useful as an intermediate for making compounds of this invention.

Boc Ester 58

To a solution of amino ester 57 (Chem-Impex, 5 g, 19.18 mmol) and di-tert-butyl dicarbonate ("(Boc)$_2$O," Aldrich, 4.6 g, 21.10 mmol) in DMF (Acros, anhydrous, 50 mL), triethylamine ("TEA," Aldrich, 8.36 mL, 60 mmol) was added. The reaction mixture was stirred for 0.5 h. HPLC analysis showed reaction was completed. The reaction mixture was diluted with EtOAc (500 mL) and the organic layer was washed with water (200 mL) and then brine (200 mL), dried over anhydrous MgSO$_4$ and concentrated. The crude product was purified on 120 g CombiFlash column with 0-5% MeOH in DCM to yield white solid Boc ester 58 (5.6 g, 81%). $^1$HNMR (DMSO) δ 8.18 (d, 2H), 7.47 (d, 2H), 7.38 (d, 1H), 4.23 (m, 1H), 3.60 (s, 3H), 3.15 (m, 1H), 2.95 (m, 1H), 1.23 (s, 9H).

Alkene 59

To a solution of Boc ester 58 (230 mg, 0.68 mmol) in DCM (Acros, anhydrous, 2 mL) cooled to −78° C. in a dry ice-acetone, DIBAL (Aldrich, 1 M in DCM, 1 mL) was added slowly. The reaction mixture was stirred and warmed up to −20° C. over 3 h. (1-Ethoxycarbonylethyliden)-triphenylphosphoran (Aldrich, 492 mg, 1.36 mmol) was added. The reaction mixture was stirred at −20° C. for 1 h. The reaction mixture was diluted with EtOAc (100 mL) and the resultant organics was washed with water (50 mL) and then brine (50 mL), dried over anhydrous MgSO$_4$ and concentrated. The crude product was purified on 10 g COMBIFLASH™ column with 0-50% EtOAc in hexane to yield white solid alkene 59 (151 mg, 59%). $^1$HNMR (DMSO) δ 8.18 (d, 2H), 7.47 (d, 2H), 7.22 (d, 1H), 6.51 (d, 1H), 4.48 (m, 1H), 4.11 (q, 2H), 2.80-2.94 (m, 2H), 1.62 (s, 3H), 1.23 (s, 9H), 1.16 (t, 3H).

Aryl Amine 60

A solution of alkene 59 (148 mg, 0.39 mmol) in EtOH (Acros, anhydrous, 3 mL) and Pd on charcoal (Aldrich, 10%, 50 mg) was stirred under H$_2$ overnight. The reaction mixture was diluted with DCM (10 mL) and filtered through CELITE™. The filtrate was concentrated and the crude product was purified on 4 g COMBIFLASH™ column with 0-20% MeOH in DCM to yield aryl amine 60 as a white solid (102 mg, 75%). $^1$HNMR (DMSO) δ 7.18 (d, 2H), 7.11 (s, 2H), 6.71 (d, 1H), 3.98 (q, 2H), 3.51 (m, 1H), 2.57 (m, 2H), 2.41 (m, 1H), 1.63 (m, 1H), 1.37 (m, 1H), 1.29 (s, 9H), 1.09 (t, 3H), 0.99 (d, 3H), MS (ES+) m/z, calculated: m+1, 351.2. found 351.2.

Example 9

Scheme 9

Scheme 9 (FIG. 8b) shows another method for making a compound according to formula (VIII-b), useful as an intermediate for making compounds of this invention.

Amino Acid 61

A mixture of carboxylic acid 24 (Scheme 3, FIG. 3) (4.4 mg, 0.0025 mmol) and palladium on carbon (10%, 1 mg) in MeOH (0.5 mL) was stirred under a hydrogen atmosphere overnight. The catalyst was filtered off, and the filtrate was concentrated to afford 3.5 mg of amino acid 61 as a white solid. MS: (+) m/z 223.3 (M+1).

Example 10

Schemes 10, 11, and 12

Scheme 10 (FIG. 8c) shows another method for making a compound according to formula (VIII-b), useful as an intermediate for making compounds of this invention.

Compound 62

A mixture of monoester 33 (Scheme 3, FIG. 3) (0.34 g, 0.93 mmol) and palladium on carbon (10%, 50 mg) in methanol (20 mL) was stirred under a hydrogen atmosphere overnight. The catalyst was filtered off, and the filtrate was concentrated to afford 0.29 g of compound 62 as a white solid. MS: (+) m/z 237.3 (without Boc).

Scheme 11 (FIG. 9) illustrates how compounds according to formula (VIII-b) can be used to make compounds of this invention. Boc ester 62 is converted to Bpoc ester 62a by first protecting the aromatic amine group with an Fmoc group, treatment with TFA to remove the Boc group from the aliphatic amine group, treatment with carbonic acid α,α-dimethyl-p-phenylbenzyl phenyl ester (8C1) to install a Bpoc group there, and removal of the Fmoc group with piperidine. Bpoc ester 62a is coupled with carboxylic acid 63 with HATU to yield an intermediate ester that is then hydrolyzed with LiOH to produce compound 64. Hydrogenation to remove the Cbz protecting group from compound 64, followed by HATU-mediated coupling with 6-maleimidohexanoic acid and removal of the Bpoc group with acetic acid yields amino acid 65. Another HATU-mediated coupling with compound 34a (Scheme 3, FIG. 3) yields compound 66. Removal of the Boc protecting group with TFA affords compound 67, ready for conjugation.

Yet another mode of utilizing compounds of formula (VIII-b) is shown in Scheme 12 (FIG. 10). Starting from compound 34a, HATU-mediated coupling with compound 68 affords Boc ester 69. Removal of the Boc group with TFA and hydrolysis of the ester with LiOH affords amino acid 36, which can be elaborated as shown in Scheme 4 (FIG. 4) to prepare a composition suitable for conjugation.

Example 11

Compound 70

Compound 70

Tubulysin D (made per Peltier et al. 2006; 2 mg, 2.4 umol) was dissolved in MeOH at 0° C. To this solution was added a drop of HCl (0.1 M). After stirring the reaction mixture for overnight at RT the solution was evaporated under vacuum to give a residue that was passed through a short column (DCM:MeOH 0-10%) to give compound 70 (1.3 mg, 1.6 umol, 67%) as an oil. MS (ES+) m/z, calculated: m+1, 772.42. found, 772.

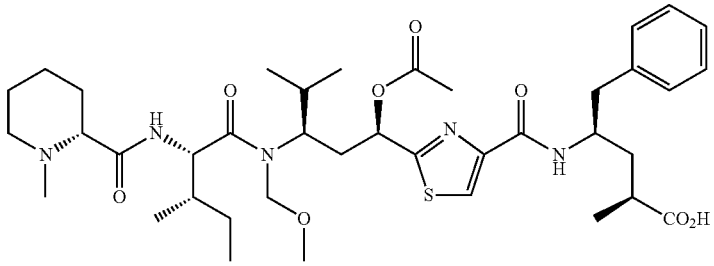

Those skilled in the art will appreciate that the general methodology of the Schemes can be adapted to make compounds of this invention other than those specifically described above. For example, compound 14 (same as compound 49) can be used to make numerous other compounds of this invention by coupling it with other replacements for the Tup subunit. As another example, by changing the reagents used with compound 9 (Scheme 1), compounds 44 and 46 (Scheme 5), variations on groups $R^2$ and $R^3$ in formula (II) beyond those specifically exemplified can be synthesized.

Example 12

Preparation of a Conjugate

This example describes the preparation of a conjugate of cytotoxin-linker construct (VI-b) and anti-CD70 monoclonal antibody 2H5 (Terrett et al., US 2009/0028872 A1; Coccia et al., WO 2008/074004 A2). It is representative of the procedure used in the preparation of other conjugates.

Anti-CD70 antibody 2H5 at ~5 mg/mL in 20 mM sodium phosphate, 50 mM NaCl, 100 μM DTPA, pH 7.5, was thiolated with a 13-fold molar excess of 2-iminothiolane. The thiolation reaction was allowed to proceed for 1 h at RT with continuous mixing.

Following thiolation, the antibody was buffer exchanged into conjugation buffer (50 mM HEPES, 5 mM glycine, 2 mM DTPA, pH 6.0) via a PD10 column (Sephadex G-25). The concentration of the thiolated antibody was determined at 280 nm. The thiol concentration was measured using a dithiodipyridine assay.

A 5 mM stock of construct (VI-b) in DMSO was added at a 3-fold molar excess per thiol of antibody and mixed for 90 min at RT. Following conjugation, 100 mM N-ethylmaleimide in DMSO was added at a 10-fold molar excess of thiol per antibody to quench any unreacted thiol groups. This quenching reaction was done for one h at RT with continuous mixing.

The anti-CD70 antibody drug conjugate was 0.2 μm filtered prior to cation-exchange chromatographic purification. The SP SEPHAROSE™ High Performance Cation Exchange column (CEX) was regenerated with 5 column volumes (CVs) of 50 mM HEPES, 5 mM glycine, 1M NaCl, pH 6.0. Following regeneration, the column was equilibrated with 3 CVs of equilibration buffer (50 mM HEPES, 5 mM glycine, pH 6.0). The conjugate was loaded and the column and was washed once with the equilibration buffer. The conjugate was eluted with 50 mM HEPES, 5 mM glycine, 200 mM NaCl, pH 6.0. The eluate was collected in fractions. The column was then regenerated with 50 mM HEPES, 5 mM glycine, 1M NaCl, pH 6.0 to remove protein aggregates and any unreacted (VI-b).

Fractions containing monomeric antibody conjugate were pooled. Antibody conjugate concentration and substitution ratios were determined by measuring absorbance at 280 and 252 nm.

The purified eluate pool was buffer exchanged into 30 mg/mL sucrose, 10 mg/mL glycine, pH 6.0, by dialysis. Dextran 40 was added to the sample at 10 mg/mL post-dialysis. The concentration and substitution ratio (SR) were determined by measuring absorbance at 280 and 252 nm. The SR was 2.2 moles of cytotoxin per mole of antibody.

Example 13

Proliferation Assays

This example generally describes the procedures used to assay the antiproliferative activity of compounds of this invention or their conjugates. Human tumor cell lines were obtained from the American Type Culture Collection (ATCC), P.O. Box 1549, Manassas, Va. 20108, USA, and cultured according to instruction from the ATCC. Cells were seeded at $1.0 \times 10^3$ or $1.0 \times 10^4$ cells/well in 96-well plates for 3 h for ATP assays or $^3$H thymidine assays, respectively. 1:3 serial dilutions of free (unconjugated) compounds or their conjugates were added to the wells. Plates were allowed to incubate for 24 to 72 h. The $^3$H thymidine plates were pulsed with 1.0 μCi of $^3$H-thymidine per well for the last 24 hours of the total incubation period, harvested, and read on a Top Count Scintillation Counter (Packard Instruments, Meriden, Conn.). ATP levels in the ATP plates were measured using the CELLTITER-GLO® Luminescent Cell Viability kit following the manufacturer's manual and read on a GLOMAX® 20/20 luminometer (both from Promega, Madison, Wis., USA). The $EC_{50}$ values—the concentration at which an agent inhibits or reduces cell proliferation by 50%—were determined using PRISM™ software, version 4.0 (GraphPad Software, La Jolla, Calif., USA).

Example 14

Cytotoxin In Vitro Activity

Using the $^3$H thymidine or the ATP luminescence assay, or both, the activities of compounds of this invention were assayed against the following cancer cell lines: HCT-15 (colorectal cancer, multi-drug resistant (MDR)); Hep3B (liver cancer); LNCaP (prostate cancer, androgen receptor positive (AR)); MDA-MB-231 (breast cancer, estrogen receptor, progesterone receptor, and Her2 negative (triple negative)); A2058 (melanoma); U-87 MG (glioblastoma); NCI-H460 (NSCLC); A549 (NSCLC); HPAC (pancreatic cancer, primary); PC3 (prostate cancer, AR⁻); BT474 (breast cancer, Her2 highly positive (Her2hi)); SKOV3 (ovarian cancer, Her2hi); 786-O (renal cancer); UO-31 (renal cancer, MDR); NCI-H740 (SCLC); DMS53 (SCLC); SK-BR3 (breast cancer, Her2hi); ZR-75 (breast cancer, estrogen receptor positive); OVCAR3 (ovarian cancer); HL-60 (APL); OVCAR8/Adr (ovarian cancer, MDR); CEM-C1 (ALL); Nomo-1 (AML); RPMI-8226 (MM)); Raji (lymphoma); SW-480 (colorectal cancer, metastatic); SW-620 (colorectal cancer); and H226 (lung cancer). (Not all compounds were assayed against all cell lines.)

The following compounds were used as reference or comparison cytotoxins: doxorubicin (Dox), Cytotoxin CBI (a DNA minor groove alkylating agent of the cyclopropa[c]benz[e]indol-4-one class), tubulysin D (Tub D, Table 1), and the methyl ester of MMAF ("MMAF," an auristatin-related compound; see Sutherland et al., *J. Biol. Chem.* 2006, 281 (15), 10540-10547).

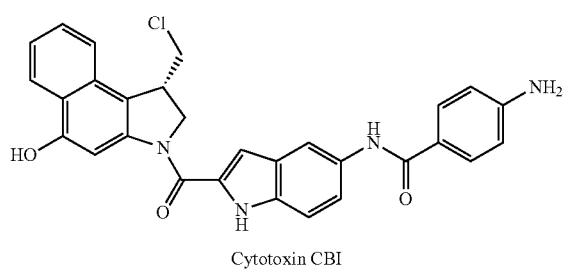 [SMILES: Nc1ccc(C(=O)Nc2ccc3[nH]c(C(=O)N4C[C@@H](CCl)c5c4cc(O)c4ccccc54)cc3c2)cc1]

Cytotoxin CBI

FIGS. 11*a* and 11*b* show illustrative plots for $^3$H thymidine proliferation assays for compounds of this invention, against HL-60 and 786-O cells, respectively, with Cytotoxin CBI and tubulysin D as comparative compounds, with an incubation period of 48 h.

FIGS. 12*a* and 12*b* show illustrative plots for ATP luminescence proliferation assays for a second set of compounds of this invention, against HL-60 and 786-O cells, respectively, with an incubation period of 72 h. FIGS. 12*c* and 12*d* show the plots for $^3$H thymidine proliferation assays for the same set of compounds, again against HL-60 and 786-O cells, respectively, with a 72 h incubation period. In each instance, doxorubicin was used as a comparative compound.

Table 2 provides the data for proliferation assays using the $^3$H thymidine method, with an incubation period of 72 h.

TABLE 2

$^3$H Thymidine Proliferation Assays (Part 1)

| Compound | HCT-15 | Hep3B | LNCaP | MDA-MB-231 | A2058 | U-87 MG | NCI-H460 |
|---|---|---|---|---|---|---|---|
| Dox | 149 | 44 | 130 | 133 | — | 106 | 101 |
| CBI | 0.040 | 0.020 | 0.051 | 0.019 | — | 0.14 | 0.042 |
| Tub D | 0.062 | 0.022 | 0.36 | 0.091 | — | 0.014 | 0.032 |
| MMAF | 1.3 | 0.11 | 1.7 | 0.29 | — | 0.12 | 0.37 |
| 15 | 67 | 1.6 | 27 | 1.3 | 1.6 | 0.42 | 2.0 |
| 16 | 284 | >100 | >100 | >100 | >100 | >100 | >100 |
| 17 | 392 | >100 | >100 | 84 | >100 | 12 | >100 |
| 19 | 1067 | 52 | >100 | — | 0.13 | >100 | >100 |
| 24 | 704 | 32 | 76 | 33 | 0.12 | 18 | >100 |
| 25 | 280 | 305 | 930 | 236 | 409 | 271 | 306 |
| 26 | 31 | 18 | >3000 | 15 | 25 | 5.2 | 18 |
| 26a | >100 | 36 | 80 | >100 | >100 | 71 | >100 |
| 28 | 223 | 24 | 64 | >100 | 0.96 | >100 | >100 |
| 29 | 0.18 | 0.041 | 0.54 | 0.13 | 0.40 | 0.064 | 0.21 |
| 29c | 2.4 | 3.0 | 5.2 | 4.8 | 5.6 | 0.51 | 15 |
| 36 | 64 | 39 | 342 | >100 | 60 | 15 | 52 |
| 51 | 101 | 4.2 | 41 | 8.7 | 0.40 | 0.75 | 7.2 |
| 54 | 0.44 | 0.30 | 16 | 1.6 | 0.64 | 0.11 | 0.31 |
| 56 | 2477 | >100 | >100 | >100 | >100 | >100 | >100 |

(Part 2)

| Compound | A549 | HPAC | PC3 | BT474 | SKOV3 | 786-O | UO-31 |
|---|---|---|---|---|---|---|---|
| Dox | 128 | 126 | 276 | 424 | 163 | 168 | 267 |
| CBI | 0.072 | 0.063 | 0.049 | 1.2 | 0.047 | 0.035 | 0.035 |
| Tub D | 0.014 | 0.015 | 0.038 | 0.51 | 0.039 | 0.15 | 0.10 |
| MMAF | 0.21 | 0.29 | 0.38 | 1.7 | 0.24 | 1.4 | 7.3 |
| (III-q) | — | — | — | — | — | 7.61 | — |
| 15 | 2.1 | 3.0 | 1.7 | 7.1 | 2.6 | — | 15 |
| 16 | >100 | >100 | >100 | >100 | 44 | 19 | >100 |
| 17 | >100 | >100 | 82 | >100 | 91 | 32 | >100 |
| 19 | >100 | >100 | >100 | >100 | >100 | >100 | >100 |
| 24 | 38 | >100 | 63 | >100 | 68 | >100 | >100 |
| 25 | 270 | 206 | 319 | 804 | 180 | 1862 | 435 |
| 26 | 18 | 11 | 16 | 11 | 4.6 | 26 | 50 |
| 26a | >100 | >100 | >100 | 7 | 47 | >100 | >100 |
| 28 | >100 | 34 | >100 | >100 | 9.9 | 61 | >100 |
| 29 | 0.44 | 0.069 | 0.21 | 0.57 | 0.029 | 1.2 | 0.13 |
| 29c | 6.5 | 32 | 11 | 12 | 1.9 | 3.9 | 1.0 |
| 36 | 44 | 83 | 66 | >100 | 32 | >100 | >100 |
| 51 | 7.8 | 6.4 | 5.6 | 30 | 4.4 | 10 | 35 |
| 54 | 0.24 | 0.83 | 0.82 | 8.8 | 0.34 | 6.9 | 1.3 |
| 56 | >100 | >100 | >100 | >100 | >100 | 29 | >100 |

(Part 3)

| Compound | H740 | DMS53 | SK-BR3 | ZR-75 | OVCAR3 | HL-60 | OVCAR8 |
|---|---|---|---|---|---|---|---|
| Dox | 255 | 979 | — | 794 | 258 | 56 | 2044 |
| CBI | 0.098 | 1.5 | — | 1.5 | 0.071 | 0.027 | 0.16 |
| Tub D | 2.2 | 0.21 | — | 1.7 | 0.051 | 0.032 | 0.17 |
| MMAF | 13 | 10 | — | 42 | 0.16 | 0.25 | 25 |
| (III-q) | — | — | — | — | — | 15.05 | — |
| 15 | 2.3 | 37 | 17 | — | >100 | 0.60 | 423 |
| 16 | >100 | >100 | >100 | >100 | >100 | 8.9 | 1869 |
| 17 | 32 | >100 | >100 | >100 | >100 | 17 | 2970 |
| 19 | 3.8 | >100 | >100 | 34 | 53 | 37 | 69 |
| 24 | 51 | >100 | >100 | 3.6 | 90 | 6.9 | >100 |
| 25 | 347 | 515 | 1714 | >3000 | 379 | 308 | 946 |
| 26 | 3.0 | 99 | 32 | >300 | 3.2 | 0.45 | 201 |
| 26a | 3.2 | >100 | 158 | 56 | 21 | 10 | 100 |
| 28 | 5.8 | >100 | >100 | 4.3 | 3.1 | 7.7 | 27 |
| 29 | 0.41 | 0.28 | 1.1 | 3.8 | 0.02 | 0.0099 | 0.70 |

TABLE 2-continued

³H Thymidine Proliferation Assays

| 29c | 5.3 | 76 | 72 | 44 | 3.6 | 1.8 | 1.4 |
| --- | --- | --- | --- | --- | --- | --- | --- |
| 36 | >100 | >100 | >100 | >100 | >100 | 107 | >100 |
| 51 | 37 | 24 | >100 | 1.3 | 2.5 | 4.2 | 20 |
| 54 | 10 | 2.0 | 1.1 | 2.2 | 3.9 | 0.53 | 2.1 |
| 56 | >100 | >100 | >100 | >100 | >100 | >100 | >3000 |

(Part 4)

| | Cell Line and $EC_{50}$ (nM) | | | |
| --- | --- | --- | --- | --- |
| Compound | CEM-C1 | Nomo-1 | RPMI-8226 | Raji |
| Box | 144 | 105 | 68 | 61 |
| CBI | 0.11 | 0.016 | 0.12 | 0.013 |
| Tub D | 0.018 | 0.042 | 0.037 | 0.013 |
| MMAF | 0.17 | 0.27 | 0.24 | 0.12 |
| 15 | 0.93 | 2.3 | 3.3 | 0.47 |
| 16 | 11 | 1.8 | 22 | 28 |
| 17 | 43 | 6.8 | 47 | 53 |
| 19 | 22 | 1.3 | 23 | 32 |
| 24 | 13 | 1.1 | 17 | 11 |
| 25 | 225 | 116 | 396 | 231 |
| 26 | 22 | 0.36 | 7.7 | 7.0 |
| 26a | 10 | 2.0 | 22 | 20 |
| 28 | 10 | 0.20 | 8.7 | 13 |
| 29 | 0.019 | 0.0075 | 0.034 | 0.024 |
| 29c | 45 | 0.43 | 16 | 8.5 |
| 36 | 44 | 124 | 48 | 15 |
| 51 | 2.0 | 3.5 | 2.2 | 1.5 |
| 54 | 0.38 | 0.77 | 0.36 | 0.20 |
| 56 | >100 | >100 | >100 | >100 |

Table 3 provides the data for the ATP luminescence proliferation assays, with an incubation period of 48, 72, or 96 h, as noted.

TABLE 3

ATP Luminescence Proliferation Assays (Incubation Period as Noted)

(Part 1)

| | Cell Line and $EC_{50}$ (nM) | | | | | | |
| --- | --- | --- | --- | --- | --- | --- | --- |
| Compound | HCT-15 (48 h) | Hep3B (48 h) | MDA-MB-231 (48 h) | A2058 (48 h) | NCI-H460 (48 h) | A549 (48 h) | PC3 (48 h) |
| Dox | — | 443 | — | — | — | 149 | 1082 |
| CBI | — | 2.6 | — | — | — | 3.0 | 12 |
| Tub D | — | 0.0012 | — | — | — | 0.020 | 0.039 |
| MMAF | — | 0.053 | — | — | — | 0.33 | 0.43 |
| 15 | 40 | 6.3 | 5.6 | 3.5 | 6.7 | — | >100 |
| 16 | 157 | 26 | 28 | 30 | 69 | — | >100 |
| 17 | 443 | >100 | 65 | 30 | 69 | — | >100 |
| 19 | — | 18 | — | — | — | — | ~33 |
| 24 | — | 10 | — | — | — | — | 13 |
| 25 | — | 246 | — | — | — | 111 | 155 |
| 26 | 113 | 100 | 120 | 93 | — | — | >3000 |
| 26a | — | — | — | — | — | — | — |
| 28 | — | 17 | — | — | — | — | 5.8 |
| 29 | — | 1.6 | — | — | — | 3.9 | 3.4 |
| 29c | 200 | 75 | 52 | 32 | — | — | 66 |
| 36 | — | 86 | — | — | — | 1.9 | 78 |
| 51 | — | 3.8 | — | — | — | — | 16 |

TABLE 3-continued

ATP Luminescence Proliferation Assays (Incubation Period as Noted)

| | | | | | | | |
|---|---|---|---|---|---|---|---|
| 54 | — | 1.5 | — | — | — | 3.0 | 3.1 |
| 56 | >3000 | >100 | >100 | >100 | >100 | — | >100 |

(Part 2)

Cell Line and $EC_{50}$ (nM)

| Compound | BT474 (48 h) | SKOV3 (48 h) | 786-O (48 h) | UO-31 (48 h) | DMS53 (48 h) | SK-BR3 (48 h) | ZR-75 (48 h) |
|---|---|---|---|---|---|---|---|
| Dox | — | 674 | 360 | 908 | — | — | — |
| CBI | — | 3.0 | 1.6 | 4.2 | — | — | — |
| Tub D | — | 0.029 | 0.022 | 0.099 | — | — | — |
| MMAF | — | 0.19 | 0.71 | 2.6 | — | — | — |
| 15 | 3.5 | 4.2 | — | — | 32 | 3.9 | 13 |
| 16 | 19 | 18 | — | — | 50 | 6.6 | 11 |
| 17 | 23 | 58 | — | >100 | ~80 | 24 | 24 |
| 19 | 8.8 | — | — | >100 | — | 3.9 | 20 |
| 24 | 4.6 | — | — | 13 | — | 8.9 | 8.4 |
| 25 | 166 | — | — | 759 | 366 | >3000 | 1003 |
| 26 | 19 | — | — | 240 | — | 253 | 208 |
| 26a | — | — | — | — | — | — | — |
| 28 | 12 | — | — | 5.8 | — | 7.8 | 16 |
| 29 | 1.5 | — | — | 2.7 | 5.3 | 3.6 | 15 |
| 29c | 492 | — | — | 26 | — | 278 | 136 |
| 36 | ~120 | — | — | 8.8 | ~300 | >300 | >300 |
| 51 | 11 | — | — | >100 | — | 13 | 19 |
| 54 | 4.8 | — | — | — | 7.9 | 6.2 | 9.6 |
| 56 | >100 | >100 | — | — | >100 | >100 | >100 |
| 84a | — | — | 6.12 | — | — | — | — |
| 84b | — | — | 4.10 | — | — | — | — |
| 109 | — | — | 1.03 | — | — | — | — |

(Part 3)

Cell Line and $EC_{50}$ (nM)

| Compound | OVCAR3 (48 h) | HL-60 (48 h) | CEM-C1 (48 h) | Nomo-1 (48 h) | RPMI-8226 (48 h) | HCT-15 (72 h) | LNCaP (72 h) |
|---|---|---|---|---|---|---|---|
| Dox | 632 | — | — | — | — | 600 | 592 |
| CBI | 4.1 | — | — | — | — | 3.4 | 3.3 |
| Tub D | 0.085 | — | — | — | — | 0.014 | 0.093 |
| MMAF | 0.17 | — | — | — | — | 0.075 | 0.98 |
| 15 | >100 | — | — | — | — | — | — |
| 16 | >100 | — | — | — | — | — | — |
| 17 | >100 | — | — | — | — | — | — |
| 19 | 25 | — | — | — | — | 245 | — |
| 24 | 29 | — | — | — | — | 188 | — |
| 25 | >3000 | 224 | — | 83 | — | 366 | — |
| 26 | — | — | 61 | 3.9 | 45 | — | 412 |
| 26a | — | — | — | — | — | — | — |
| 28 | 14 | — | — | — | — | 132 | — |
| 29 | >100 | 0.59 | — | 0.24 | — | 4.5 | — |
| 29c | — | — | 20 | 2.9 | 70 | — | 255 |
| 36 | >300 | 114 | — | 34 | — | 96 | >300 |
| 36a | — | 0.048 | — | — | — | — | — |
| 51 | 5.5 | — | — | — | — | 93 | — |
| 54 | >100 | 2.5 | — | 3.1 | — | 2.6 | 11 |
| 56 | >100 | — | — | — | — | — | — |
| 84a | 8.19 | 10-28 | — | — | — | 138 | — |
| 84b | 4.91 | 16-27 | — | — | — | 22.8 | — |
| 109 | — | 0.019 | — | — | — | — | — |
| 112 | — | 0.05-.09 | — | — | — | — | — |

(Part 4)

Cell Line and $EC_{50}$ (nM)

| Compound | MDA-MB-231 (72 h) | A2058 (72 h) | U-87 MG (72 h) | NCI-H460 (72 h) | A549 (72 h) | HPAC (72 h) | BT474 (72 h) |
|---|---|---|---|---|---|---|---|
| Dox | 518 | 101 | 324 | 92 | — | 215 | 388 |
| CBI | 3.1 | 0.20 | 3.3 | 0.64 | — | 6.0 | 5.5 |
| Tub D | 0.047 | 0.0064 | 0.0054 | 0.0076 | — | — | 0.021 |
| MMAF | 0.33 | 0.039 | 0.052 | 0.13 | — | 0.067 | 0.024 |

TABLE 3-continued

ATP Luminescence Proliferation Assays (Incubation Period as Noted))

| | | | | | | | |
|---|---|---|---|---|---|---|---|
| 15 | — | — | 8.6 | — | — | — | — |
| 16 | — | — | >100 | — | — | — | — |
| 17 | — | — | 22 | — | — | — | — |
| 19 | 32 | 26 | >100 | 43 | — | 0.33 | — |
| 24 | 13 | 14 | 18 | 23 | — | 1.1 | — |
| 25 | 202 | 212 | 357 | 177 | — | 97 | — |
| 26 | — | — | 94 | 90 | — | 279 | — |
| 26a | — | — | — | — | — | — | — |
| 28 | 16 | 20 | 18 | 35 | — | 5.9 | — |
| 29 | 5.1 | 2.9 | 4.9 | 3.0 | — | 4.9 | — |
| 29c | — | — | 136 | 6.0 | — | 4.6 | — |
| 36 | 9.6 | 43 | 37 | 16 | — | 2.9 | — |
| 51 | — | 5.5 | 7.6 | 14 | — | 4.5 | — |
| 54 | 5.6 | 1.4 | 1.6 | 1.6 | — | 0.96 | — |
| 56 | — | — | >100 | — | — | — | — |

(Part 5)

Cell Line (EC$_{50}$, nM)

| Compound | SKOV3 (72 h) | 786-O (72 h) | H740 (72 h) | DMS53 (72 h) | SK-BR3 (72 h) | ZR-75 (72 h) | OVCAR3 (72 h) |
|---|---|---|---|---|---|---|---|
| Dox | — | — | — | 755 | 441 | 236 | — |
| CBI | — | — | 2.2 | 3.8 | 3.1 | 2.2 | — |
| Tub D | — | — | 0.022 | 0.069 | 0.025 | 0.034 | — |
| MMAF | — | — | — | 4.5 | 0.16 | 0.25 | — |
| (III-q) | — | 103.6 | — | — | — | — | — |
| 15 | — | 9.4 | — | — | — | — | — |
| 16 | — | 36 | — | — | — | — | — |
| 17 | — | 73 | — | — | — | — | — |
| 19 | 15 | 40 | — | 87 | — | — | — |
| 24 | 13 | 36 | — | >100 | — | — | — |
| 25 | 109 | 306 | — | — | — | — | — |
| 26 | 38 | 126 | — | 193 | — | — | 49 |
| 26a | — | — | — | — | — | — | — |
| 28 | 11 | 29 | — | 58 | — | — | — |
| 29 | 1.3 | 2.8 | — | — | — | — | — |
| 29c | 17 | 34 | — | 17 | — | — | 99 |
| 36 | 45 | 183 | — | — | — | — | — |
| 36a | — | 0.434 | — | — | — | — | — |
| 51 | 10 | 19 | — | 46 | — | — | — |
| 54 | 1.3 | 2.6 | — | — | — | — | — |
| 56 | — | >100 | — | — | — | — | — |
| 109 | — | — | — | — | — | — | 0.202 |
| 112 | — | 0.67 | — | — | — | — | 0.049 |
| 133 | — | 4.17 | — | — | — | — | — |
| 134 | — | 9.89 | — | — | — | — | — |
| 135 | — | 12.94 | — | — | — | — | — |

(Part 6)

Cell Line and EC$_{50}$ (nM)

| Compound | HL-60 (72 h) | CEM-C1 (72 h) | Nomo-1 (72 h) | RPMI-8226 (72 h) | Raji (72 h) | SW480 (96 h) | SW-620 (96 h) |
|---|---|---|---|---|---|---|---|
| Dox | 147 | 161 | 338 | 345 | 301 | 215 | 145 |
| CBI | 0.76 | 0.55 | 0.37 | 4.1 | 2.1 | 0.92 | 0.33 |
| Tub D | 0.0096 | 0.0030 | 0.013 | 0.0051 | 0.0048 | 0.020 | 0.0058 |
| MMAF | 0.12 | 0.11 | 0.14 | 0.068 | 0.084 | 0.17 | 0.057 |
| (III-q) | 14.27 | — | — | — | — | — | — |
| 15 | 2.7 | 2.6 | 2.7 | 2.6 | 2.5 | 5.6 | 3.7 |
| 16 | 2.8 | 2.5 | 3.1 | 15 | 3.0 | 48 | 29 |
| 17 | 7.4 | 26 | 3.9 | 15 | 27 | 92 | 65 |
| 19 | 7.7 | 11 | 5.2 | 9.6 | 9.2 | 52 | 14 |
| 24 | 6.4 | 8.7 | 4.0 | 8.4 | 7.9 | 42 | 10 |
| 25 | — | 176 | — | 235 | 209 | 261 | 193 |
| 26 | 27 | — | — | — | 46 | 67 | 48 |
| 26a | — | — | — | — | — | — | — |
| 28 | 2.9 | 11 | 0.82 | 10 | 15 | 36 | 21 |
| 29 | — | 0.85 | — | 1.0 | 2.1 | 2.7 | 1.5 |
| 29c | 8.6 | — | — | — | 36 | 41 | 8.4 |
| 36 | — | 40 | — | 62 | 24 | 81 | 45 |
| 51 | — | 4.8 | 7.4 | 5.2 | 5.0 | 13 | 6.4 |
| 54 | — | 1.2 | — | 1.6 | 1.2 | 1.6 | 1.1 |
| 56 | >100 | >100 | >100 | 5.7 | 24 | >100 | 28 |

Additionally the following $EC_{50}$ values were measured for the following compounds against the H226 cell line, using the ATP assay and 72 h incubation period: compound 36a (0.307 nM); compound 109 (1.609 nM); and compound 112 (0.67-1.16 nM). The following $EC_{50}$ values were measured for the following compounds against the OVACAR8/Adr cell line, using the ATP assay and 48 h incubation period: compound 36a (17.05 nM); compound 84a (>300 nM); compound 84b (47.2 nM); compound 109 (24.9 nM); and compound 112 (12 nM).

Example 15

Conjugate In Vitro Activity

FIG. 13 shows the activity of conjugates of this invention in $^3$H thymidine proliferation assays, measured against 786-O renal cancer cells, which are CD70 positive. The incubation period was 72 h. The $EC_{50}$ values extracted from the curves of FIG. 13 are given in Table 4, along data from other experiments. Cell line LNCap is a prostate cancer cell line that expresses prostate specific membrane antigen (PSMA); H226 is a lung cancer cell line that expresses mesothelin. The antibodies used for conjugation were 2A10, an anti-PSMA antibody (Huang et al., US 2009/0297438); 2H5, an anti-CD70 antibody (Terrett et al., US 2009/0028872); 1F4, an anti-CD70 antibody (Coccia et al., WO 2008/074004); and 6A4, an anti-mesothelin antibody (Terrett et al., WO 2009/045957). As controls, Compound J of Sufi et al., WO 2008/083312 ("Cpd. J," a DNA minor groove binding/alkylating agent) was used as a conjugation partner and diphtheria toxin ("DTX") was used as an unconjugated non-specific control.

whose conjugates is undergoing clinical trials. It is noteworthy that the conjugates of Compounds (VI-a) and (VI-b) exhibit very little non-specific toxicity: compare the activities of 2A10-(VI-a) and 2A10-(VI-b) against that of 2A10-CBI.

Example 16

Conjugate In Vivo Activity

CD70-positive human renal cancer 786-O cells (Cat. CRL-1932 originally acquired from ATCC) were cultured in vitro per ATCC instructions. The cells were harvested, and 2.5 million cells per 200 µL of DPBS/MATRIGEL™ (1:1) were implanted subcutaneously in the flank region of CB17.SCID mice. Tumors were measured weekly in 3 dimensions with a Fowler Electronic Digital Caliper (Model 62379-531; Fred V. Fowler Co., Newton, Mass., USA) and data were electronically recorded using StudyDirector software from Studylog Inc. (South San Francisco, Calif., USA). Animals were checked daily for postural, grooming, and respiratory changes, as well as lethargy. Animals were also weighed weekly and euthanized if weight loss was ≥20%. When tumors reached an average size of 194 mm$^3$, groups of 6 mice each were treated with a single intraperitoneal (IP) dose of a test conjugate (e.g., 2H5-(VI-b)) and an isotype control (2A10-(VI-b)) at 0.3 µmol/kg body weight. Tumor volumes (LWH/2) and weights of mice were recorded throughout the course of each study, which were allowed to proceed for approximately 2 months post initial dosing. An Excel spreadsheet macro was used to calculate the mean, SD, and median values of tumor sizes. Data were graphed using Prism software version 4.0.

TABLE 4

In Vitro Activity of Conjugates

| Conjugate or Test Compound | | Cell | $EC_{50}$ |
|---|---|---|---|
| Designation | Description | Line | (nM) |
| 2A10-Cpd. J | Conjugate of 2A10 and Cpd. J | 786-O | 116.7 |
| DTX | Unconjugated non-specific control | 786-O | 104.4 |
| 2H5-Cpd. J | Conjugate of 2H5 and Cpd. J | 786-O | 0.08592 |
| 1F4-Cpd. J | Conjugate of 1F4 and Cpd. J | 786-O | 0.09951 |
| 2H5-(VI-a) | Conjugate of 2H5 and Compound (VI-a) | 786-O | 0.1151 to 0.0749 |
| 2A10-(VI-a) | Conjugate of 2A10 and Compound (VI-a) | 786-O | >>100 |
| 2H5-(VI-b) | Conjugate of 2H5 and Compound (VI-b) | 786-O | 0.06554 |
| 2A10-(VI-b) | Conjugate of 2A10 and Compound (VI-b) | 786-O | >>100 |
| 2H5-(VI-n) | Conjugate of 2H5 and Compound (VI-n) | 786-O | 0.4384 |
| 2H5-(VI-m) | Conjugate of 2H5 and Compound (VI-m) | 786-O | 0.5899 |
| 2H5-(VI-q) | Conjugate of 2H5 and Compound (VI-q) | 786-O | inactive |
| 2H5-(VI-p) | Conjugate of 2H5 and Compound (VI-p) | 786-O | inactive |
| 2H5-(VI-t) | Conjugate of 2H5 and Compound (VI-t) | 786-O | 0.310 |
| 6A4-(VI-t) | Conjugate of 6A4 and Compound (VI-t) | H226 | 0.360 |
| 2A10-(VI-t) | Conjugate of 2A10 and Compound (VI-t) | LNCap | 0.570 |

The data show that a CD70-specific antibody is needed for a conjugate to be able to effectively deliver a cytotoxin to CD70-positive 786-O cells: conjugates of antibody 2A10, which is specific for a different antigen (PSMA), have low or no activity. Conversely, all the conjugates of an anti-CD70 antibody were active. The conjugates of Compounds (VI-a) and (VI-b) were comparable in activity to the Compound J conjugates, a well known conjugation partner and one of The xenograft study results are shown in FIG. 14, where legend labels have the same meaning as in the previous Example and in FIG. 13. The data demonstrate the in vivo activity of conjugates of compounds of this invention against CD70$^+$786-O cells. Both conjugates of compounds (VI-a) and (VI-b) with the anti-CD70 antibody 2H5 caused a reduction in mean tumor size to less than half over the course of the study, while, when the vehicle control or a conjugate with the anti-PSMA antibody 2A10 was administered, tumor mean volume more than doubled.

Example 17

Scheme 13

Scheme 13 (FIG. 15) shows a method for making enantiomerically pure 4-nitrotubuphenylalanines (4-NO$_2$Tup) 82a and 82b, which are useful for making compounds of this invention.

Compound 80

Di-tert-butyl dicarbonate (90.5 mg, 0.42 mmol) was added to a mixture of compound 34 of Scheme 3 (0.1 g, 0.35 mmol) in 0.7 M aq. NaOH (1 mL). The reaction mixture was stirred at RT for 3 h, and then acidified to pH 3 with 0.5 N HCl. After the aqueous solution was extracted with EtOAc three times, the combined organic layers were dried, filtered, and concentrated. The crude product was purified by flash chromatography eluting from silica gel with a gradient of 0-20% methanol in DCM to afford 0.117 g of compound 80 as a white solid. MS: (+) m/z 253.1 (M+1 without Boc).

(−)-Menthol esters 81a and 81b

DCC (87.8 mg, 0.43 mmol) was added to a solution of compound 80, (−)-menthol (66.6 mg, 0.43 mmol), and 4-(dimethylamino)-pyridine ("DMAP," 10.4 mg, 0.085 mmol) in DCM (1.5 mL) at RT. After the reaction mixture was stirred at RT for 3 h, the precipitate was filtered off. The filtrate was then concentrated. The crude product was purified by flash chromatography eluting from silica gel with a gradient of 0-20% EtOAc in hexanes to afford 55.7 mg of ester 81a as a white solid, and 55.7 mg of ester 81b as a white solid. MS for ester 81a: (+) m/z 391.2 (M+1 without Boc); MS for ester 81b: (+) m/z 391.2 (M+1 without Boc).

4-NO$_2$Tup 82a and 82b

A solution of ester 81a in 6N HCl (40 mg, 0.082 mmol) was heated at 130° C. for 1.5 h. The reaction mixture was concentrated to afford 23.5 mg of 4-NO$_2$Tup 82a as a white solid. $^1$H NMR (D$_2$O, 400 MHz): δ 8.04 (d, 2H, J=8.4 Hz), 7.33 (d, 2H, J=8.4 Hz), 3.50 (m, 1H), 3.03 (dd, 1H, J=6.8, 14.4 Hz), 2.89 (dd, 1H, J=7.6 Hz, 14.4 Hz), 2.45-2.39 (m, 1H), 1.92-1.84 (m, 1H), 1.62-1.55 (m, 1H), and 0.98 (d, 3H, J=7.2 Hz); MS: (+) m/z 253.1 (M+1). 4-NO$_2$Tup 82b was obtained by the same procedure on the same scale as a white solid (23.5 mg). $^1$H NMR (D$_2$O, 400 MHz): δ 8.03 (d, 2H, J=8.4 Hz), 7.33 (d, 2H, J=8.4 Hz), 3.50 (m, 1H), 2.93 (dd, 2H, J=2.0, 7.6 Hz), 2.54-2.48 (m, 1H), 1.86-1.78 (m, 1H), 1.60-1.53 (m, 1H), and 0.98 (d, 3H, J=6.8 Hz); MS: (+) m/z 253.1 (M+1).

Example 18

Scheme 14

Scheme 14 (FIG. 16) depicts the conversion of 4-NO$_2$Tup 82a and 82b into compounds of this invention.

Nitro Acid 83a

Compound 34a of Scheme 3 (10 mg, 0.019 mmol) was added to a 0.2 M solution of pentafluorophenol (5.1 mg, 0.028 mmol) and N, N'-diisopropylcarbodiimide ("DIC," 0.0032 mL, 0.021 mmol) in DCM (0.2 mL) at 0° C. The reaction mixture was warmed to RT and stirred at such temperature overnight. The solvent was evaporated. EtOAc (1.8 mL) was added, and the crude product was filtered, with rinsing of the reaction vessel with EtOAc. The filtrate was concentrated under reduced pressure, and the crude pentafluorophenyl was used without further purification. DMF (0.2 mL) was added to the crude ester, followed by 4-NO$_2$Tup 82a (10.7 mg, 0.037 mmol), and DIEA (0.013 mL, 0.074 mmol). The reaction mixture was stirred at RT overnight, and the solvent was then evaporated off. The crude product was purified by flash chromatography eluting from silica gel with a gradient of 0-20% MeOH containing 1% NH$_4$OH in DCM to afford 12.9 mg of nitro acid 83a as a white solid. MS: (+) m/z 773.4 (M+1).

Alternative Route Nitro Acid 83a

DIEA was added to a solution of compound 34a (10 mg, 0.019 mmol), and HATU (7.8 mg, 0.020 mmol) in DMF (0.3 mL), maintaining the pH at 8-9. The reaction mixture was stirred at RT for 5 min. Then DIEA and nitro amine 82a (5.4 mg, 0.019 mmol) in DMF (1 mL) were added, maintaining the pH at 8-9. After the reaction mixture was stirred at RT for 15 min, the crude product was purified by preparative HPLC to afford 13.4 mg of nitro acid 83a as a white solid.

Nitro acid 83b was prepared by the same alternative route, on the same scale and was obtained as a white solide (13.4 mg). MS: (+) m/z 773.4 (M+1).

Amine 84a

A mixture of nitro acid 83a (7.5 mg, 0.0097 mmol) and palladium on carbon (10%, 1.1 mg) in MeOH (0.37 mL) was stirred under a hydrogen atmosphere for 4 h. The catalyst was filtered off, and the filtrate was concentrated. The crude product was purified by preparative HPLC to afford 6.2 mg of amine 84a as a white solid. $^1$H NMR (CD$_3$OD, 400 MHz): δ 8.06 (s, 1H), 7.36 (d, 2H, J=8.4 Hz), 7.17 (d, 2H, J=8.4 Hz), 5.70 (dd, 1H, J=2.8, 10.8 Hz), 4.71 (d, 1H, J=7.2 Hz), 4.44-4.35 (m, 2H), 3.74 (d, 1H, J=9.6 Hz), 3.49-3.45 (m, 1H), 3.36-3.35 (m, 1H), 3.30-3.25 (m, 1H), 3.13 (s, 3H), 3.14-3.04 (m, 1H), 2.93 (d, 2H, J=8.4 Hz), 2.74 (s, 3H), 2.48-2.28 (m, 3H), 2.15 (s, 3H), 2.19-2.03 (m, 2H), 1.95-1.86 (m, 4H), 1.80-1.71 (m, 2H), 1.71-1.57 (m, 3H), 1.24-1.13 (m, 1H), 1.16 (d, 3H, J=7.2 Hz), 1.04 (d, 3H, J=6.4 Hz), 1.02 (d, 3H, J=6.8 Hz), 0.94 (t, 3H, J=7.2 Hz), and 0.84 (d, 3H, J=6.8 Hz); MS: (+) m/z 743.4 (M+1).

Nitro acid 83b was hydrogenated to amine 84b using the same procedure, on an 8 mg scale. Amine 84b was obtained as a white solide (6.7 mg). $^1$H NMR (CD$_3$OD, 400 MHz): δ 8.06 (s, 1H), 7.35 (d, 2H, J=8.4 Hz), 7.16 (d, 2H, J=8.4 Hz), 5.70 (dd, 1H, J=2.8, 11.2 Hz), 4.72 (d, 1H, J=7.2 Hz), 4.49-4.32 (m, 2H), 3.75 (d, 1H, J=10.0 Hz), 3.49-3.45 (m, 1H), 3.36-3.35 (m, 1H), 3.33-3.31 (m, 1H), 3.12 (s, 3H), 3.12-3.04 (m, 1H), 2.91 (d, 2H, J=7.6 Hz), 2.74 (s, 3H), 2.57-2.52 (m, 1H), 2.45-2.37 (m, 1H), 2.33-2.28 (m, 1H), 2.15 (s, 3H), 2.19-2.13 (m, 1H), 2.03-1.88 (m, 5H), 1.81-1.57 (m, 5H), 1.24-1.13 (m, 1H), 1.17 (d, 3H, J=6.8 Hz), 1.04 (d, 3H, J=6.4 Hz), 1.02 (d, 3H, J=7.2 Hz), 0.94 (t, 3H, J=7.2 Hz), and 0.84 (d, 3H, J=6.4 Hz); MS: (+) m/z 743.4 (M+1).

Compounds 84a and 84b are also depicted in this specification by formulae (III-r) and (III-s), respectively.

Example 19

Scheme 15

Scheme 15 (FIG. 17) depicts the synthesis of conjugation-ready compounds of this invention having a single amino acid (citrulline) linker.

Compound 85

A mixture of compound 62 of Scheme 10 (0.22 g, 0.654 mmol), Fmoc-protected citrulline (0.39 g, 0.981 mmol), and N-(3-dimethylaminopropyl)-N'-ethylcarbodiimide hydrochloride ("EDCI," 0.188 g, 0.981 mmol) in DMF (4 mL) was stirred at RT overnight. The reaction was quenched by addition of saturated $NH_4Cl$, and the aqueous solution was extracted with EtOAc. The combined organic layers were dried, filtered, and concentrated. The crude product was purified by flash chromatography, eluting from silica gel with a gradient of 0-100% MeOH in DCM to afford 0.42 g of compound 85 as a white solid. MS: (+) m/z 716.4 (M+1).

Compound 86

Piperidine was added to a solution of compound 85 (0.248 g, 0.346 mmol) in DMF, maintaining the pH at 9-10. The reaction mixture was stirred at RT for 20 min, and then concentrated to afford 0.17 g of compound 86. MS: (+) m/z 494.4 (M+1).

Compound 87

LiOH (26.6 mg, 1.11 mmol) in water (3 mL) was added to a solution of compound 86 (0.17 g, 0.346 mmol) in THF (2 mL). After the reaction mixture was stirred at RT for 2 h, the solvent was partially removed. The aqueous solution was acidified to pH 2-3 with HCl and concentrated. The residue was re-dissolved in DMF (2 mL), and N-succinimidyl 6-maleimidohexanoate (0.16 g, 0.519 mmol) and DIEA (0.091 mL, 0.519 mmol) were added. After the reaction mixture was stirred at RT for 10 min, the crude product was purified by preparative HPLC to afford 0.198 g of compound 87 as a white solid. MS: (+) m/z 673.4 (M+1).

Compound 88

TFA (0.5 mL) was added to a solution of compound 87 (12.5 mg, 0.019 mmol) in DCM (0.5 mL) at room temperature. The reaction mixture was stirred at RT for 5 min, and then concentrated to afford 12.8 mg of compound 88 as a white solid. MS: (+) m/z 573.4 (M+1).

Compound 89

DIEA was added to a solution of compound 34a of Scheme 3 (5 mg, 0.0093 mmol) and HATU (3.9 mg, 0.010 mmol) in DMF (0.3 mL), maintaining the pH at 8-9. The reaction mixture was stirred at RT for 5 min. Then DIEA and compound 88 (12.8 mg, 0.019 mmol) in DMF (1 mL) were added, maintaining the pH at 8-9. After the reaction mixture was stirred at RT for 15 min, the crude product was purified by preparative HPLC to afford 8.6 mg of compound 89 as a white solid. MS: (+) m/z 1093.8 (M+1). Compound 89 is also depicted in this specification by formula (VI-m).

Compound 90

DIEA was added to a solution of compound 49 of Scheme 5 (5 mg, 0.0098 mmol) and HATU (4.1 mg, 0.011 mmol) in DMF (0.3 mL), maintaining the pH at 8-9. The reaction mixture was stirred at RT for 5 min. Then DIEA and compound 88 (13.5 mg, 0.0196 mmol) in DMF (1 mL) were added, maintaining the pH 8-9. After the reaction mixture was stirred at RT for 15 min, the crude product was purified by preparative HPLC to afford 8.9 mg of compound 90 as a white solid. MS: (+) m/z 1065.6 (M+1). Compound 90 is also depicted in this specification by formula (VI-p).

Example 20

Scheme 16

Scheme 16 (FIG. 18) depicts the preparation of conjugation-ready compounds of this invention, having a dipeptide (citrulline-valine) linker.

Compound 91

DIEA was added to a solution of Fmoc-protected valine (62.3 mg, 0.184 mmol) and HATU (63.6 mg, 0.167 mmol) in DMF (0.5 mL), maintaining the pH at 8-9. The reaction mixture was stirred at RT for 5 min. Then DIEA and compound 86 of Scheme 15 (82.5 mg, 0.167 mmol) in DMF (1 mL) were added, maintaining the pH at 8-9. After the reaction mixture was stirred at RT for 15 min, the reaction was quenched by addition of 0.05% aq. TFA. The aqueous solution was extracted with EtOAcef and the combined organic layers were dried, filtered and concentrated. The crude product was purified by flash chromatography eluting from silica gel with a gradient of 0-20% MeOH in DCM to afford 0.13 g of compound 91 as a white solid. MS: (+) m/z 815.5 (M+1).

Compound 92

Piperidine was added to a solution of compound 91 (0.144 g, 0.177 mmol) in DMF, maintaining the pH at 9-10. The reaction mixture was stirred at RT for 20 min and then concentrated. The residue was dissolved in THF (2.5 mL) and LiOH (16.3 mg, 0.681 mmol) in water (1.3 mL) was added. After the reaction mixture was stirred at RT for 2 h, the solvent was partially removed. The aqueous solution was acidified to pH 2-3 with HCl and then concentrated. The residue was re-dissolved in DMF (2.5 mL), and then N-succinimidyl 6-maleimidohexanoate (0.105 g, 0.341 mmol) and DIEA (0.060 mL, 0.341 mmol) were added. After the reaction mixture was stirred at RT for 10 min, the crude product was purified by preparative HPLC to afford 0.116 g of compound 92 as a white solid. MS: (+) m/z 772.5 (M+1).

Compound 93

TFA (0.6 mL) was added to a solution of compound 92 (14.4 mg, 0.019 mmol) in DCM (1 mL) at RT. The reaction mixture was stirred at RT for 5 min and then concentrated to afford 14.7 mg of compound 93 as a white solid. $^1$H NMR ($CD_3OD$, 400 MHz): δ 7.58 (dd, 2H, J=1.6, 8.4 Hz), 7.21 (dd, 2H, J=2.8, 8.8 Hz), 6.79 (s, 2H), 4.48 (m, 1H), 4.13 (d, 1H, J=7.6 Hz), 3.57-3.46 (m, 3H), 3.33-3.32 (m, 1H), 3.22-3.09 (m, 2H), 2.91-2.80 (m, 1H), 2.27 (t, 2H, J=7.2 Hz), 2.09-1.85

(m, 3H), 1.81-1.54 (m, 8H), 1.35-1.29 (m, 3H), 1.19 (d, 1.5 H, J=6.8 Hz), 1.18 (d, 1.5 H, J=7.2 Hz), 0.98 (d, 3H, J=2.4 Hz), 0.96 (d, 3H, J=2.8 Hz); MS: (+) m/z 672.4 (M+1).

Compound 94

DIEA was added to a solution of compound 34a of Scheme 3 (11 mg, 0.0204 mmol) and HATU (7.8 mg, 0.0204 mmol) in DMF (0.3 mL), maintaining the pH at 8-9. The reaction mixture was stirred at RT for 5 min. Then DIEA and compound 93 (14.7 mg, 0.019 mmol) in DMF (1 mL) were added, maintaining the pH at 8-9. After the reaction mixture was stirred at RT for 15 min, the crude product was purified by preparative HPLC to afford 18.9 mg of compound 94 as a white solid. MS: (+) m/z 1192.6 (M+1). Compound 94 is also depicted in this specification by formula (VI-n).

Acetate of Compound 27

Acetic anhydride (0.248 mL) was added to a solution of compound 27 of Scheme 2 (Peltier et al., 2006; 0.13 g, 0.218 mmol) in pyridine (2.6 mL) at 0° C. The reaction mixture was then stirred at RT overnight. After the reaction mixture was cooled at 0° C., a solution of water and 1,4-dioxane (12 mL, v/v 1:1) was added. The reaction mixture was stirred at RT overnight and then concentrated. The crude product was purified by flash chromatography eluting from silica gel with a gradient of 10-20% MeOH in DCM to afford 0.114 g of the acetate of compound 27 as a white solid. MS: (+) m/z 639.4 (M+1).

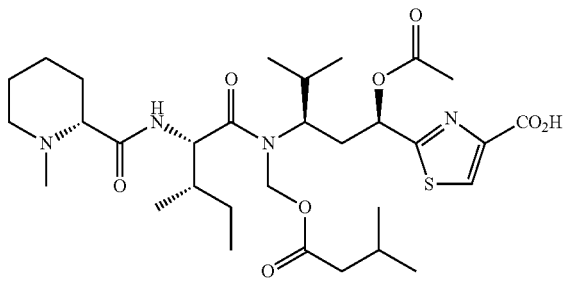

Acetate of Compound 27

Compound 95

DIEA was added to a solution of the acetate of compound 27 (3.8 mg, 0.0059 mmol), and HATU (2.5 mg, 0.0065 mmol) in DMF (0.3 mL), maintaining the pH at 8-9. The reaction mixture was stirred at RT for 5 min. Then DIEA and compound 93 (5.6 mg, 0.0071 mmol) in DMF (1 mL) were added, maintaining the pH at 8-9. After the reaction mixture was stirred at RT for 15 min, the crude product was purified by preparative HPLC to afford 6.5 mg of compound 95 as a white solid. MS: (+) m/z 1292.7 (M+1). Compound 95 is also depicted in this specification by formula (VI-o).

Example 21

Scheme 17

This example describes the synthesis of acid 108, an intermediate useful for the preparation of compounds of this invention, with reference to Scheme 17 (FIG. 19).

Methyl Ester 100

HCl in dioxane (8.3 ml, 4M, 33.2 mmol) was added to a solution of compound 9 of Scheme 1 (8 g, 22.1 mmol) in MeOH (10 mL). The reaction mixture was stirred at RT. After 20 min, the solution was evaporated under vacuum to give methyl ester 100 as an oil (6.5 g), which was used for the next reaction step without further purification.

Propyl Amine 101

Propanal (700 μL, 7.36 mmol) and NaBH(OAc)$_3$ (2.8 g, 13.2 mmol) were added to a solution of methyl ester 100 (1.96 g, 6.6 mmol) in DCM (10 mL). The reaction mixture was stirred at 5° C. After 1 h the mixture was taken up in EtOAc and washed with 7% K$_2$CO$_3$ solution twice and then brine. The EtOAc layer was dried over anhydrous Na$_2$SO$_4$ and then evaporated under vacuum to yield a residue which was passed through a column (MeOH:DCM. 0-10%) to give propyl amine 101 (1.12 g, 60%) as an oil. $^1$H NMR (400 MHz, CDCl$_3$) δ 8.17 (s, 1H), 5.43 (t, J=4.6 Hz, 1H), 3.93 (s, 3H), 3.07-2.87 (m, 2H), 2.82-2.70 (m, 1H), 2.54 (s, 1H), 2.45-2.26 (m, 2H), 2.16-2.02 (m, 1H), 1.73 (m, 2H), 1.05-0.94 (m, 9H). MS m/z C$_{14}$H$_{25}$N$_2$O$_3$S (M+1)$^+$ calculated 301.2. found 301.

Compound 102

(Benzotriazol-1-yloxy)tripyrrolidinophosphonim hexafluorophosphate ("PyBop," 1.28 g, 2.47 mmol), HOBt (0.33 g, 2.47 mmol), Boc-protected isoleucine (430 μL, 2.47 mmol) were added to a solution of propyl amine 101 (570 mg, 1.9 mmol) in DCM (5 mL). The reaction mixture was stirred at RT. After 20 min EtOAc (200 mL) was added and the organic layer was washed with 10% citric acid (twice), sat. NaHCO$_3$, and brine. The EtOAc layer was dried over anhydrous Na$_2$SO$_4$ and then evaporated under vacuum to yield a residue which was passed through a column to give compound 102 (0.55 g) as an oil. MS m/z C$_{25}$H$_{44}$N$_3$O$_6$S (M+1)$^+$ calculated 514.3. found 514.3.

Azido Ester 104

Acid chloride 103 (2 mmol, Lundquist et al. 2001; see also above in the preparation of azido ester 43 of Scheme 5) in DCM (3 mL) was added to a solution of compound 102 (0.55 g, 1.1 mmol) in DCM (10 mL) and DIEA (871 μL, 5 mmol). The reaction mixture was stirred at 5° C. After stirring for 10 min the mixture was evaporated under vacuum to give a residue which was passed through a column to give azido ester 104 (300 mg) as an oil. MS m/z C$_{31}$H$_{53}$N$_6$O$_2$S (M+1)$^+$ calculated 653.4. found 653.

Compound 106

A solution of pentafluorophenyl ester 105 (2.1 mmol, Peltier et al. 2006) in 1 mL of EtOAc was added to a solution of azido ester 104 (300 mg, 0.46 mmol) and Pd/C (10%, 50 mg) in EtOAc (5 mL). The reaction flask was filled with H$_2$ using a balloon and was stirred overnight at RT. After stirring overnight the reaction mixture was filtered, concentrated under vacuum and then passed through a column (MeOH: DCM, 0-10%) to give compound 106 (170 mg) as an oil. MS m/z C$_{38}$H$_{66}$N$_5$O$_8$S (M+1)$^+$ calculated 752.5. found 752.5.

Compound 107

NaOH (120 uL, 1.2 mmol, 10M) was added to a solution of compound 106 (170 mg, 0.22 mmol) in MeOH (10 mL) at RT.

After stirring for 2 hr the reaction mixture was acidified to pH 2 with concentrated HCl. The reaction mixture was then evaporated under vacuum and passed through a reverse phase column (ACN:$H_2O$, 0-100% with 0.1% TFA). After lyophilization, compound 107 (63 mg) was obtained as a white powder. HPLC profile indicated it was a mixture of rotamers. MS m/z $C_{26}H_{45}N_4O_5S$ (M+1)$^+$ calculated 525.3. found 525.

Acid 108

Acetic anhydride (60 uL, 0.64 mmol) was added to a solution of compound 107 (63 mg, 0.12 mmol) in pyridine (1 mL) at 5° C. The temperature was raised to RT gradually. After allowing reaction to proceed overnight, water (100 uL) was added. After another 5 hr, the volatile organics were removed under vacuum to give a residue which was passed through a reverse phase column (ACN:$H_2O$, 0-100% with 0.1% TFA) to give acid 108 (42 mg) as an oil. $^1$H NMR (400 MHz, $CD_3OD$) δ 8.35 (s, 1H), 5.71 (dd, J=11.4, 1.4 Hz, 1H), 4.63 (d, J=9.1 Hz, 1H), 3.97 (t, J=16.4 Hz, 1H), 3.65-3.42 (m, 2H), 3.21-3.05 (m, 2H), 2.87 (s, 3H), 2.34-2.14 (m, 4H), 2.13 (s, 3H), 2.03-1.46 (m, 10H), 1.29-1.06 (m, 1H), 1.04-0.85 (m, 15H). MS m/z $C_{28}H_{42}N_4O_5S$ (M+1)$^+$ calculated 567.3. found 567.

Example 22

Schemes 18 and 19

Scheme 18 (FIGS. 20a and 20b) shows the synthesis of compounds of this invention using as acid 108, prepared in the preceding example.

General Procedure for HATU-Mediated Coupling

HATU (1.2× excess) and DIEA (4× excess) were added into a solution of acid 108 in DMF at 5° C. After stirring the reaction mixture for 10 min, the corresponding amine was added. The reaction mixture was stirred for another 10 min before diluting it with DMSO and 0.1% TFA solution. The resulting mixture was passed through a reverse phase column (ACN:$H_2O$, 0-100% with 0.1% TFA). The collected fractions were analyzed and the desired fractions were lyophilized to give the corresponding product.

Compound 109

Obtained from the coupling of acid 108 and phenylalanine methyl ester. MS m/z $C_{38}H_{58}N_5O_7$ (M+1)$^+$ calculated 728.4. found 728.4. Compound 109 is also depicted hereinabove as structure (III-x).

Compound 111

Obtained from the coupling of acid 108 and compound 110 (preparation described below). MS m/z $C_{42}H_{63}N_6O_9S$ (M+1)$^+$ calculated 827.4. found 827.5.

Compound 112

To a solution of compound 111 (5 mg, 6 μmol) in 2 mL of MeOH was added Pd/C (10%, 10 mg). The reaction flask was filled with $H_2$ using a balloon and was stirred for 2 h at RT. The reaction mixture was then filtered, concentrated under vacuum and passed through a reverse phase column (ACN:$H_2O$, 0-100% with 0.1% TFA) to give compound 112 (2.1 mg) as a white power. MS m/z $C_{42}H_{62}N_6O_2S$ (M+1)$^+$ calculated 799.5. found 799.5. Compound 112 is also depicted hereinabove as structure (III-y).

Compound 114

Obtained from the coupling of acid 108 and compound 113 (preparation described below). MS m/z $C_{41}H_{64}N_5O_7S$ (M+1)$^+$ calculated 770.4. found 770.

Compound 116

Obtained from the coupling of acid 108 and compound 115 (preparation described below). MS m/z $C_{61}H_{95}N_{11}O_{13}S$ (M+2)$^+$ calculated 610.9. found 611. Compound 116 is also depicted hereinabove as structure (VI-t).

Compound 117

Obtained from the coupling of acid 108 and alpha-N-acetyl lysine methyl ester. MS m/z $C_{37}H_{63}N_6O_8S$ (M+1)$^+$ calculated 751.4. found 751.5.

Compound 110

Alkene 59 of Scheme 8 (as ethyl ester instead of methyl ester, 1 g, 2.6 mmol) was dissolved in DCM (10 mL) containing 5% TFA and the reaction mixture was stirred at 5° C. After 40 min the mixture was dried under vacuum to give compound 110 (0.3 g, 100%) as a semi-solid. $^1$H NMR (400 MHz, $CD_3OD$) δ 8.22-8.17 (m, 2H), 7.50 (dd, J=9.0, 2.2 Hz, 2H), 6.58 (d, J=10.0 Hz, 1H), 4.45 (td, J=9.8, 5.3 Hz, 1H), 4.19 (q, J=7.1 Hz, 2H), 3.35-3.28 (m, 1H), 3.06 (dd, J=13.2, 9.6 Hz, 1H), 1.55 (d, J=0.9 Hz, 3H), 1.27 (t, J=7.1 Hz, 3H).

Compound 113

HCl (2.5 mL, 10 mmol, 4 M) was added to a solution of compound 118 (2 g, 5.5 mmol, Peltier et al. 2006) in MeOH (10 mL) and the reaction mixture was stirred at RT. After 20 min the reaction mixture was dried under vacuum to give compound 113 (2 g, 100%) as a semi-solid. Crude product was used for the next step reaction without further purification. MS m/z $C_{13}H_{19}NO_2$ (M+1)$^+$ calculated 222.1. found 222.

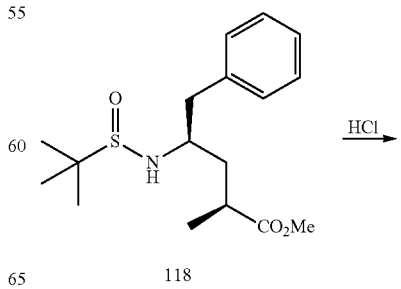

118

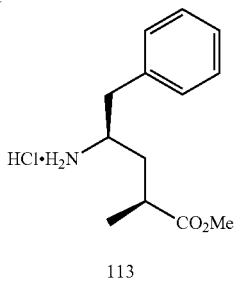

113

Scheme 19 (FIG. 21) shows the synthesis of compound 115, used in the synthesis of compound 116, above.

Compound 120

DIEA (697 µL, 12 mmol) and valine t-butyl ester 543 (627 mg, 3 mmol) were added into a 10 mL DCM solution of 6-maleimidohexanoic acid ("6-MHA," 622 mg, 3 mmol) and HATU (1.14 g, 3 mmol). After 20 min EtOAc (200 mL) was added. The organic phase was washed with 10% citric acid, sat. NaHCO$_3$ solution, and brine. It was then dried with anhydrous Na$_2$SO$_4$ and the solvent was removed by evaporation. The resulting residue was passed through a column (Hexane:EtOAc, 0-80%) to give compound 120 (900 mg) as an oil. $^1$H NMR (400 MHz, CDCl$_3$) δ 6.66 (s, 2H), 5.94 (d, J=8.5 Hz, 1H), 4.44 (dd, J=8.7, 4.5 Hz, 1H), 3.49 (t, J=7.2 Hz, 2H), 2.31-2.06 (m, 3H), 1.73-1.54 (m, 4H), 1.45 (s, 9H), 1.37-1.25 (m, 2H). MS m/z C$_{19}$H$_{31}$N$_2$O$_5$ (M+1)$^+$ calculated 367.2. found 367.

Compound 121

Compound 120 (1 g, 2.73 mmol) was dissolved in 20 mL DCM with 3 mL TFA at RT. After 1 h the mixture was dried by evaporation to give compound 121 (1 g) as an oil, which was used without further purification. MS m/z C$_{15}$H$_{23}$N$_2$O$_5$ (M+1)$^+$ calculated 311.2. found 311.

Compound 123

DIEA (920 µL, 5.28 mmol) and compound 122 (500 mg, 1.32 mmol; see Scheme 22 and Example 25 hereinbelow) were added a 10 mL DMF solution of Fmoc-protected citrulline (524 mg, 1.32 mmol) and HATU (601 mg, 1.58 mmol). After 20 min, 200 mL EtOAc was added. The organic phase was washed with 10% citric acid, sat. NaHCO$_3$ solution, and brine. It was then dried with anhydrous Na$_2$SO$_4$ and the EtOAc was evaporated. The resulting residue was passed through a column (MeOH:DCM; 0-10%) to give a solid. This solid was dissolved in DMF (5 mL) with 5% piperidine. After 1 h the solution was evaporated and the residue was passed through a reverse phase column (ACN:H$_2$O; 0-100% with 0.1% TFA) to give compound 123 (212 mg). MS m/z C$_{22}$H$_{46}$N$_5$O$_6$ (M+1)$^+$ calculated 536.3. found 536.4.

Compound 124

DIEA (404 µL, 2.4 mmol) and compound 560 (321 mg, 0.6 mmol) were added into a 5 mL DMF solution of compound 550 (180 mg, 0.58 mmol) and HATU (220 mg, 0.58 mmol). After 20 min 200 mL EtOAc was added. The organic phase was washed with 10% citric acid, sat. NaHCO$_3$ solution, and brine. It was then dried with anhydrous Na$_2$SO$_4$ and the EtOAc evaporated. The resulting residue was passed through a column (MeOH:DCM; 0-20%) to give compound 124 (240 mg) as an oil. MS m/z C$_{42}$H$_{66}$N$_7$O$_{10}$ (M+1)$^+$ calculated 828.5. found 828.5.

Compound 115

Compound 124 (240 mg, 0.29 mmol) was dissolved in a 5 mL solution of TFA and DCM (1:1). After 3 h the mixture was dried by evaporation and the resulting compound 115 was used without further purification. From NMR, a mixture of two (5:1) isomers was obtained. The major isomer is reported: $^1$H NMR (400 MHz, CD$_3$OD) δ 8.27 (d, J=7.5 Hz, 1H), 7.58 (dd, J=8.5, 1.9 Hz, 2H), 7.21 (d, J=8.5 Hz, 2H), 6.79 (s, 2H), 4.48 (dd, J=13.3, 8.1 Hz, 1H), 4.14 (dd, J=7.5, 4.9 Hz, 1H), 3.62-3.38 (m, 3H), 3.25-2.97 (m, 3H), 2.96-2.78 (m, 2H), 2.70-2.40 (m, 1H), 2.32-2.21 (m, 2H), 2.11-1.92 (m, 2H), 1.94-1.83 (m, 1H), 1.82-1.70 (m, 1H), 1.70-1.49 (m, 7H), 1.19 (d, J=7.0 Hz, 3H), 0.97 (dd, J=6.8, 2.8 Hz, 6H). MS m/z C$_{33}$H$_{50}$N$_7$O$_8$ (M+1)$^+$ calculated 672.4. found 672.

Example 23

Scheme 20

Scheme 20 (FIG. 22) shows the synthesis of compound 131, an intermediate used for making compounds of this invention.

Compound 125

Compound 9 of Scheme 1 (3 g, 8.29 mmol) was dissolved in THF (20 mL) and dimethylsufate (1.2 mL, 12.4 mmol). To this solution was added NaH (552 mg, 13.8 mmol) at 5° C. in portions over 1.5 h. The reaction mixture was then poured into sat. NH$_4$Cl solution. EtOAc was added to the reaction mixture and the organic phase was washed with brine and dried and evaporated under vacuum to give a residue. The resulting residue was passed through a column (Hexane:EtOAc, 0-100%) to give compound 125 (1.2 g) as an oil. $^1$H NMR (400 MHz, CDCl$_3$) δ 8.12 (s, 1H), 4.95 (dd, J=10.0, 3.3 Hz, 1H), 3.89 (s, 3H), 3.50 (s, 3H), 3.45-3.40 (m, 2H), 1.93-1.79 (m, 2H), 1.74-1.65 (m, 1H), 1.20 (s, 9H), 0.84 (d, J=6.8 Hz, 3H), 0.80 (d, J=6.8 Hz, 3H). MS m/z C$_{16}$H$_{29}$N$_2$O$_4$S$_2$ (M+1)$^+$ calculated 377.1. found 377.2.

Compound 126

HCl in dioxane (1 ml, 4 mmol) was added to a solution of compound 125 (0.7 g, 1.86 mmol) in MeOH (10 mL). The reaction mixture was stirred at RT. After 20 min, the volatiles were evaporated under vacuum to give compound 126 (0.8 g) as an oil which was used for the next reaction step without further purification. MS m/z C$_{12}$H$_{21}$N$_2$O$_3$S (M+1)$^+$ calculated 273.1. found 273.

Compound 127

To a solution of compound 126 (616 mg, 2 mmol) in DCM (10 mL) and DIEA (1.8 mL, 10 mmol) at 5° C., was added compound 103 (Scheme 17, 6 mmol) in 5 mL of DCM. The reaction mixture was stirred for 3 h at RT. After 3 h the reaction mixture was poured into sat. NaHCO$_3$ solution and EtOAc. The organic phase was washed with brine, dried, and evaporated. The resulting residue was passed through a column (Hexane:EtOAc, 0-50%) to give compound 127 (594 mg, 72%) as a semi oil. $^1$H NMR (400 MHz, CDCl$_3$) δ 8.18 (s, 1H), 6.47 (d, J=9.9 Hz, 1H), 4.60-4.52 (m, 1H), 4.23-4.13 (m, 1H), 3.96-3.95 (m, 1H), 3.94 (s, 3H), 3.44 (s, 3H), 2.21-2.08 (m, 1H), 1.94-1.84 (m, 2H), 1.84-1.71 (m, 1H), 1.52-1.38 (m, 1H), 1.35-1.20 (m, 1H), 1.07 (d, J=6.9 Hz, 3H), 0.95-0.85 (m, 9H). $^{13}$C NMR (101 MHz, CDCl$_3$) δ 176.00, 168.63, 161.92, 146.90, 128.24, 78.81, 70.34, 58.97, 52.72, 50.76, 40.48, 38.62, 32.24, 24.32, 19.13, 18.13, 16.25, 11.82. MS m/z $C_{18}H_{30}N_5O_4S$ (M+1)$^+$ calculated 412.2. found 412.3.

Compound 129

Potassium hexamethyldisilazide ("KHMDS," 0.19 mmol, 0.375 mL of toluene solution) was added into a THF (0.5 mL) solution of compound 127 (50 mg, 0.12 mmol) at −43° C. After 20 min compound 128 (0.36 mmol, 137 uL, Abe et al. 1997) was added. After 2 hr, 100 μL MeOH was added and the reaction mixture was poured into sat. NH$_4$Cl solution. EtOAc was then added. After separation of the layers, the organic phase was washed with brine, dried with anhydrous Na$_2$SO$_4$ and the solvent removed by evaporation. The resulting residue was passed through a column (Hexane:EtOAc, 0-50%) to give compound 129 (51 mg) as a semi solid. $^1$H NMR (400 MHz, CDCl$_3$) δ 8.16 (s, 1H), 5.70 (s, 1H), 5.43 (d, J=12.4 Hz, 1H), 5.32 (d, J=12.3 Hz, 1H), 4.39 (d, J=10.6 Hz, 1H), 3.92 (d, J=11.7 Hz, 3H), 3.53-3.44 (m, 1H), 3.37 (d, J=10.5 Hz, 3H), 2.41 (d, J=7.2 Hz, 2H), 2.37-2.11 (m, 4H), 1.92-1.68 (m, 2H), 1.37-1.21 (m, 1H), 1.12-0.85 (m, 18H). $^{13}$C NMR (101 MHz, CDCl$_3$) δ 175.24, 172.79, 171.21, 161.90, 147.09, 128.25, 78.44, 68.69, 63.35, 58.71, 52.48, 43.23, 38.63, 34.91, 31.01, 25.73, 25.25, 22.58, 22.56, 22.48, 20.45, 19.62, 16.14, 10.65. MS m/z $C_{24}H_{40}N_5O_6S$ (M+1)$^+$ calculated 526.3. found 424.3 (breaking of the N,O acetal).

Compound 130

Compounds 129 (200 mg, 0.38 mmol) and 105 (Peltier et al. 2006; 4 mmol) were mixed in 5 mL EtOAc with Pd/C (150 mg, 10%) at rt. The reaction flask was evacuated and refilled with H$_2$ using a balloon. After stirring overnight at RT, the mixture was filtered and the solvent evaporated. After column chromatography (SiO$_2$, MeOH:DCM, 0-10%), compound 130 (97 mg) was obtained as a solid. MS m/z $C_{31}H_{53}N_4O_7S$ (M+1)$^+$ calculated 625.4. found 625.5.

Compound 131

Tribuytltin hydroxide (181 mg, 0.59 mmol) was added to a solution of compound 130 (97 mg, 0.16 mmol) in 10 mL 1,2-dichloroethane. After 22 h at 67° C., the mixture was evaporated and passed through a reverse phase column (ACN:(20 mM NH$_4$(HCO$_3$) buffer, pH 7), 5-100%) to give compound 131 (34 mg) as a solid. MS m/z $C_{30}H_{51}N_4O_7S$ (M+1)$^+$ calculated 611.3. found 510 (break at the N,O acetal).

Example 24

Scheme 21

Scheme 21 (FIG. 23) shows the synthesis of compounds of this invention using compound 131 as a precursor.

Compound 132

Compound 60 (Scheme 8, 200 mg, 0.57 mmol) was dissolved in 2 mL DCM with 20% TFA at rt. After 1 h the volatiles were evaporated to give compound 132 (200 mg) as a yellow solid, which was used without further purification.

Compound 133

DIEA (43 μL, 0.2 mmol) was added to a DMF (1 mL) solution of compound 131 (30 mg, 0.049 mmol) and HATU (22.3 mg, 0.059 mmol) at −43° C. After 10 min compound 132 (15 mg, 0.06 mmol) was added. The mixture was then raised to RT. The final mixture was passed through a reverse phase column (ACN:(20 mM NH$_4$(HCO$_3$) buffer, pH 7), 5-100%) to give compound 133 (20 mg) as a white powder. MS m/z $C_{44}H_{73}N_6O_8S$ (M+1)$^+$ calculated 843.5. found 843.5. Compound 133 is also depicted hereinabove as structure (III-u).

Compound 134

Compound 133 (2 mg, 2.4 μmol) was dissolved in 0.5 mL methanol and the pH of the solution was adjusted to 1 with 1M HCl. After stirring overnight, the volatiles were evaporated and the residue was passed through a reverse phase column (ACN:(20 mM NH$_4$(HCO$_3$) buffer, pH 7), 5-100%) to give compound 134 (0.7 mg) as a white powder. MS m/z $C_{40}H_{65}N_6O_7S$ (M+1)$^+$ calculated 773.5. found 773.5. Compound 134 is also depicted hereinabove as structure (III-v).

Compound 135

Compound 133 (2 mg, 2.4 μmol) was dissolved in 0.5 mL n-propanol and the pH of the solution was adjusted to 1 with1M HCl. After stirring overnight, the mixture was evaporated and the residue was passed through a reverse phase column (ACN:(20 mM NH$_4$(HCO$_3$) buffer, pH 7), 5-100%) to give compound 135 (0.4 mg) as a white powder. MS m/z $C_{42}H_{69}N_6O_7S$ (M+1)$^+$ calculated 802.5. found 801.5. Compound 135 is also depicted hereinabove as structure (III-w).

Example 25

Scheme 22

Scheme 22 (FIG. 24) shows a method for making compound 142, useful as an intermediate for making compounds of this invention.

Compound 136

NaOH (800 uL, 10M, 8 mmol) was added to a 20 mL solution of THF and MeOH (1:1) with compound 59 of Scheme 8 (1.65 g, 4.37 mmol). After stirring overnight the pH of the solution was adjusted to 1 with 3N HCl at 5° C. After evaporation of the solvents, 200 mL EtOAc was added. After separation, the organic phase was washed with brine, dried with anhydrous Na$_2$SO$_4$ and the EtOAc evaporated. The residue was passed through a column (MeOH:DCM; 0-10%) to give compound 136 (1.2 g) as an oil. $^1$H NMR (400 MHz, CDCl$_3$) δ 8.21-8.12 (m, 2H), 7.41-7.32 (m, 2H), 6.62 (d, J=8.8 Hz, 1H), 4.82-4.57 (m, 2H), 3.15-3.02 (m, 1H), 2.90 (dd, J=13.3, 7.2 Hz, 1H), 1.71 (d, J=1.2 Hz, 3H), 1.41 (s, 9H).

Compound 137

DMF-di-t-Butylacetal (1 mL, 4 mmol) was added to a 6 mL toluene solution of compound 136 (128 mg, 0.36 mmol) at 133° C. After 10 min the reaction mixture was cooled and the solvent evaporated. The residue was passed through a column (Hexane:EtOAc; 0-30%) to give compound 137 (133 mg) as an oil. $^1$H NMR (400 MHz, CDCl$_3$) δ 8.19-8.10 (m, 2H), 7.39-7.30 (m, 2H), 6.39 (dd, J=9.1, 1.5 Hz, 1H), 4.63 (d, J=39.1 Hz, 2H), 3.03 (dd, J=13.2, 6.2 Hz, 1H), 2.90 (dd, J=13.3, 7.0 Hz, 1H), 1.67 (d, J=1.5 Hz, 3H), 1.47 (s, 9H), 1.39 (s, 9H).

Compound 122

Compound 137 (540 mg, 1.22 mmol), Pd/C (136 mg, 10%) and 3N HCl (0.3 mL) were added to a mixture of DCM and MeOH (30 mL:5 mL). The flask was filled with $H_2$ using a balloon. After stirring overnight at RT, the mixture was filtered and concentrated to give compound 122 (550 mg) as a semi-solid. MS m/z $C_{21}H_{35}N_2O_4$ (M+1)$^+$ calculated 379.3. found 223 (loss of Boc).

Compound 138

Compound 136 (100 mg, 0.28 mmol) and Pd/C (20 mg, 10%) were mixed in a 5 mL mixture of MeOH and DCM (1:1 v:v) under a hydrogen balloon at RT. After stirring overnight the mixture was filtered and the solvents evaporated under vacuum to give compound 138 (95 mg) as oil, which was used for next reaction step without further purification. MS m/z $C_{17}H_{27}N_2O_4$ (M+1)$^+$ calculated 323.2. found 223.

Compound 139

Compound 138 (10 mg, 0.03 mmol), tert-butyldimethylsilyl chloride ("TBDMSCl," 4.5 mg, 0.03 mmol) and imidazole (4 mg, 0.06 mmol) were mixed in 1 mL DMF at RT. Fmoc-protected citrulline (24 mg, 0.06 mmol), N,N'-disuccinimidyl oxalate ("DSO," 8 mg, 0.06 mmol) and DIEA (20 uL, 0.12 mmol) were mixed in another 1 mL of DMF at RT. After 1 h the two solutions were mixed and the mixture was kept at RT. After stirring overnight, EtOAc was added and the solution was washed with 10% aq. citric acid and brine. The organic phase was then dried with anhydrous $Na_2SO_4$ and evaporated under vacuum. The resulting residue was passed through a column (MeOH:DCM, 0-10%) to give compound 139 (7 mg) as an oil. MS m/z $C_{38}H_{48}N_5O_8$ (M+1)$^+$ calculated 702. found 702.

Compound 141

Compound 139 (10 mg, 0.014 mmol) was dissolved in 1 mL DMF with 5% piperidine. After 20 min the solvent was evaporated under vacuum and the residue was mixed with N-succinimidyl-4-maleimidobutyrate 140 (5.6 mg, 0.028 mmol) and DIEA (5 uL, 0.028 mmol) in 1 mL DMF. After 10 min the solvents were removed from the reaction mixture under vacuum and passed through a column (MeOH:DCM, 0-20%) to give compound 141 (6 mg) as a solid. MS m/z $C_{31}H_{45}N_6O_9$ (M+1)$^+$ calculated 645. found 645.

Compound 142

Compound 141 (6 mg, 0.01 mmol) was dissolved in 1 mL DCM with 10% TFA. After 10 min the solvent was evaporated under vacuum to give compound 142 (6 mg), used for next reaction step without further purification.

Example 26

Scheme 23

Scheme 23 (FIG. 25) shows the elaboration of compound 142, made per Scheme 22, into a compound of this invention.

Compound 145

HCl (30 μmmol) in 150 μL MeOH was added to a solution of compound 27 of Scheme 2 (5 mg, 8.3 μmmol) in 0.7 mL MeOH at 5° C. The temperature was allowed to rise to RT gradually. After stirring overnight the mixture was evaporated and dissolved in 0.7 pyridine. To this solution was added $Ac_2O$ (28 μL, 296 μmmol) at 5° C. The temperature was allowed to rise to RT gradually and after stirring overnight 50 μL $H_2O$ was added. After 3 h the volatiles was evaporated and the resulting residue was evaporated to give compound 145 (4.7 mg) as a semi solid. MS m/z $C_{22}H_{45}N_4O_7S$ (M+1)$^+$ calculated 569.3. found 569.

Compound 146

DIEA (6 μL, 34 μmol) and compound 142 (5.5 mg, 8.3 μmol) were added to 0.5 mL DMF solution of compound 530 (4.7 mg, 8.3 μmmol) and HATU (3.2 mg, 8.4 μmol) at 5° C. After 20 min, the resulting mixture was passed through a reverse phase column (ACN:(20 mM $NH_4(HCO_3)$ buffer, pH 7), 5-100%) to give compound 146 (4.5 mg) as a white solid. MS m/z $C_{53}H_{79}N_{10}O_{13}S$ (M+1)$^+$ calculated 1095.5. found 1095.5. Compound 146 is also depicted hereinabove as structure (VI-r).

Compound 147

DIEA (1.4 uL, 8 μmol) and a drop of saturated $NH_4Cl$ solution were added into a 0.5 mL DMF solution of compound 146 (2 mg, 1.8 μmol) and HATU (1.6 mg, 4.6 μmol). After 10 min the mixture was passed through a reverse phase column (ACN:(20 mM $NH_4(HCO_3)$ buffer, pH 7), 5-100%) to give compound 147 (0.5 mg) as a semi solid. MS m/z $C_{53}H_{80}N_{11}O_{12}S$ (M+1)$^+$ calculated 1094.6. found 1094. Compound 147 is also depicted hereinabove as structure (VI-s).

Example 27

4-Aminotubuphenylalanine Diastereomers

Compound 122 (Example 25 above) was determined to be a 3:1 mixture of diastereomers 148a and 148b as follows.

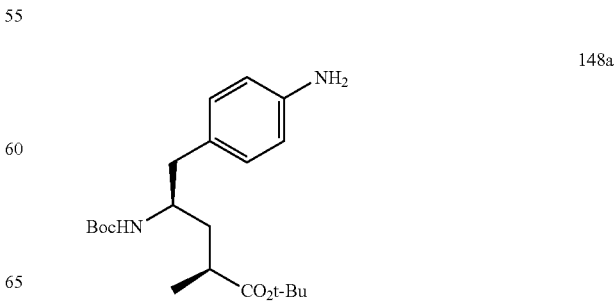

148a

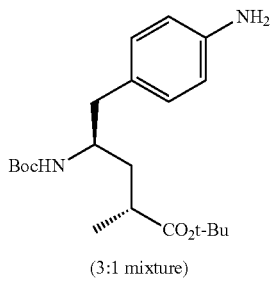

(3:1 mixture)

Compound 122 (10 mg, 0.026 mmol) was dissolved in a 2 mL mixture of TFA and DCM (1:1) at RT. After 3 h the solvents were evaporated and the residue was passed through a reverse phase column (ACN:H$_2$O; 0-100% with 0.1% TFA) to give a 3:1 mixture of compounds 149a and 149b. The major isomer in this mixture was assigned structure 149a by comparing the NMR spectrum of the mixture with the NMR of an authentic sample of compound 149a made from compound 150.

NMR (400 MHz, CD$_3$OD) δ 7.08-7.03 (m, 2H), 6.83-6.79 (m, 2H), 3.51-3.41 (m, 1H), 2.84-2.78 (m, 2H), 2.68-2.58 (m, 1H), 2.04-1.92 (m, 1H), 1.60 (d, J=7.8 Hz, 1H), 1.18 (d, J=7.0, Hz, 3H). MS m/z C$_{12}$H$_{19}$N$_2$O$_2$ (M+1)$^+$ calculated 223.1. found 223. This NMR spectrum was the basis for assigning the structures of the major component of the 148a/148b and 149a/149b mixtures.

A sample of compound 122 was passed through a reverse phase column (ACN:H$_2$O; 0-100% with 0.1% TFA) and the fractions with the minor isomer were collected and lyophilized. The resulting product was then treated with TFA and DCM to remove the Boc group. After 1 h the solvents were evaporated to give a product, which was assigned to be compound 149b, after comparing its NMR spectrum with that of compound 149a. Compound 149b: $^1$H NMR (400 MHz, CD$_3$OD) 7.36-7.23 (m, 2H), 7.22-7.09 (m, 2H), 3.59-3.40 (m, 1H), 3.04-2.84 (m, 2H), 2.61-2.45 (m, 1H) 2.07-1.87 (m, 1H), 1.73-1.58 (m, 1H), 1.21-1.09 (d, J=7.2 Hz, 3H).

Compounds 148a, 148b, 149a, and 149b can be used to prepare compounds of this invention having a 4-aminotubuphenylalanine subunit, where the stereochemistry of the alpha-methyl group is defined, utilizing the synthetic

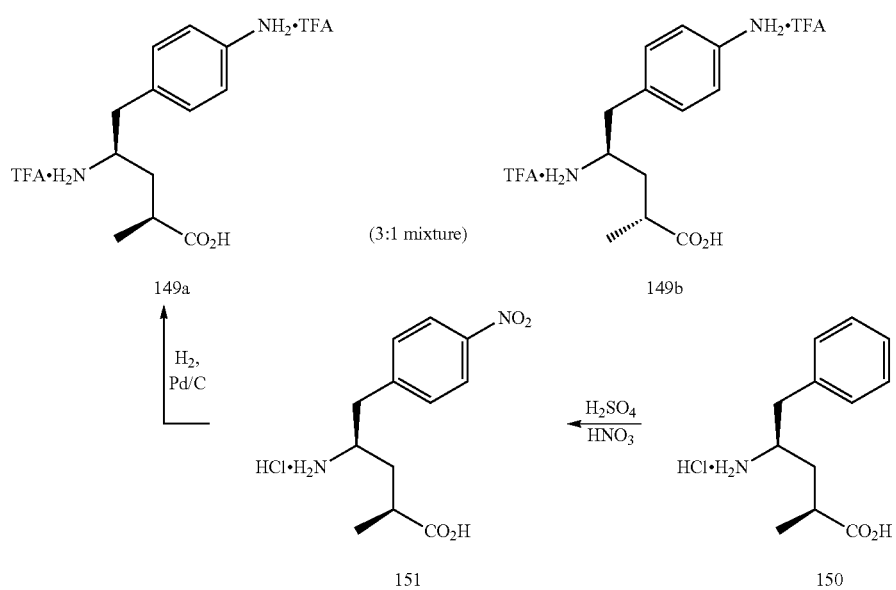

Concentrated HNO$_3$ (10 μL) was added to a 200 μL concentrated H$_2$SO$_4$ solution of tubuphenylalanine 150 (Peltier et al. 2006; 6 mg, 0.025 mmol) at 5° C. After 20 min the solution was poured onto 2 mL of cooled 7% K$_2$CO$_3$ solution. 10 mL EtOAc was then added. After separation, the organic phase was dried by evaporation and the residue was passed through a reverse phase column (ACN:H$_2$O; 0-100% with 0.1% TFA) to give nitro compound 151 (5 mg). $^1$H NMR (400 MHz, CD$_3$OD) δ 8.27-8.21 (m, 2H), 7.56-7.49 (m, 2H), 3.69-3.58 (m, 1H), 3.07 (d, J=7.2 Hz, 2H), 2.73-2.61 (m, 1H), 2.04-1.91 (m, 1H), 1.64 (ddd, J=14.7, 8.2, 4.9 Hz, 1H), 1.20 (d, J=7.1 Hz, 3H). MS m/z C$_{12}$H$_{17}$N$_2$O$_4$ (M+1)$^+$ calculated 253.1. found 253.

Nitro compound 151 then converted to compound 149a as follows: Nitro compound 151 (5 mg, 0.01 mmol) was mixed with Pd/C (10 mg, 10%) in 5 mL MeOH at RT. The flask was filled with H$_2$ using a balloon. After 1 h the mixture was filtered and evaporated to give compound 149a (4.5 mg). $^1$H approaches exemplified above, mutatis mutandis. Compounds 82a and 82b (Example 17) can also be put to similar use.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references cited in abbreviated fashion by first author (or inventor) and date earlier in this specification are provided below. Each of these references is incorporated herein by reference for all purposes.

Abe et al., WO 97/21712 (1997).
Boyd et al., US 2008/0279868 A1 (2008).
Boyd et al., U.S. Pat. No. 7,691,962 B2 (2010).
Balasubramanian et al., Bioorg. Med. Chem. Lett. 2008, 18, 2996-2999.
Balasubramanian et al., J. Med. Chem. 2009, 52 (2), 238-240.
Davis et al., US 2008/0176958 A1 (2008).
Domling, DE 10 2004 030 227 A1 (2006).
Domling et al., US 2005/0239713 A1 (2005) [2005a].
Domling et al., US 2005/0249740 A1 (2005) [2005b].
Domling et al., Mol. Diversity 2005, 9, 141-147 [2005c].
Domling et al., Ang. Chem. Int. Ed. 2006, 45, 7235-7239.
Ellman et al., WO 2009/012958 A2 (2009).
Hamel et al., Curr. Med. Chem.—Anti-Cancer Agents 2002, 2, 19-53.
Hoefle et al., DE 100 08 089 A1 (2001).
Hoefle et al., Pure Appl. Chem. 2003, 75 (2-3), 167-178.
Hoefle et al., US 2006/0128754 A1 (2006) [2006a].
Hoefle et al., US 2006/0217360 A1 (2006) [2006b].
Kaur et al., Biochem. J. 2006, 396, 235-242.
Khalil et al., ChemBioChem 2006, 7, 678-683.
Leamon et al., Cancer Res. 2008, 68 (23), 9839-9844.
Leamon et al., WO 2009/002993 A1 (2009).
Leung et al., US 2002/0169125 A1 (2002).
Low et al., WO 2009/026177 A1 (2009).
Lundquist et al., Org. Lett. 2001, 3, 781-783.
Neri et al., ChemMedChem 2006, 1, 175-180.
Patterson et al., Chem. Eur. J. 2007, 13, 9534-9541.
Patterson et al., J. Org. Chem. 2008, 73, 4362-4369.
Peltier et al., J. Am. Chem. Soc. 2006, 128, 16018-16019.
Reddy et al., Mol. Pharmaceutics 2009, 6 (5), 1518-1525.
Reichenbach et al. WO 98/13375 A1 (1998).
Richter, WO 2008/138561 A1 (2008).
Sani et al., Angew. Chem. Int. Ed. 2007, 46, 3526-3529.
Sasse et al., J. Antibiotics 2000, 53 (9), 879-885.
Sasse et al., Nature Chem. Biol. 2007, 3 (2), 87-89.
Schluep et al., Clin. Cancer Res. 2009, 15 (1), 181-189.
Shankar et al., SYNLETT 2009, 8, 1341-1345.
Shibue et al., Tetrahedron Lett. 2009 50, 3845-3848.
Steinmetz et al., Angew. Chem. Int. Ed. 2004, 43, 4888-4892.
Ullrich et al., Angew. Chemie Int. Ed. 2009, 48, 4422-4425.
Vlahov et al., Bioorg. Med. Chem. Lett. 2008, 18 (16), 4558-4561 [2008a].
Vlahov et al., US 2008/0248052 A1 (2008) [2008b].
Vlahov et al., WO 2009/055562 A1 (2009).
Vlahov et al., US 2010/0048490 A1 (2010).
Wang et al., Chem. Biol. Drug. Des 2007, 70, 75-86.
Wipf et al., Org. Lett. 2004, 6 (22), 4057-4060.
Wipf et al., Org. Lett. 2007, 9 (8), 1605-1607.
Wipf et al., US 2010/0047841 A1 (2010).

What is claimed is:

1. A conjugate having a structure according to the formula

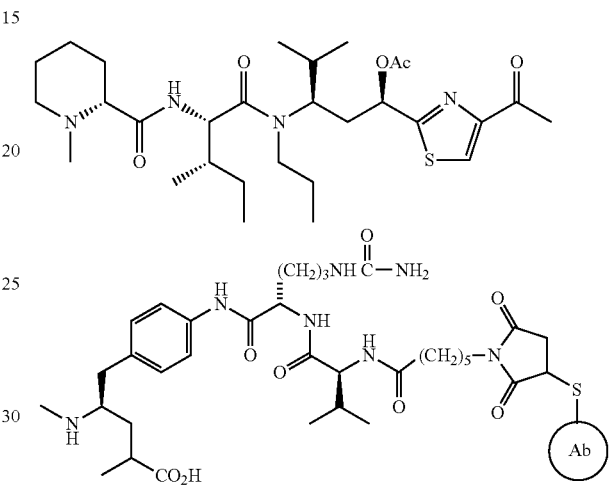

where Ab represents an antibody.

2. A conjugate according to claim 1, wherein Ab is a monoclonal antibody.

3. A conjugate according to claim 1, wherein Ab is a human monoclonal antibody.

4. A conjugate according to claim 1, wherein Ab is an anti-PSMA (prostate specific membrane antigen) antibody, an anti-CD70 antibody, or an anti-mesothelin antibody.

5. A conjugate according to claim 1, wherein Ab is an anti-CD70 antibody.

6. A conjugate according to claim 5, wherein the anti-CD70 antibody is antibody 2H5.

7. A conjugate according to claim 1, wherein Ab is an anti-mesothelin antibody.

8. A conjugate according to claim 7, wherein the anti-mesothelin antibody is antibody 6A4.

* * * * *